US010752613B2

(12) United States Patent
Piwinski et al.

(10) Patent No.: US 10,752,613 B2
(45) Date of Patent: *Aug. 25, 2020

(54) COMPOUNDS AND THEIR USE FOR REDUCING URIC ACID LEVELS

(71) Applicant: Acquist LLC, Westfield, NJ (US)

(72) Inventors: John J. Piwinski, Lebanon, NJ (US); Arshad Siddiqui, Newton, MA (US); Raymond P. Warrell, Jr., Westfield, NJ (US)

(73) Assignee: Acquist LLC, Chatham, NJ (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/310,950

(22) PCT Filed: Jun. 21, 2017

(86) PCT No.: PCT/US2017/038525
§ 371 (c)(1),
(2) Date: Dec. 18, 2018

(87) PCT Pub. No.: WO2018/005193
PCT Pub. Date: Jan. 4, 2018

(65) Prior Publication Data
US 2020/0017478 A1 Jan. 16, 2020

Related U.S. Application Data

(60) Provisional application No. 62/356,685, filed on Jun. 30, 2016, provisional application No. 62/358,669, filed on Jul. 6, 2016.

(51) Int. Cl.
| *C07D 403/12* | (2006.01) |
| *A61P 19/06* | (2006.01) |
| *A61K 9/00* | (2006.01) |
| *C07D 401/14* | (2006.01) |
| *C07D 413/12* | (2006.01) |
| *C07D 417/12* | (2006.01) |
| *C07D 487/04* | (2006.01) |
| *C07D 498/04* | (2006.01) |
| *A61K 31/506* | (2006.01) |

(52) U.S. Cl.
CPC .......... *C07D 403/12* (2013.01); *A61K 9/0019* (2013.01); *A61K 31/506* (2013.01); *A61P 19/06* (2018.01); *C07D 401/14* (2013.01); *C07D 413/12* (2013.01); *C07D 417/12* (2013.01); *C07D 487/04* (2013.01); *C07D 498/04* (2013.01)

(58) Field of Classification Search
CPC .................................................. C07D 403/12
See application file for complete search history.

(56) References Cited

U.S. PATENT DOCUMENTS

| 4,034,093 A | 7/1977 | Klemm et al. |
| 4,239,762 A | 12/1980 | Kramer et al. |
| 4,602,912 A | 7/1986 | De Sousa et al. |
| 4,634,707 A | 1/1987 | Brewer et al. |
| 4,636,508 A | 1/1987 | Brewer et al. |
| 4,762,830 A | 8/1988 | Sturm et al. |
| 4,879,276 A | 11/1989 | Brewer |
| 4,880,811 A | 11/1989 | Warrell, Jr. |
| 6,335,332 B1 | 1/2002 | Ambrogio et al. |
| 7,119,201 B2 | 10/2006 | Reiter et al. |
| 9,428,466 B2 | 8/2016 | Warrell |
| 10,093,658 B2 | 10/2018 | Warrell, Jr. et al. |
| 2009/0264401 A1 | 10/2009 | Gill et al. |

FOREIGN PATENT DOCUMENTS

| WO | 88/10114 A1 | 12/1988 |
| WO | 91/13623 A1 | 9/1991 |
| WO | 2015/073317 A1 | 5/2015 |
| WO | 2015/123003 A1 | 8/2015 |
| WO | 2016/118611 A1 | 7/2016 |

OTHER PUBLICATIONS

CAS Abstract U.S. Pat. No. 4,634,707 (1987), 2 pages.
CAS Registry No. 1349276-03-4 (2011), 1 page.
International Preliminary Report on Patentability in PCT/US2016/014107, dated Aug. 3, 2017, 7 pages.
International Search Report and Written Opinion in Intl. Appl. No. PCT/US2017/038525, dated Aug. 22, 2017, 16 pgs.
International Search Report and Written Opinion in PCT/US15/12370, dated Apr. 17, 2015, 10 pages.
International Search Report and Written Opinion in PCT/US2016/014107, dated May 17, 2016, 11 pages.
International Search Report and Written Opinion in PCT/US2017/038522, dated Oct. 3, 2017, 20 pages.
International Search Report and Written Opinion in PCT/US2017/040836, dated Sep. 12, 2017, 15 pages.
Non-Final Office Action dated Oct. 5, 2017, in U.S. Appl. No. 15/118,243, 21 pages.
Partial Search Report in PCT Application No. PCT/US2017/038522, dated Aug. 15, 2017, 2 pgs.
Provisional Opinion Accompanying the Partial Search Result in EP 15 748 739.8, dated May 22, 2017, 5 pages.
Search Opinion in EP Application No. 15 748 739.8, dated Sep. 1, 2017, 5 pgs.
Supplementary Partial European Search Report in EP 15 74 8739, dated May 22, 2017, 4 pages.
PCT International Preliminary Report on Patentability in PCT/US2017/038522 dated Jan. 10, 2019, 9 pages.

(Continued)

*Primary Examiner* — Brian E McDowell
(74) *Attorney, Agent, or Firm* — Servilla Whitney LLC

(57) ABSTRACT

Bifunctional compounds that increase uric acid excretion and reduce uric acid production, and monofunctional compounds that either increase uric acid excretion or reduce uric acid production. Methods of using these compounds for reducing uric acid levels in blood or serum, for treating disorders of uric acid metabolism, and for maintaining normal uric acid levels in blood or serum are also provided. Pharmaceutical compositions comprising the bifunctional and monofunctional compounds are also provided.

18 Claims, 20 Drawing Sheets

(56) References Cited

OTHER PUBLICATIONS

PCT International Preliminary Report on Patentability in PCT/US2017/038525 dated Jan. 10, 2019, 7 pages.
PCT Preliminary Report on Patentability in PCT/US2015/012370 dated Aug. 25, 2016, 7 pages.
Lebedyeva, Iryna O., et al., "Reaction of barbituric acid with organic azides and phosphonium ylides", Central European Journal of Chemistry, vol. 11, No. 6, 2013, pp. 1019-1022.

COMPOUNDS AND THEIR USE FOR REDUCING URIC ACID LEVELS

CROSS REFERENCE TO RELATED APPLICATIONS

This is a National Phase entry of International Application No. PCT/US2017/038525, filed on Jun. 21, 2017, which claims priority to U.S. Provisional Appln. Ser. No. 62/356,685, filed on Jun. 30, 2016, and to U.S. Provisional Appln. Ser. No. 62/358,669, filed on Jul. 6, 2016, the disclosures of which are incorporated herein by reference in their entireties.

TECHNICAL FIELD

This invention relates to pharmaceutical compositions and methods for reducing uric acid in blood or serum of a subject employing bifunctional and monofunctional compounds as active agents.

BACKGROUND

Gout afflicts more than 8 million U.S. subjects, and is associated with chronic elevation of uric acid (UA) in blood. The incidence of this condition has doubled in the past ten years. When UA exceeds solubility limits, it forms crystals that settle into joints and kidney, causing severe pain, destructive arthritis, and kidney failure. Treatment for chronic gout entails extended—if not lifelong—therapy focused on reducing UA production or increasing its excretion. The standard-of-care for initial therapy of gout is allopurinol, a drug that inhibits xanthine oxidase (XO), a key production enzyme. Launched in 2009, Uloric® (febuxostat; Takeda), has similar activity as an XO inhibitor with somewhat higher efficacy and improved safety. Xanthine oxidase inhibitors are used as initial therapy in more than 90% of gout patients; nonetheless, the therapeutic target is achieved in less than one-third of patients, the drugs have multiple side effects, and hypersensitivity (especially to allopurinol) is common. Given that most patients do not actually respond, the continued use of ineffective treatment administered over many months in order to determine the low percentage of patients who might respond represents an important burden to patients as well as substantial costs to global healthcare system. Moreover, the high proportion of failures causes many patients to become non-compliant with therapy and thus at increased risk for development of chronic complications of gout, especially destructive arthritis and renal insufficiency.

Since 2000, rapid advances in the biology of proteins known as transporters have presented an array of new drug targets. The enzyme URAT1 is a high capacity renal transporter that reabsorbs most of the UA that is initially filtered into the urine from the blood by the kidney. Inhibitors of certain urate transporters may prevent such reabsorption and thereby increase UA excretion. Several drugs are now known to inhibit URAT1, including benzbromarone (approved but withdrawn in the US by Sanofi in 2003) and lesinurad (Zurampic®, AstraZeneca), which was approved in the U.S. and EU in 2016.

These drugs are all mono-functional. That is, they inhibit only one of the two equilibrium paths that reduce the levels of UA in blood (i.e., decreased production or increased excretion). Allopurinol is an example of a drug that decreases UA production by inhibiting xanthine oxidase, but it has no effect on renal excretion. As expected, allopurinol does not affect the activity of URAT1 or other renal urate transporters. Benzbromarone and lesinurad increase UA excretion (i.e., they promote uricosuria) primarily via inhibition of URAT1, but these agents have no effect on UA production, since they have no substantial effect on xanthine oxidase. Since xanthine oxidase inhibition is the principal, preferred, and primary $1^{st}$-line form of treatment for hyperuricemia, agents that promote uricosuria are used second-line and are commonly employed only in combination with xanthine oxidase inhibitors rather than as single-agents.

Non-sedating 5-carboxanilide derivatives of barbiturates, including merbarone (5-(N-phenylcarboxamido)-2-thio-barbituric acid), have been evaluated as potential cytotoxic anticancer drugs. Subsequently, it was discovered that clinical treatment with merbarone was associated with a marked reduction of UA levels in blood. Despite these discoveries, the cytotoxic activity of merbarone completely precluded its use as a treatment for a chronic lifelong disorder of UA metabolism, since the safety of such use (primarily its genotoxicicity) posed a serious risk to other aspects of human health. Such clinical utility would only be possible if the genotoxic activity could be chemically dissociated and eliminated from the hypouricemic activity. The inventors have since described a number of non-genotoxic hypouricemic derivatives of merbarone.

There exists a compelling need for new drugs than can reduce UA levels in blood and provide better treatment for patients afflicted by gout. Reduction in UA is universally acknowledged as beneficial for patients with gout and other hyperuricemic disorders, and such reduction is directly linked to patient benefit. Reduced serum UA is accepted by international drug regulatory agencies (e.g., the U.S. Food and Drug Administration [FDA], the European Medicines Agency [EMA], etc.) as an endpoint for commercial drug approval in these diseases. As previously noted, drugs that can overcome the limited clinical activity of xanthine oxidase inhibitors are available or are currently being investigated, but only as "add-ons" for combination use. The approval of lesinurad (Zurampic®) is the most recent example. The present invention relates to new compounds that can provide alternatives to current therapy for elevated UA levels and treatment of disorders of UA metabolism such as gout. Certain of these compounds have the particular advantage of bifunctional activity (i.e., decreasing UA production by inhibiting xanthine oxidase and increasing UA excretion by inhibiting a renal urate transporter), making them suitable for use as initial therapy and as single agents rather than "add-on" therapies. In addition, certain of the compounds have reduced toxicity compared to prior art drugs such as merbarone.

SUMMARY

In a first aspect, compounds having a structure represented by Formula (I) are provided:

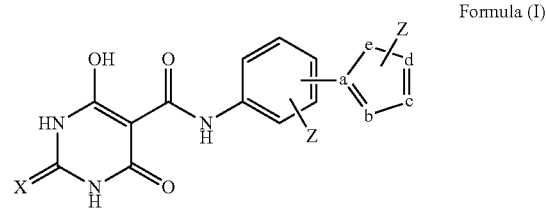

Formula (I)

wherein
X is O or S; and
Each Z is independently present or absent and, if present, is independently selected from one or more halogen atoms, —CN, —CF$_3$, —OR$^2$, —C(O)R$^2$, SR$^2$, —S(O)$_f$R$^3$ where f is 1 or 2, —N(R$^2$)$_2$, —NO$_2$, —CO$_2$R$^2$, —OCO$_2$R$^3$, OC(O)R$^2$, —CON(R$^2$)$_2$, —NR$^2$C(O)R$^2$, —SO$_2$N(R$^2$)$_2$, —NR$^2$SO$_2$R$^3$, —NR$^2$SO$_2$N(R$^2$)$_2$ or —NR$^2$C(O)N(R$^2$)$_2$, alkyl, aryl, alkenyl and alkynyl;
wherein each R$^2$ is independently H, alkyl or aryl;
wherein each R$^3$ is independently alkyl or aryl, optionally substituted with one or more halogen atoms or OR$^2$; and
wherein a, b, c, d, and e are each independently carbon or nitrogen, with the proviso that at least one of a, b, c, d and e is nitrogen and Z is not connected directly to a nitrogen except that Z may optionally be connected to a nitrogen at a, b, c, d, or e by replacement of the hydrogen of an NH group when Z is —C(O)R$^2$, —S(O)$_f$R$^3$, —CO$_2$R$^3$, —CON(R$^2$)$_2$, —SO$_2$N(R$^2$)$_2$, alkyl, aryl, alkenyl or alkynyl.

In one or more embodiments, the compound having a structure represented by Formula (I) is a compound as defined above, wherein each Z is independently present or absent and, if present, is independently selected from —CF$_3$, —OH, and phenyl, and; wherein a, b, c, d, and e are each independently carbon or nitrogen, with the proviso that 2 or 3 of a, b, c, d and e are nitrogen and Z is not connected directly to a nitrogen except that Z may optionally be connected to a nitrogen at a, b, c, d, or e by replacement of the hydrogen of an NH group when Z is phenyl.

In one or more embodiments, the compound having a structure represented by Formula (I) is a compound wherein X is O; Z is absent from the phenyl group, and; Z on the heterocyclic 5-membered ring is CF$_3$. In one or more further embodiments, the compound having a structure represented by Formula (I) is a compound wherein X is O; Z on the phenyl group is CF$_3$, and; Z is absent from the heterocyclic 5-membered ring.

In one or more specific embodiments, the compound having a structure represented by Formula (I) is a compound selected from the group consisting of:
a compound wherein X is O; both Z are absent; c, and e are N; d is NH; a is C, b is CH, and tautomers thereof;
a compound wherein X is O; Z is absent from the phenyl group and present on the 5-membered heterocyclic ring; Z is C$_6$H$_5$; d and e are N, and; c is NH; a and b are C, and tautomers thereof;
a compound wherein X is O; both Z are absent; c is NH; d is N; a is C, and; b and e are CH, and tautomers thereof;
a compound wherein X is O; both Z are absent; b and c are N; e is NH; a is C, and; d is CH, and tautomers thereof;
a compound wherein X is O; Z on the phenyl group is CF$_3$; Z is absent from the 5-membered heterocyclic ring; c is NH; d and e are N; a is C, and; b is CH, and tautomers thereof;
a compound wherein X is O; Z is absent from the phenyl group and present on the 5-membered heterocyclic ring; Z is CF$_3$; e is NH; c and d are N, and; a and b are C, and tautomers thereof;
a compound wherein X is O; Z is absent from the phenyl group and present on the 5-membered heterocyclic ring; Z is OH; d is N; e is NH; a is C, and; b is CH, and tautomers thereof;
a compound wherein X is O; Z is absent from the phenyl group and present on the 5-membered heterocyclic ring; Z is CF$_3$; c is NH; d is N; e is CH, and; a and b are C, and tautomers thereof;
a compound wherein X is O; Z is absent from the phenyl group and present on the 5-membered heterocyclic ring; Z is CF$_3$; b and d are N; e is NH; and; a and c are C, and tautomers thereof;
a compound wherein X is O; Z is absent from the phenyl group and present on the 5-membered heterocyclic ring; Z is CF$_3$; a and e are N, and; b and d are CH, c is C, and tautomers thereof;
a compound wherein X is O; Z is absent from the phenyl group and present on the 5-membered heterocyclic ring; Z is CF$_3$; a and c are C; b is CH, and; d is N, and; e is NH, and tautomers thereof; and
a compound wherein X is O; Z is absent from the phenyl group and present on the 5-membered heterocyclic ring; Z is CF$_3$; a and b are C; c is CH; d is N, and; e is NH, and tautomers thereof.

In certain embodiments of any of the compounds having a structure represented by Formula (I), alkyl moieties may each independently be C1-C6, aryl moieties may each independently be C6-C10, alkenyl moieties may each independently be C2-C6, and alkynyl moieties may each independently be C2-C6.

A further aspect relates to methods for reducing uric acid levels in blood or serum of a subject comprising administering a compound having a structure represented by Formula (I), or a combination thereof, to a subject in need thereof in an amount effective to reduce blood or serum uric acid levels. In a modification of this embodiment, the methods comprise administering a compound according to a specific embodiment of the compounds of Formula (I), or a combination thereof, as described above, to a subject in need thereof in an amount effective to reduce blood or serum uric acid levels.

A modification of this aspect relates to methods for preventing elevation of uric acid levels in blood or serum of a subject comprising administering a compound having a structure represented by Formula (I), or a combination thereof, to a subject in need thereof in an amount effective to prevent elevation of blood or serum uric acid levels. In a specific embodiment of this aspect, the methods for preventing elevation of uric acid levels in blood or serum of a subject comprise administering to a subject in need thereof one a compound according to a specific embodiment of the compounds of Formula (I), or a combination thereof, as described above, to a subject in need thereof in an amount effective to reduce blood or serum uric acid levels.

In certain embodiments of these methods, a compound having a structure represented by Formula (I), or a combination thereof, is administered to a subject with gout, hyperuricemia, kidney disease, arthritis, kidney stones, kidney failure, urolithiasis, plumbism, hyperparathyroidism, psoriasis, inborn genetic errors of metabolism including but not limited to Lesch-Nyhan syndrome, sarcoidosis or cardiovascular disease (including but not limited to atherosclerosis) or who has a disorder of uric acid metabolism associated with transplantation of blood, bone marrow or solid organs, to reduce uric acid levels. In specific embodiments, the drug(s) are administered to a subject with gout or hyperuricemia to reduce uric acid levels. In other embodiments, a compound according to a specific embodiment of the compounds of Formula (I), or a combination thereof, as described above, is/are administered to a subject with gout, hyperuricemia, kidney disease, arthritis, kidney stones, kidney failure, urolithiasis, plumbism, hyperparathyroidism, psoriasis, inborn genetic errors of metabolism including but not limited to Lesch-Nyhan syndrome, sarcoidosis, cardiovascular disease including but not limited to atherosclerosis, or who has a disorder of uric acid metabolism associated with transplantation of blood, bone marrow or solid organs, to reduce uric acid levels.

In certain embodiments of any of the foregoing methods, a compound having a structure represented by Formula (I), or a combination thereof, is administered by injection, infusion, intranasal, intrarectal, or oral administration. In other embodiments, a compound having a structure represented by Formula (I), or a combination thereof, is administered by injection, infusion, or oral administration.

In certain embodiments of any of the foregoing methods, a compound having a structure represented by Formula (I), or a combination thereof, is administered in a formulation that enables controlled release. Controlled release formulations release the active ingredient more slowly or extend the duration of its action within the body. In specific embodiments, the controlled release formulation is an oral controlled release formulation. In other embodiments of any of the foregoing methods, a compound according to a specific embodiment of the compounds of Formula (I), or a combination, as described above, is/are administered in a formulation that enables controlled release.

In certain embodiments of any of the foregoing methods, blood or serum uric acid levels are reduced by at least about 25% compared to blood or serum uric acid levels prior to administration of a compound having a structure represented by Formula (I), or a combination thereof. In specific embodiments, blood or serum uric acid levels of the subject are reduced by at least about 50% compared to levels prior to administration. In a specific embodiment, uric acid levels are reduced by about 75% even at daily doses of 1,500 mg/m$^2$/day or less.

In certain embodiments of any of the foregoing methods, a compound having a structure represented by Formula (I), or a combination thereof, is administered to the subject up to four times per day, once daily, once, twice or three times per week or once monthly. In other embodiments of any of the foregoing methods, a compound according to a specific embodiment of the compounds of Formula (I), or a combination, as described above, is/are administered to the subject up to four times per day, once daily, once, twice or three times per week or once monthly.

A fourth aspect relates to methods for treating a disorder of uric acid metabolism associated with or caused by elevated uric acid in blood or serum comprising administering to a subject in need thereof a compound having a structure represented by Formula (I), or a combination thereof, in an amount effective to reduce blood or serum uric acid levels or prevent elevation of blood or serum uric acid levels, thereby treating the disorder of uric acid metabolism. One such embodiment relates to methods for treating a disorder of uric acid metabolism associated with or caused by elevated uric acid in blood or serum comprising administering to the subject a compound according to a specific embodiment of the compounds of Formula (I), or a combination, as described above, up to four times per day, once daily, once, twice or three times per week or once monthly.

A further aspect of the invention provides pharmaceutical compositions comprising a compound having a structure represented by Formula (I), or a combination thereof, and a pharmaceutically acceptable carrier. In a specific embodiment, the pharmaceutical composition comprises a compound according to a specific embodiment of the compounds of Formula (I), or a combination thereof, as described above. In certain embodiments of the pharmaceutical composition, the pharmaceutically acceptable carrier is selected from the group consisting of one or more of a solvent, a dispersing agent, a coating, a surfactant, a preservative, an alcohol, a polyol, and an isotonic agent. In certain embodiments of any of the foregoing pharmaceutical compositions, the composition is formulated for administration by injection, infusion or oral routes. In certain embodiments of any of the foregoing pharmaceutical compositions, the composition is formulated as a solution, emulsion, capsule, or tablet. In certain embodiments of any of the foregoing pharmaceutical compositions, the composition is formulated for controlled release of the compound having a structure represented by Formula (I), or a combination thereof, for the purpose of releasing the active ingredient more slowly or extending the duration of its action within the body.

A further aspect provides methods for synthesizing the compounds discussed above, as discussed in more detail below.

DETAILED DESCRIPTION

Figure 1:
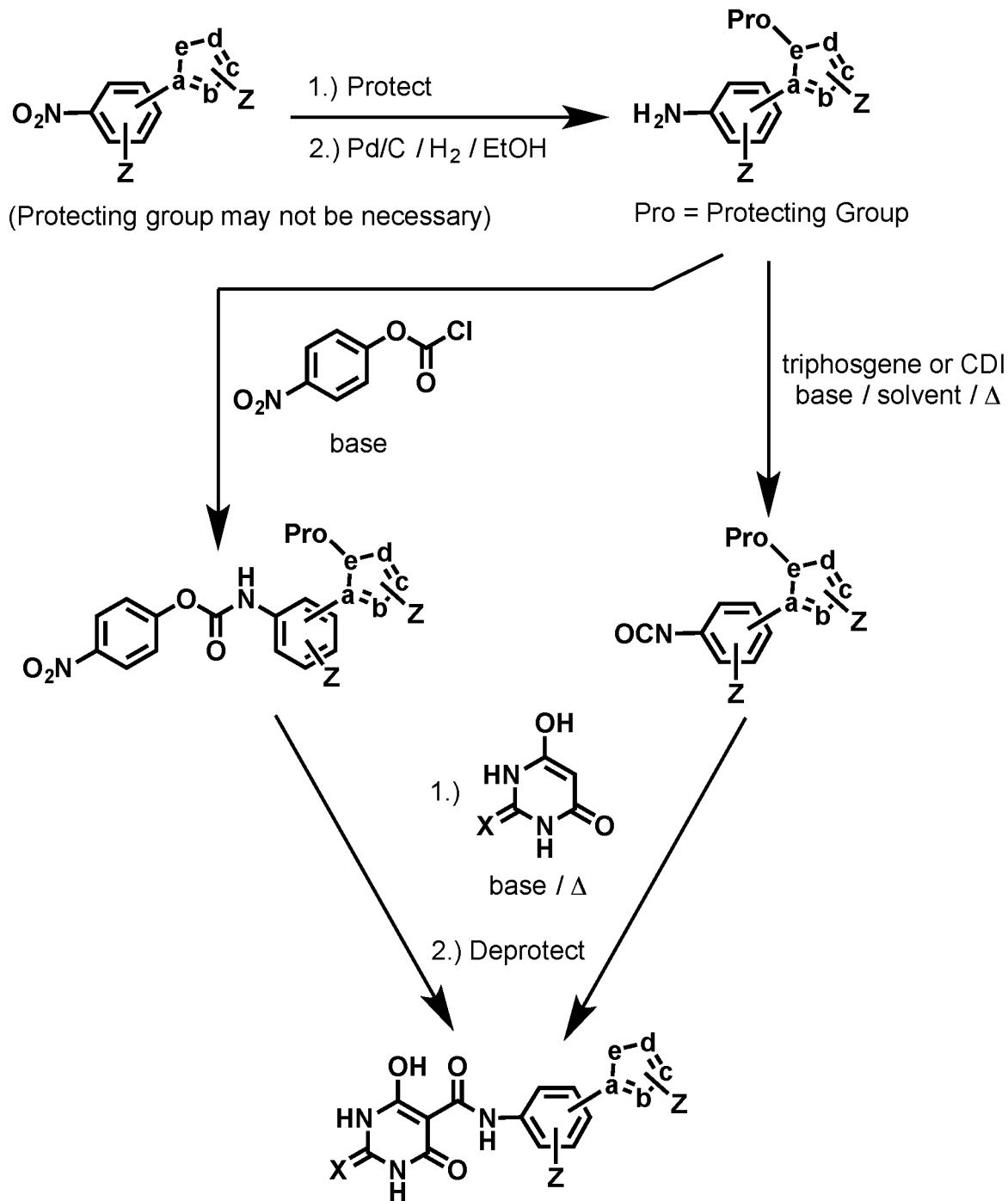
FIG. 1 illustrates a general synthesis scheme for preparation of compounds having a structure represented by Formula (I).

Before describing several exemplary embodiments provided herein, it is to be understood that the invention is not limited to the details of construction or process steps set forth in the following description. The invention is capable of other embodiments and of being practiced or being carried out in various ways.

Reference throughout this specification to "one embodiment," "certain embodiments," "one or more embodiments" or "an embodiment" means that a particular feature, structure, material, or characteristic described in connection with the embodiment is included in at least one embodiment of the invention. Thus, the appearances of the phrases such as "in one or more embodiments," "in certain embodiments," "in one embodiment" or "in an embodiment" in various places throughout this specification are not necessarily referring to the same embodiment of the invention. Furthermore, the particular features, structures, materials, or characteristics may be combined in any suitable manner in one or more embodiments.

As used herein, the term "bifunctional" with respect to disclosed compounds means that the compound inhibits both a renal transporter, including but not limited to URAT1, and xanthine oxidase. The potency of inhibition of either target may vary, but in general an IC50 of less than about 100 μM for both xanthine oxidase and a renal transporter such as URAT1 is considered bifunctional. An IC50 of less than about 50 μM for both xanthine oxidase and URAT1 is considered a particularly active bifunctional compound, and an IC50 of less than 10 μM is considered a highly potent bifunctional compound.

As used herein, the term "monofunctional" with respect to disclosed compounds means that the compound inhibits an enzyme in the uric acid metabolic pathway involved in uric acid excretion that is either a renal transporter, including but not limited to URAT1, or an enzyme involved in uric acid production, including but not limited to xanthine oxidase, but not both. The potency of inhibition of single target may vary, but in general an IC50 of greater than about 100 μM for one of xanthine oxidase or URAT1, and an IC50 of less than about 100 μM for the other of xanthine oxidase or URAT1, is considered monofunctional. An IC50 of less than about 50 μM for one of xanthine oxidase or URAT1, and an IC50 of greater than about 100 μM for the other of xanthine oxidase or URAT1, is considered a particularly active monofunctional compound. An IC50 of less than about 10 μM for one of xanthine oxidase or URAT1, and an IC50 of greater than about 100 μM for the other of xanthine oxidase or URAT1, is considered a highly potent monofunctional compound.

As used herein, the term "treatment" refers to reducing elevated uric acid levels in blood or serum, preferably by reducing levels to the normal, low-normal or sub-normal range, with an overall goal of relieving symptoms and/or preventing recurrences of active disease. For example, a typical "therapeutic target" for treatment of elevated serum uric acid is a level ≤6.0 mg/dL. "Elevated" uric acid levels generally refer to above-normal uric acid levels, as long-term elevated levels can result in conditions that require additional treatment.

As used herein, the term "preventing" elevation of uric acid levels in blood or serum refers to maintaining normal or therapeutically acceptable uric acid levels in blood or serum in a subject who would otherwise experience an increase in uric acid levels, with an overall goal of preventing development or recurrence of symptoms and/or preventing recurrences of active disease. It will be appreciated that prevention of elevation of uric acid levels is a goal of the long-term maintenance therapy discussed below, as well as certain short-term conditions.

The numbering of the positions on the barbiturate ring used herein follows the convention of Warrell (U.S. Pat. No. 4,880,811). It is also to be understood that although the compounds disclosed herein are generally illustrated by specific chemical structures, the disclosure of the compounds is intended to include their tautomers. Representative examples of tautomers in the barbiturate and triazole rings include the structures depicted below, as well as any additional tautomers on the substituents of Formula I:

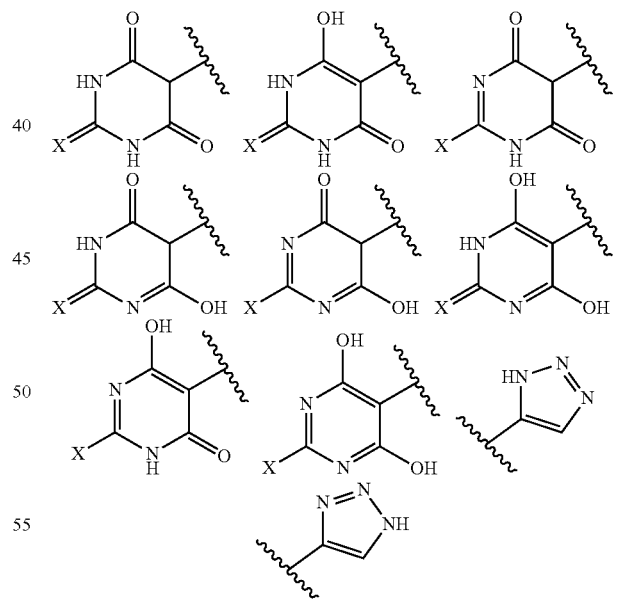

The compounds described herein meet certain needs in the therapeutic field of reduction of uric acid levels in blood and treatment of disorders of uric acid metabolism that are associated with, or caused by, elevated uric acid levels in blood or serum. Certain of the compounds are potent monofunctional inhibitors of URAT1 or xanthine oxidase. Certain of the compounds are bifunctional inhibitors of both URAT1 and xanthine oxidase.

The improved biological activity profile of the compounds of the invention and their potency make these compounds useful new drugs for reducing uric acid levels in blood, and for treating disorders of uric acid metabolism that are associated with, or caused by, elevated uric acid levels in blood or serum, including gout. Of particular significance is the advantage that the bifunctional compounds can be used effectively as monotherapy for reducing uric acid levels in blood, for treating or preventing disorders of uric acid metabolism, and specifically for treating gout.

In a first aspect, compounds having a structure represented by Formula (I) are provided:

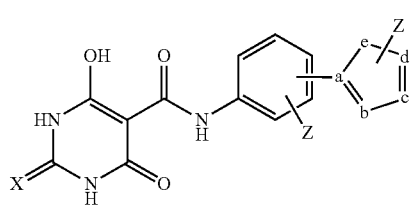

Formula (I)

wherein
X is O or S; and
Each Z is independently present or absent and, if present, is independently selected from one or more halogen atoms, —CN, —CF$_3$, —OR$^2$, —C(O)R$^2$, SR$^2$, —S(O)$_f$R$^3$ where f is 1 or 2, —N(R$^2$)$_2$, —NO$_2$, —CO$_2$R$^2$, —OCO$_2$R$^3$, OC(O)R$^2$, —CON(R$^2$)$_2$, —NR$^2$C(O)R$^2$, —SO$_2$N(R$^2$)$_2$, —NR$^2$SO$_2$R$^3$, —NR$^2$SO$_2$N(R$^2$)$_2$ or —NR$^2$C(O)N(R$^2$)$_2$, alkyl, aryl, alkenyl and alkynyl;
wherein each R$^2$ is independently H, alkyl or aryl;
wherein each R$^3$ is independently alkyl or aryl, optionally substituted with one or more halogen atoms or OR$^2$; and
wherein a, b, c, d, and e are each independently carbon or nitrogen, with the proviso that at least one of a, b, c, d and e is nitrogen and Z is not connected directly to a nitrogen except that Z may optionally be connected to a nitrogen at a, b, c, d, or e by replacement of the hydrogen of an NH group when Z is —C(O)R$^2$, —S(O)$_f$R$^3$, —CO$_2$R$^3$, —CON(R$^2$)$_2$, —SO$_2$N(R$^2$)$_2$, alkyl, aryl, alkenyl or alkynyl.

In a specific embodiment, the compound having a structure represented by Formula (I) is a compound wherein:
X is O or S;
each Z is independently present or absent and, if present, is independently selected from —CF$_3$, —OR$^2$, and aryl, wherein R$^2$ is H, alkyl or aryl; and;
a, b, c, d, and e are each independently carbon or nitrogen, with the proviso that 2 or 3 of a, b, c, d and e are nitrogen and Z is not connected directly to a nitrogen except that Z may optionally be connected to a nitrogen at a, b, c, d, or e by replacement of the hydrogen of an NH group when Z is phenyl;

In one or more embodiments, the compound having a structure represented by Formula (I) is a compound as defined above, wherein the 5-member heterocyclic ring is a substituted or unsubstituted triazole, or a substituted or unsubstituted pyrazole. In specific embodiments, such compounds may have a structure represented by Formula (I), wherein each Z is independently present or absent and, if present, is independently selected from —CF$_3$, —OH, and phenyl, and; a, b, c, d, and e are each independently carbon or nitrogen, with the proviso that 2 or 3 of a, b, c, d and e are nitrogen and Z is not connected directly to a nitrogen except that Z may optionally be connected to a nitrogen at a, b, c, d, or e by replacement of the hydrogen of an NH group when Z is phenyl.

Specific examples of compounds having a structure represented by Formula (I) include the following:

1. A compound wherein X is O; both Z are absent, and; the 5-member heterocyclic ring is a substituted or unsubstituted triazole. Representative examples of such compounds include:

The compound wherein c, d, and e are N; d is NH, and; a is C, b is CH, and tautomers thereof, having a structure represented by Formula (I$_a$) (N-(3-(1H-1,2,3-triazol-5-yl)phenyl)-6-hydroxy-2,4-dioxo-1,2,3,4-tetrahydropyrimidine-5-carboxamide):

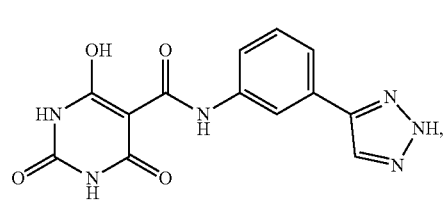

Formula (I$_a$)

and
The compound wherein b and c are N; e is NH; a is C, and; d is CH, and tautomers thereof, having a structure represented by Formula (I$_b$) (N-(4-(4H-1,2,4-triazol-3-yl)phenyl)-6-hydroxy-2,4-dioxo-1,2,3,4-tetrahydropyrimidine-5-carboxamide):

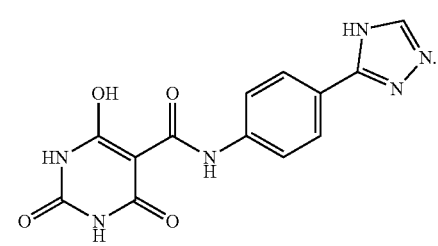

Formula (I$_b$)

2. A compound wherein X is O; Z is absent from the phenyl group and present on the 5-membered heterocyclic ring, and; the 5-membered heterocyclic ring is a substituted or unsubstituted triazole. Representative examples of such compounds include:

The compound wherein Z is C$_6$H$_5$; d and e are N; c is NH, and; a and b are C, and tautomers thereof, having a structure represented by Formula (I$_c$) (6-hydroxy-2,4-dioxo-N-(4-(4-phenyl-1H-1,2,3-triazol-5-yl)phenyl)-1,2,3,4-tetrahydropyrimidine-5-carboxamide):

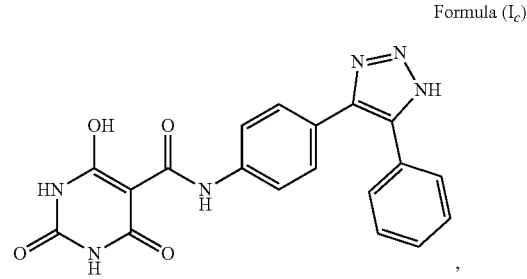 [SMILES: O=C(Nc1ccc(-c2nn[nH]c2-c2ccccc2)cc1)c1c(O)[nH]c(=O)[nH]c1=O]

Formula (I$_c$)

,

The compound wherein Z is CF₃; e is NH; c and d are N, and; a and b are C, and tautomers thereof, having a structure represented by Formula (I_d) (6-hydroxy-2,4-dioxo-N-(4-(5-(trifluoromethyl)-3H-1,2,3-triazol-4-yl)phenyl)-1,2,3,4-tetrahydropyrimidine-5-carboxamide):

Formula (I_d)

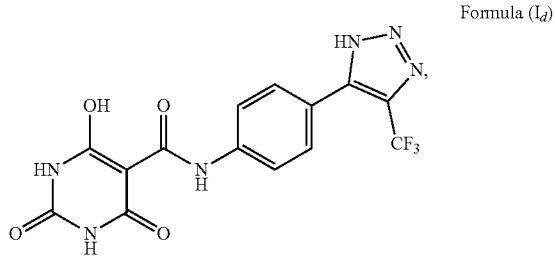 [SMILES: O=C(Nc1ccc(-c2[nH]nnc2C(F)(F)F)cc1)c1c(O)[nH]c(=O)[nH]c1=O]

and

The compound wherein Z is CF₃; b and d are N; e is NH, and; a and c are C, and tautomers thereof, having a structure represented by Formula (I_e) (6-hydroxy-2,4-dioxo-N-(4-(3-(trifluoromethyl)-1H-1,2,4-triazol-5-yl)phenyl)-1,2,3,4-tetrahydropyrimidine-5-carboxamide):

Formula (I_e)

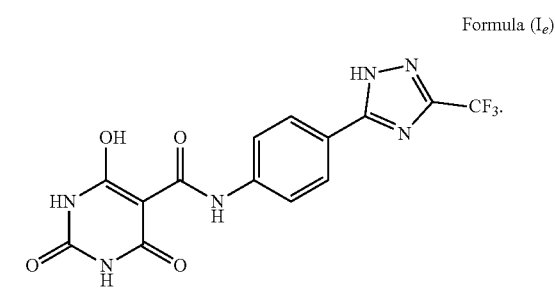 [SMILES: O=C(Nc1ccc(-c2nc(C(F)(F)F)n[nH]2)cc1)c1c(O)[nH]c(=O)[nH]c1=O]

3. A compound wherein X is O; Z is absent from both the phenyl group and the 5-membered heterocyclic ring, and; the 5-membered heterocyclic ring is a substituted or unsubstituted pyrazole. Representative examples of such compounds include:

The compound wherein c is NH; d is N; a is C, and; b and e are CH, and tautomers thereof, having a structure represented by Formula (I_f) (N-(4-(1H-pyrazol-4-yl)phenyl)-6-hydroxy-2,4-dioxo-1,2,3,4-tetrahydropyrimidine-5-carboxamide):

Formula (I_f)

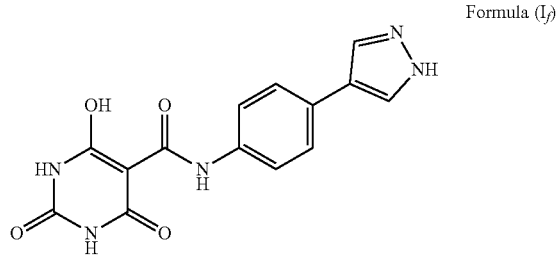 [SMILES: O=C(Nc1ccc(-c2cn[nH]c2)cc1)c1c(O)[nH]c(=O)[nH]c1=O]

4. A compound wherein X is O; Z is present on the phenyl group and absent from the 5-membered heterocyclic ring, and; the 5 membered heterocyclic ring is a substituted or unsubstituted triazole. Representative examples of such compounds include:

The compound wherein Z is CF₃; c is NH; d and e are N; a is C, and; b is CH, and tautomers thereof, having structures represented by Formula (I_g) (N-(4-(1H-1,2,3-triazol-5-yl)-3-(trifluoromethyl)phenyl)-6-hydroxy-2,4-dioxo-1,2,3,4-tetrahydropyrimidine-5-carboxamide) and Formula (I_h) (N-(4-(1H-1,2,3-triazol-5-yl)-2-(trifluoromethyl)phenyl)-6-hydroxy-2,4-dioxo-1,2,3,4-tetrahydropyrimidine-5-carboxamide):

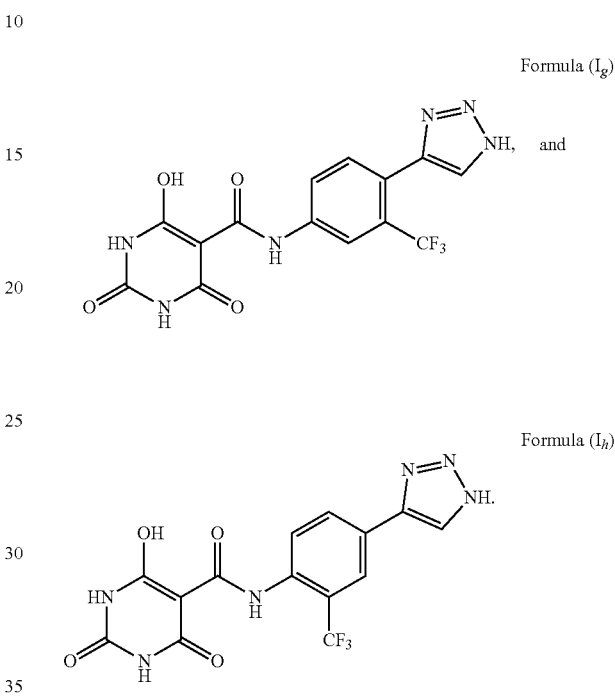

5. A compound wherein X is O; Z is absent from the phenyl group and present on the 5-membered heterocyclic ring, and; the 5 membered heterocyclic ring is a substituted or unsubstituted pyrazole. Representative examples of such compounds include:

The compound wherein Z is OH; d is N; e is NH; a is C; b is CH, and; c is COH, and tautomers thereof, having a structure represented by Formula (I_i) (6-hydroxy-N-(4-(3-hydroxy-1H-pyrazol-5-yl)phenyl)-2,4-dioxo-1,2,3,4-tetrahydropyrimidine-5-carboxamide):

Formula (I_i)

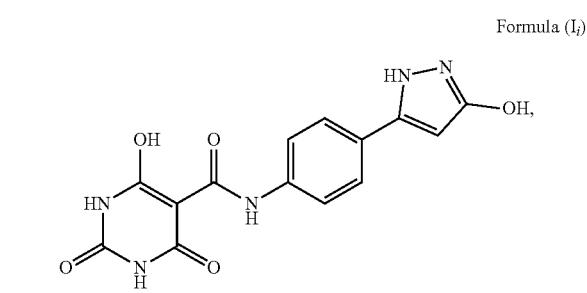 [SMILES: O=C(Nc1ccc(-c2cc(O)n[nH]2)cc1)c1c(O)[nH]c(=O)[nH]c1=O]

The compound wherein Z is CF₃; c is NH; d is N; e is CH, and; a and b are C, and tautomers thereof, having a structure represented by Formula (I_j) (6-hydroxy-2,4-dioxo-N-(4-(5-(trifluoromethyl)-1H-pyrazol-4-yl)phenyl)-1,2,3,4-tetrahydropyrimidine-5-carboxamide):

Formula (I$_j$)

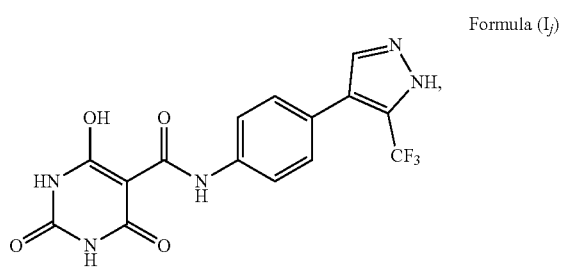 [SMILES: O=C(Nc1ccc(-c2cn[nH]c2C(F)(F)F)cc1)c1c(O)[nH]c(=O)[nH]c1=O]

The compound wherein Z is CF$_3$; a and e are N; b and d are CH; and c is C, and tautomers thereof, having a structure represented by Formula (I$_k$) (6-hydroxy-2,4-dioxo-N-(4-(4-(trifluoromethyl)-1H-pyrazol-1-yl)phenyl)-1,2,3,4-tetrahydropyrimidine-5-carboxamide):

Formula (I$_k$)

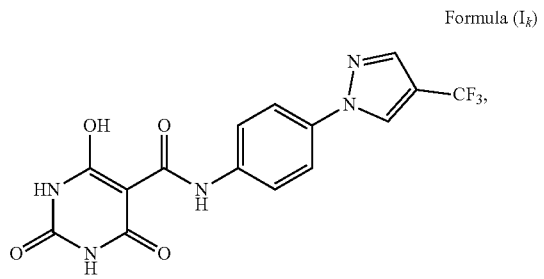 [SMILES: O=C(Nc1ccc(-n2cc(C(F)(F)F)cn2)cc1)c1c(O)[nH]c(=O)[nH]c1=O]

The compound wherein Z is CF$_3$; a is C; b is CH; c is C; d is N, and; e is NH, and tautomers thereof, having a formula represented by Formula (I$_l$) (6-hydroxy-2,4-dioxo-N-(4-(3-(trifluoromethyl)-1H-pyrazol-5-yl)phenyl)-1,2,3,4-tetrahydropyrimidine-5-carboxamide):

Formula (I$_l$)

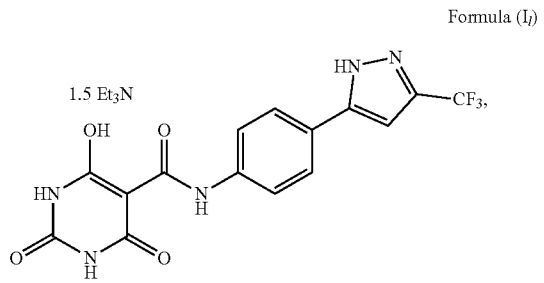 [SMILES: O=C(Nc1ccc(-c2cc(C(F)(F)F)n[nH]2)cc1)c1c(O)[nH]c(=O)[nH]c1=O]

and the compound wherein Z is CF$_3$; a is C; b is C; c is CH; d is N, and; e is NH, and tautomers thereof, having a structure represented by Formula (I$_m$) (6-hydroxy-2,4-dioxo-N-(4-(4-(trifluoromethyl)-1H-pyrazol-5-yl)phenyl)-1,2,3,4-tetrahydropyrimidine-5-carboxamide):

Formula (I$_m$)

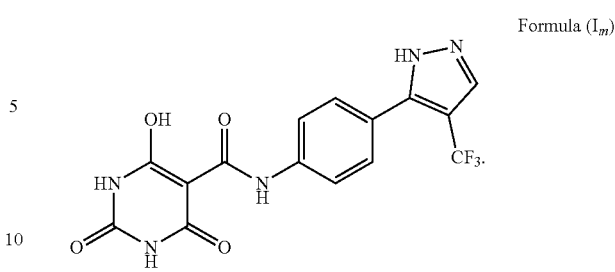

It is understood that compounds of the Formula (I), and all of its embodiments, can exist as tautomers. It is also to be understood that the structure illustrated in Formula (I) encompasses all possible tautomers.

Reference herein to compounds having a structure represented by Formula (I), or a combination thereof, is intended to include all compounds falling within the generic structure identified as Formula (I), as well as the more specific embodiments and examples described above. Included are compounds wherein the 5-member heterocyclic ring is a substituted or unsubstituted triazole or a substituted or unsubstituted pyrazole, and compounds wherein Z is —CF$_3$, —OH or phenyl. Also included are the specific compounds having structures represented by Formula (I$_a$), Formula (I$_b$), Formula (I$_c$), Formula (I$_d$), Formula (I$_e$), Formula (I$_f$), Formula (I$_g$), Formula (I$_h$), Formula (I$_i$), Formula (I$_j$), Formula (I$_k$), Formula (I$_l$), and Formula (I$_m$), and their tautomers.

Figure 2:
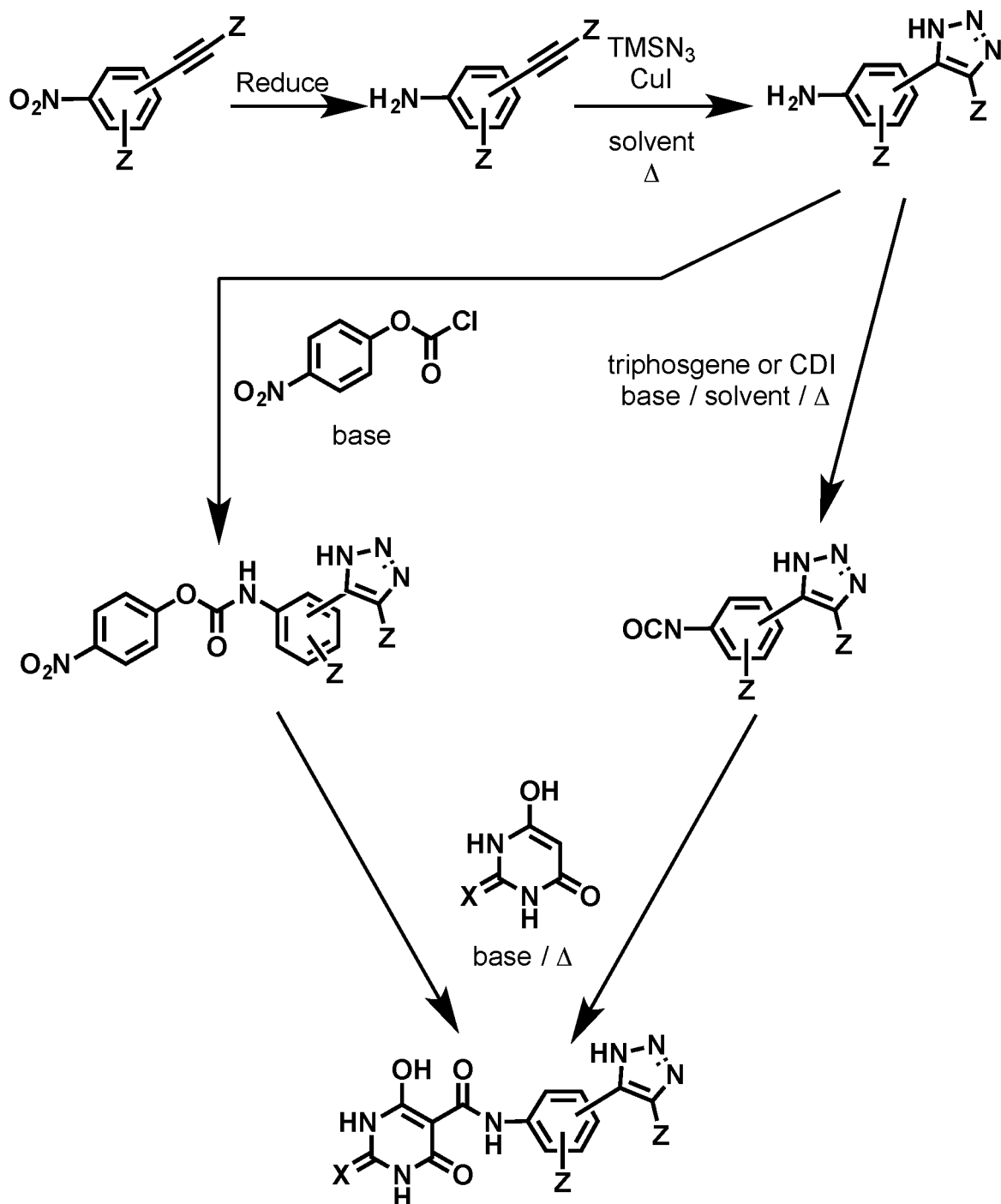
FIG. 2 illustrates a general synthesis scheme for preparation of certain compounds having a structure represented by Formula (I), wherein the 5-member ring is a triazole.
Figure 3:
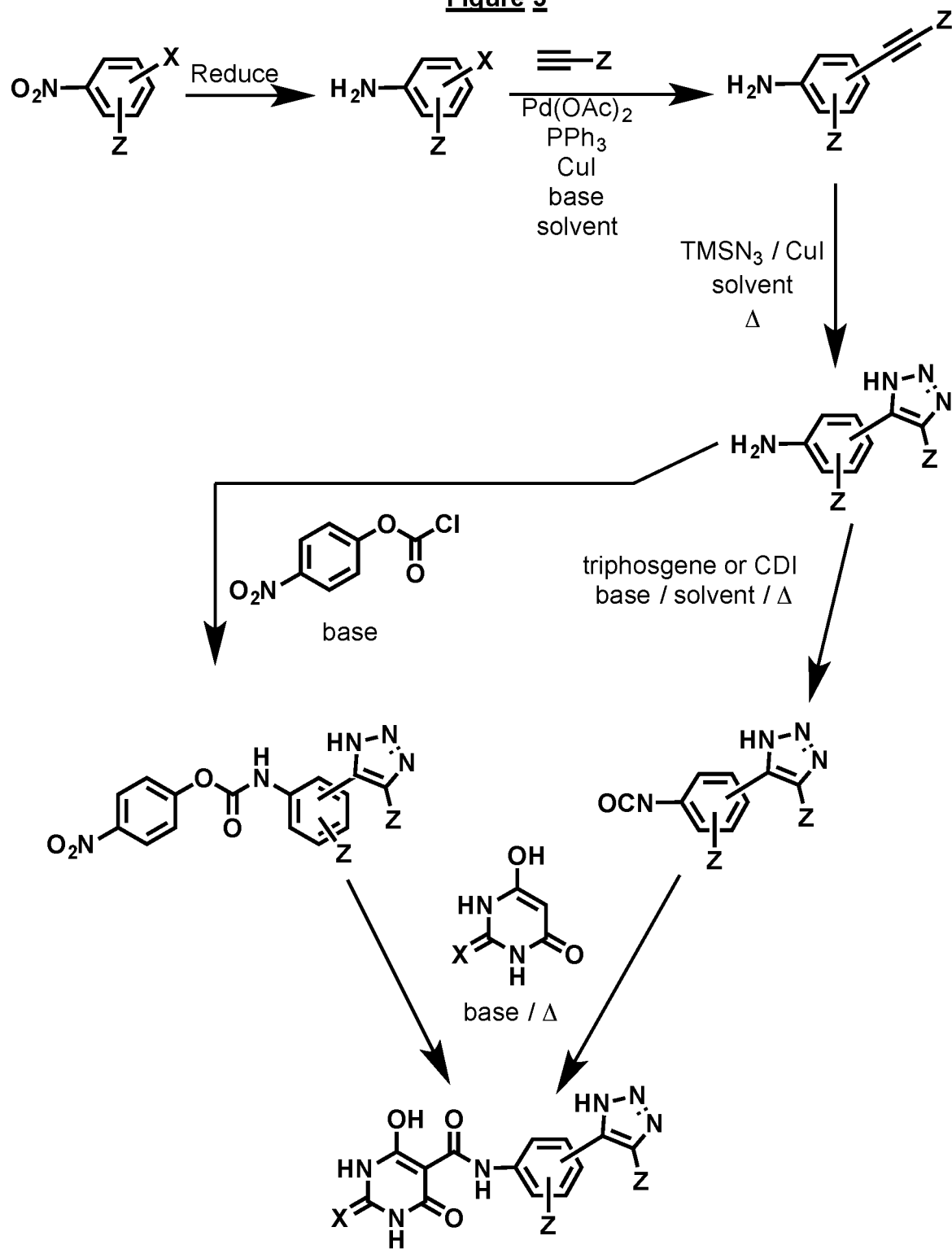
FIG. 3 illustrates an alternative general synthesis scheme for preparation of certain compounds having a structure represented by Formula (I), wherein the 5-member ring is a triazole.
Figure 4:
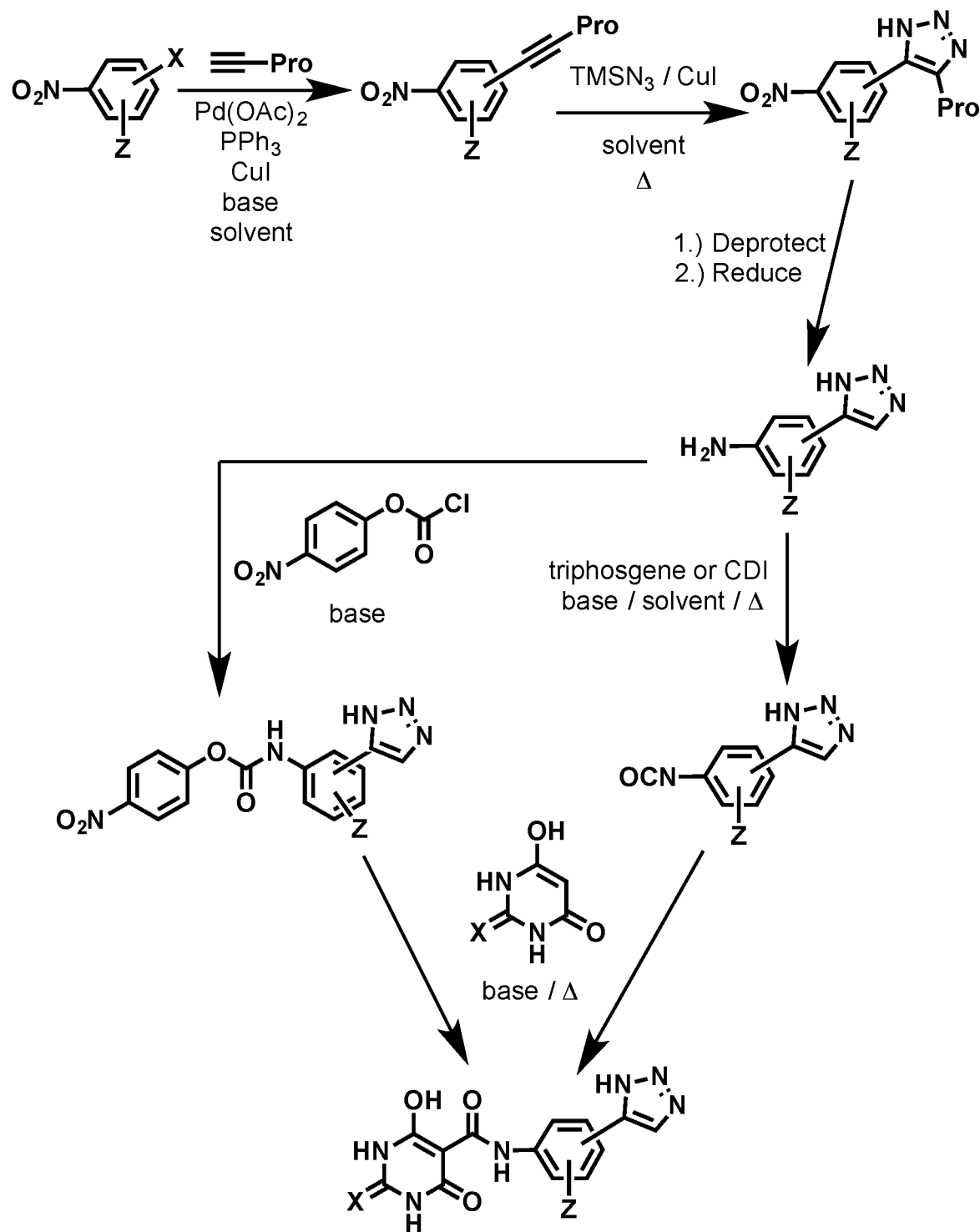
FIG. 4 illustrates a further alternative general synthesis scheme for preparation of certain compounds having a structure represented by Formula (I), wherein the 5-member ring is a triazole.
Figure 5:
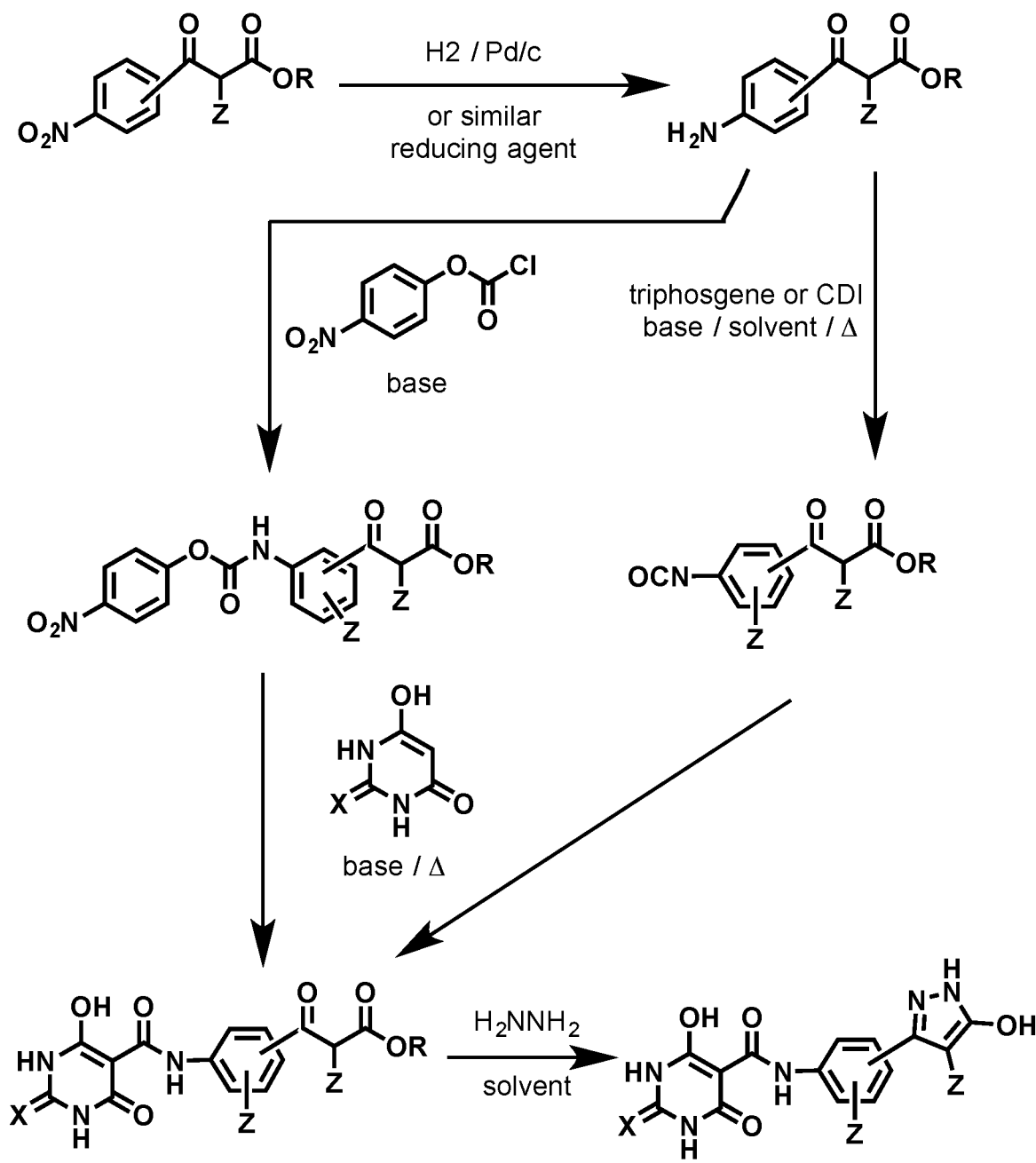
FIG. 5 illustrates a general synthesis scheme for preparation of certain compounds having a structure represented by Formula (I), wherein the 5-member ring is a pyrazole.
Figure 6:
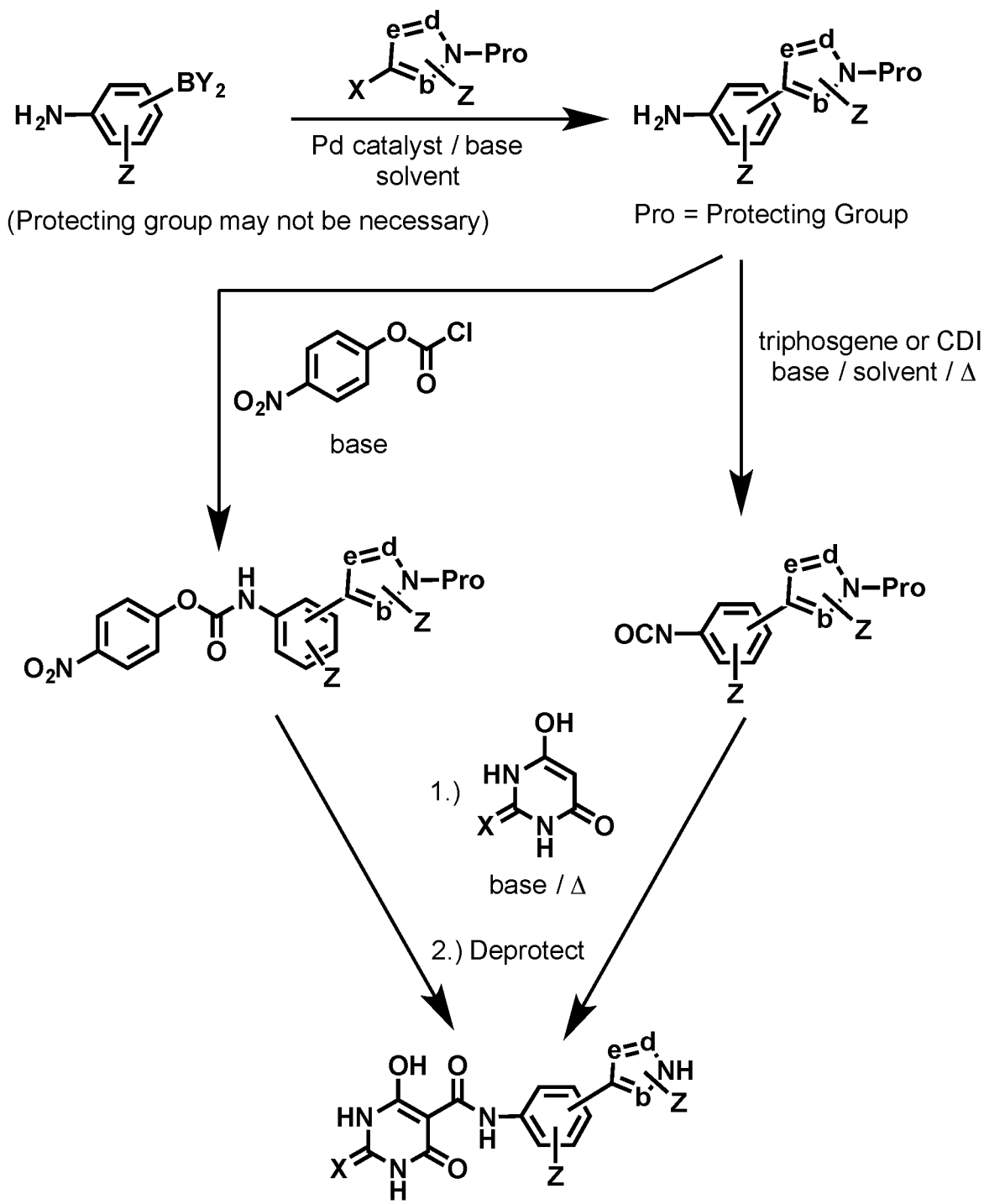
FIG. 6 illustrates a general synthesis scheme for preparation of certain compounds having a structure represented by Formula (I), wherein the 5-member ring is a pyrazole, a triazole or a tetrazole.
Figure 7:
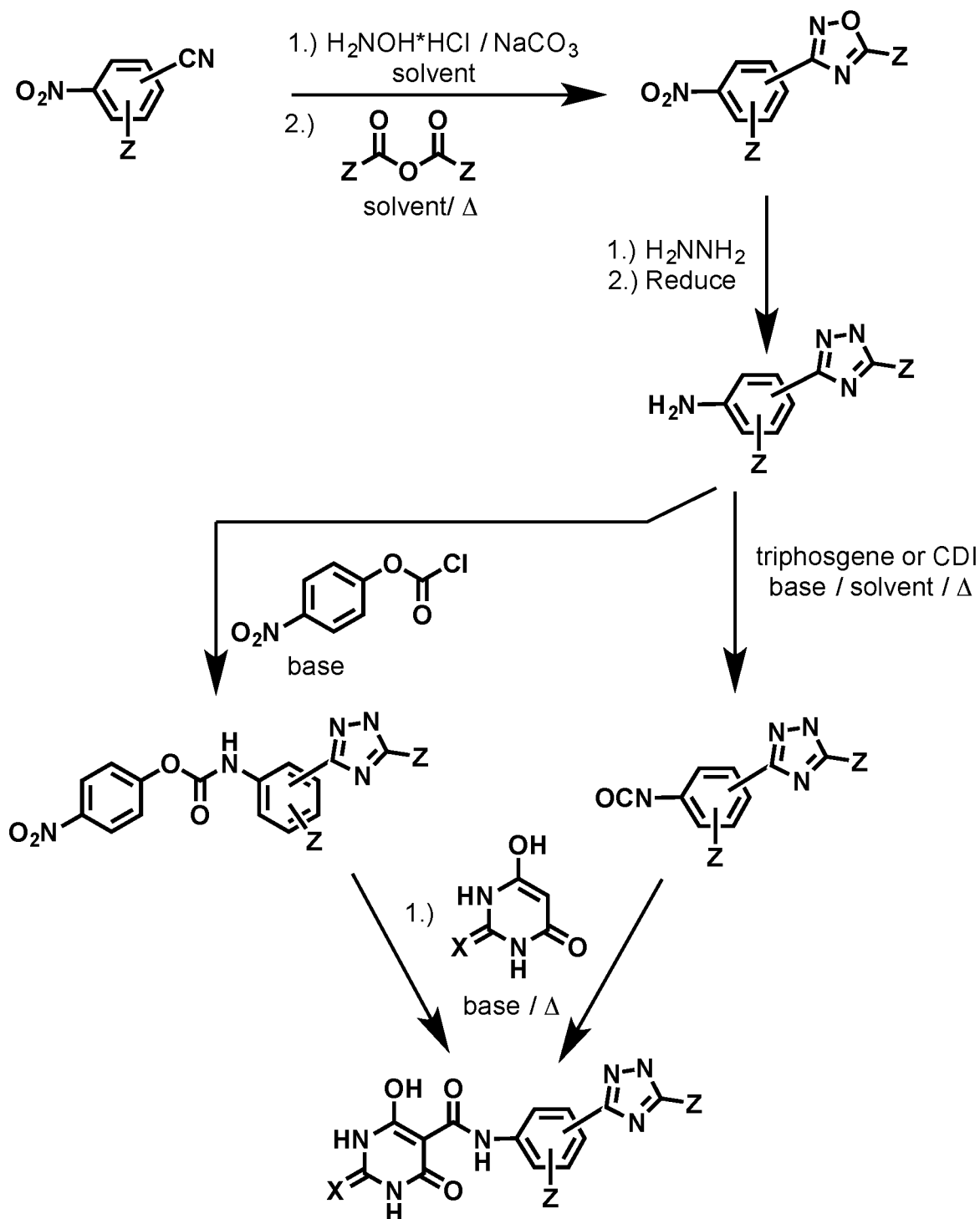
FIG. 7 illustrates an alternative general synthesis scheme for preparation of certain compounds having a structure represented by Formula (I), wherein the 5-member ring is a 2,3,5-triazole.

In general, the various synthetic routes available for preparing the above compounds center on coupling of the phenyl heterocyclic ring with a barbiturate ring. Several coupling reagents are depicted in FIGS. 1-7 to accomplish this, for example triphosgene, carbonyl diimidazole (CDI), or 4-nitrophenyl chloroformate. Depending on the nature of the substituents the preceding steps can vary. FIG. 1 depicts the direct conversion of the substituted amino phenyl moiety already substituted with the appropriate heterocycle. In certain cases the amino group may not be commercially available, so the corresponding nitro compound must be converted via reduction to the amine, using methods known in the art. Protecting groups on the heterocyclic ring may or may not be necessary. FIG. 2 depicts how to form the triazole heterocyclic ring when-necessary. Addition of azide to either the nitro or amino aryl ring moiety can be accomplished via a variety of methods which all involve the addition of azide to the acetylene. In some cases a substituted aromatic acetylene may be novel or not commercially available. In such cases, it must be synthesized as depicted in FIG. 3. In such cases one skilled in the art would typically utilize the Sonogashira reaction to introduce the acetylene onto a halide substituted aromatic system. Ideally, this aromatic system would contain the nitro or amino groups already in place. Following introduction of the acetylene group, azides would be reacted with the acetylene, as discussed above. In some cases, the acetylene would need to be protected prior to the Sonogashira reaction, as depicted in FIG. 4. The protecting group is usually a TMS group, and it can be removed prior to the coupling reaction to the appropriate barbiturate ring. The heterocyclic ring attached to the phenyl ring can also be introduced subsequent to the coupling of the barbiturate ring with the phenyl ring. Such an example is depicted in FIG. 5. The substitution and configuration of the introduced heterocycle can be altered by known methods in the literature, so as to provide different heterocycles attached to the phenyl ring. FIG. 6 depicts an alternative to the Sonogashira reaction to introduce the heterocyclic ring system onto the phenyl ring. It involves a Suziku coupling, or a variation thereof, between a boron containing aromatic ring and an appropriately substituted heterocyclic halide. The reverse situation where the heterocycle contains the boron moiety and the aromatic system contains the halide can also be envisioned. As depicted in earlier figures, protecting groups may be required, but these would be apparent to one skilled in the art. Other heterocycles like the ones depicted in FIG. 7 may be made from the appropriately substituted aromatic nitrile. As in the case with other synthetic sequences, the use of protecting groups may be necessary.

In a further aspect, the invention provides methods for reducing uric acid levels in the blood or serum of a subject comprising administering a compound having a structure represented by Formula (I), or a combination thereof, to the subject in an amount effective to reduce blood or serum uric acid levels. It is to be understood that all such methods for reducing uric acid levels correspond to a compound having a structure represented by Formula (I), or a combination thereof, for use in medicine as well as a compound having a structure represented by Formula (I), or a combination thereof, for use in the treatment of elevated uric acid levels. Typically, the compound having a structure represented by Formula (I), or a combination thereof, will be administered when the level of uric acid in the blood of the subject is elevated, i.e., in the upper range of normal or above normal levels. One skilled in the art would further recognize that continued administration after normal uric acid levels are achieved is also contemplated in order to maintain uric acid levels within the normal range and to reduce the overall body burden of uric acid that may have occurred due to previously sustained hyperuricemia. Accordingly, methods for preventing elevation of uric acid levels in blood or serum are also an aspect of the invention. It is to be understood that all such methods for preventing elevation of uric acid levels correspond to a compound having a structure represented by Formula (I), or a combination thereof, for therapeutic use as well as a compound having a structure represented by Formula (I), or a combination thereof, for prevention of elevated uric acid levels.

Normal uric acid levels in blood are generally in the range of 4.3 mg/dL to 8.0 mg/dL. In certain embodiments, a compound having a structure represented by Formula (I), or a combination thereof, is administered to a subject with a blood uric acid level of at least about 6 mg/dL. Administration may continue until a blood uric acid level of about 6.0 mg/dL or less is reached; however, it is generally considered to be beneficial to maintain uric acid levels below this target in patients with disorders of uric acid metabolism.

In certain embodiments, methods of treating a disorder of uric acid metabolism caused by, or associated with, elevated uric acid levels in blood or serum (hyperuricemia) are provided. The method of treating such disorders comprises administering a compound having a structure represented by Formula (I), or a combination thereof, to a subject in need thereof in an amount effective to reduce serum uric acid levels, thereby treating the disorder of uric acid metabolism in the subject. These disorders are associated with, or caused by, elevated uric acid levels in blood or serum which are in the upper range of normal or above normal, and include gout, hyperuricemia, kidney disease, arthritis, kidney stones, kidney failure, urolithiasis, plumbism, hyperparathyroidism, psoriasis, inborn genetic errors of metabolism (including but not limited to Lesch-Nyhan syndrome), sarcoidosis, cardiovascular disease) including but not limited to atherosclerosis) and disorders of uric acid metabolism associated with transplantation of blood, bone marrow or solid organs. These drugs are particularly useful for treating gout and kidney disease (including acute uric acid nephropathy, chronic urate nephropathy, and uric acid nephrolithiasis). In addition, treatment of some cancers with chemotherapy leads to the release of large amounts of uric acid into the blood, which can damage the kidneys. Chemotherapy-induced hyperuricemia, particularly the disorder known as "tumor lysis syndrome," may also be treated, prevented or ameliorated according to the methods of the invention. Administration of a compound having a structure represented by Formula (I), or a combination thereof, to a subject with hyperuricemia, such as a subject suffering from gout, kidney disease, or a risk of inducing elevated uric acid levels due to chemotherapy, treats, prevents or ameliorates these disorders by reducing uric acid levels in blood, or preventing or controlling their level of increase. In specific embodiments, the disorder of uric acid metabolism treated by administration of a compound having a structure represented by Formula (I), a combination thereof, is gout. It is to be understood that all such methods for treating disorders of uric acid metabolism caused by, or associated with, elevated uric acid levels in blood or serum (hyperuricemia) correspond to a compound having a structure represented by Formula (I), or a combination thereof, for therapeutic use as well as a compound having a structure represented by Formula (I), or a combination thereof, for treatment of disorders of uric acid metabolism caused by, or associated with, elevated uric acid levels in blood or serum.

The dose of a compound having a structure represented by Formula (I), or a combination thereof, administered to the subject may be any dose sufficient to achieve a desired reduction in uric acid levels in blood or serum over the time-course of administration. In certain embodiments, a daily dose of about 20 to about 1,500 mg/m$^2$/day is administered. In other embodiments, a daily dose of about 20 to about 500 mg/m$^2$/day, about 20 to about 250 mg/m$^2$/day, about 20 to about 150 mg/m$^2$/day or about 20 to about 100 mg/m$^2$/day is administered. In other embodiments, a daily dose of about 50 to about 1,500 mg/m$^2$/day is administered. In other embodiments, a daily dose of about 50 to about 500 mg/m$^2$/day, about 50 to about 150 mg/m$^2$/day, about 50 to about 100 mg/m$^2$/day, or about 20 to about 100 mg/m$^2$/day is administered.

In certain embodiments of any of the foregoing methods, a compound having a structure represented by Formula (I), or a combination thereof, is administered to the subject parenterally, intraperitoneally, intravenously, intranasally, intrarectally, or orally. Particularly useful routes of administration include injection, infusion, or oral administration. The amount of the drug administered per dose is an amount sufficient to achieve a reduction in uric acid levels in blood or serum, to prevent elevation of uric acid levels in blood or serum, or to treat or prevent a disorder of uric acid metabolism over the course of therapy. One skilled in the art will recognize that individualization of dosage based on a patient's body composition or his/her hypouricemic response to treatment may be medically necessary or desirable.

The drug(s) may be administered to the subject either intermittently or continuously over a period of time in order to achieve the desired reduction in uric acid levels in blood or serum, or to treat a disorder of uric acid metabolism. For example, doses may be administered intermittently several times per day, or daily, once, twice or three times per week, or at monthly intervals. In a specific example, a compound having a structure represented by Formula (I), or a combination thereof, may be administered to the subject by continuous intravenous infusion over 24 hours for about five days. Alternatively, a compound having a structure represented by Formula (I), or a combination thereof, may be administered to the subject by intravenous infusion over about 1 hour to about 5 hours for about five consecutive days. In a specific example, a compound having a structure represented by Formula (I), or a combination thereof, may be administered to the subject by intramuscular injection or by intravenous infusion over about 10 minutes for about five consecutive days. In further specific embodiments, a compound having a structure represented by Formula (I), or a combination thereof, may be administered to the subject by daily bolus injections for about five days. The period of time of administration in any of the foregoing protocols may be modified to achieve the desired reduction in uric acid levels, including about 2 days, about 3 days, about 4 days, about one week or about two weeks of administration, or for longer periods in repeated treatment cycles, and these treatments may be repeated at intervals of every two to every 10 weeks.

In addition to continuous intravenous infusion or bolus intravenous or subcutaneous injection, a compound having a structure represented by Formula (I), or a combination thereof, may be administered to the subject orally. In this embodiment, an oral dose in amounts as described above may be administered in one, two, three or four administrations per day for 1, 2, 3, 4, or 5 days to achieve the desired reduction in uric acid levels. In further embodiments, the oral dose as described above may be administered once per day, or in one, two, three or four administrations per day for one week or two weeks, to achieve the desired reduction in uric acid levels.

It will be appreciated that a subject in need of reduced levels of uric acid in blood or serum, or in need of treatment of a disorder of uric acid metabolism, will be treated more aggressively initially to achieve the desired reduction in uric acid levels. Following initial therapy and reduction of uric acid levels to normal or sub-normal levels, the subject may be further treated over a period of time, or over a lifetime, to maintain normal or sub-normal levels of uric acid in blood or serum and prevent elevation of uric acid levels subsequent to the initial treatment. The maintenance or preventive protocol may comprise reduced dosages and/or less frequent administration of a compound having a structure represented by Formula (I), or a combination thereof, as necessary or desired to maintain normal or sub-normal uric acid levels in blood or serum. For example, in a maintenance protocol the drug(s) may be administered daily, weekly, monthly, or intermittently as uric acid levels rise between treatment periods. Such maintenance protocols will serve to maintain normal or sub-normal uric acid levels for a prolonged period of time and reduce the subject's lifetime risk of developing a disorder of uric acid metabolism caused by, or associated with, prolonged hyperuricemia. The initial reduction of uric acid levels from above normal or high normal to normal or sub-normal, and maintenance of normal or sub-normal uric acid levels are both features included in treatment of a disorder of uric acid metabolism. It is anticipated that in certain embodiments, a typical patient will require daily treatment of varying duration, and that such daily treatment may be provided intermittently for life or for extended periods.

In certain embodiments of any of the foregoing methods, blood or serum uric acid levels of the subject are reduced by at least 25% compared to uric acid levels prior to administration of a compound having a structure represented by Formula (I), or a combination thereof. In certain further embodiments, blood or serum uric acid levels of the subject are reduced by 50% or more compared to levels prior to administration. In a specific embodiment, uric acid levels are reduced by about 75% even at daily doses of 500 mg/m$^2$/day or less.

In a second aspect, methods are provided for treating a disorder of uric acid metabolism associated with, or caused by, elevated uric acid in blood or serum comprising administering to a subject in need thereof a compound having a structure represented by Formula (I), or a combination thereof, in an amount effective to reduce blood or serum uric acid levels, thereby treating the disorder of uric acid metabolism. Specific embodiments of the methods for treating a disorder of uric acid metabolism relating to dosing, routes of administration, initial therapy and maintenance therapy are as described above for reducing uric acid levels in blood or serum. The initial reduction in uric acid levels is typically rapid, and often occurs within 1-3 days. Upon reduction in uric acid levels to normal or sub-normal levels, continued maintenance or preventive therapy results in a detectable improvement in at least one symptom of elevated uric acid, for example reduced inflammation, reduced pain, slowing of development of deformities, reduced development of kidney stones, prevention of tumor lysis syndrome, stabilization in cognition or other manifestations of inborn metabolic disorders, or improvement in or reduction of actual or risk for cardiovascular disease. One skilled in the art will recognize that prevention of recurrent symptoms of disease due to recurrence of elevated serum uric acid levels, thereby necessitating extended treatment, would be highly desirable to maximize patient benefit.

In embodiments corresponding to the foregoing methods, the invention relates to use of a compound disclosed herein, or a combination thereof, for reducing uric acid levels in blood or serum of a subject in need thereof, preventing elevation of uric acid levels in blood or serum of a subject, or treating a disorder of uric acid metabolism caused by, or associated with, hyperuricemia. Each of the methods of treatment or prevention disclosed, including routes of administration, dosage and compounds administered, are also applicable to such uses of the compounds.

A further aspect of the invention provides a pharmaceutical composition comprising a compound having a structure represented by Formula (I), or a combination thereof, and a pharmaceutically acceptable carrier. In certain embodiments of the pharmaceutical compositions, the composition is formulated as a solution or tablet. Solutions or dispersions of the drug(s) can be prepared in water or saline. In certain embodiments of the pharmaceutical compositions, the pharmaceutically acceptable carrier is one or more component selected from the group consisting of one or more of a solvent, a dispersing agent, a coating (e.g., lecithin), a surfactant (e.g., hydroxypropylcellulose), a preservative (e.g., paraben, phenol, thimerosal, sorbic acid, chlorobutanol), an emulsion, an alcohol (e.g., ethanol), a polyol (e.g., glycerol, propylene glycol), and an isotonic agent (e.g., sugars, sodium chloride).

In certain embodiments of the foregoing pharmaceutical compositions, the composition is formulated for controlled release of the compound having a structure represented by Formula (I), or a combination thereof. In certain embodiments of the foregoing methods, a compound having a structure represented by Formula (I), or a combination thereof, is administered in a form for controlled release. The controlled release compositions may include pharmaceutically acceptable carriers or excipients which cause release of the active ingredient more slowly or which extend the duration of its action within the body. Examples of controlled release compositions include pharmaceutically acceptable carriers or excipients which delay absorption of the active ingredient (e.g., aluminum monostearate, gelatin, natural or synthetic hydrophilic gums). Alternatively, controlled release of the pharmaceutical composition may employ a device such as a pump, implant or transdermal patch.

In certain embodiments of the foregoing pharmaceutical compositions, the composition is formulated for improved oral bioavailability or extended release in the body. For example, microemulsions, particle size reduction and complexation technologies may be used to improve dissolution rates or equilibrium solubilities of the compounds. Other suitable chemical and physical means for improving oral bioavailability or extended release will also be known to those skilled in the art.

EXAMPLES

General Procedure for CDI coupling: To a stirring solution of amine (1 eq) in anhydrous DMSO (1.0 M) was added 1,1'carbonyldiimidazole (1.5 eq) was added at rt, under inert atmosphere. The resulting solution was stirred for 20 min at rt. In a separate flask containing barbituric acid (1 eq) was added anhydrous 1,4-dioxane (0.30 M), then heated to 55° C. Et$_3$N (1.6 eq) was added and stirred for 15 min at 55° C. The isocyanate generated from the amine in DMSO was added to the stirring suspension, then heated to 80° C. until complete consumption of the starting materials were observed via LCMS (1-20 h). The reaction mixture was cooled to rt, then acidified with 6M HCl (aq), the precipitate formed was isolated, then triturated with water, MeOH, followed by acetonitrile.

Figure 8:
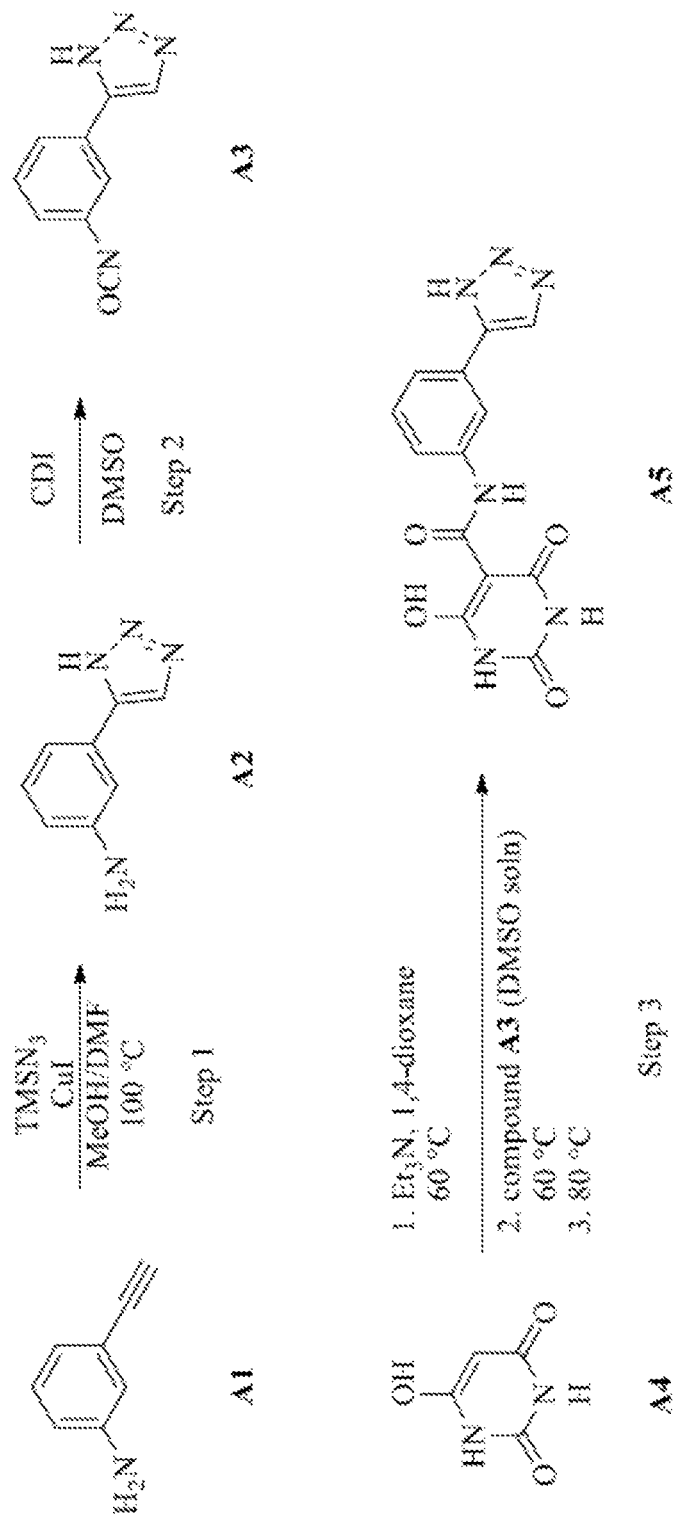
FIG. 8 illustrates a general synthesis scheme for preparation of a compound having a structure represented by Formula (I$_a$).

Example 1: Preparation of N-(3-(1H-1,2,3-triazol-5-yl)phenyl)-6-hydroxy-2,4-dioxo-1,2,3,4-tetrahydropyrimidine-5-carboxamide (A5, Formula (I$_a$), with reference to the synthesis scheme illustrated in FIG. 8)

Step One. 3-(1H-1,2,3-Triazol-5-yl)aniline (A2). To a stirred solution of A1 (1.00 g, 8.53 mmol) in N,N-dimethylformamide/methanol (9:1, 15 mL), under a nitrogen atmosphere, was added copper (I) iodide (81 mg, 0.43 mmol) and trimethylsilyl azide (1.70 mL, 12.8 mmol). The resulting suspension was heated to 100° C. for 15 h. After this time, the reaction mixture was cooled to ambient temperature and diluted with ethyl acetate (50 mL). The solids were removed by vacuum filtration and the filtrate was concentrated under reduced pressure. The resulting brown oil was purified by flash column chromatography on silica gel eluting with 0-50% CMA (88.5:10:1.5 chloroform/methanol/concentrated ammonium hydroxide)/methylene chloride to afford compound A2 (872 mg, 64%) as a light yellow solid: $^1$H NMR (300 MHz, CD$_3$OD) δ8.04 (br s, 1H), 7.21-7.07 (m, 3H), 6.73-6.69 (m, 1H); Multimode MS m/z 159 [M–H]$^-$.

Steps Two and Three. N-(3-(1H-1,2,3-Triazol-5-yl)phenyl)-6-hydroxy-2,4-dioxo-1,2,3,4-tetrahydropyrimidine-5-carboxamide (A5). To a stirred solution of 1,1'-carbonyldiimidazole (251 mg, 1.55 mmol) and imidazole (11 mg, 0.16 mmol) in DMSO (1.5 mL), under a nitrogen atmosphere, was added compound A2 (248 mg, 1.55 mmol) in anhydrous DMSO (1.5 mL) dropwise over 5 min. The reaction mixture was stirred at ambient temperature for 65 min to provide a solution of compound A3 in DMSO which was used directly in the subsequent step.

In a separate flask, to a suspension of 6-hydroxypyrimidine-2,4(1H,3H)-dione A4 (198 mg, 1.55 mmol) in anhydrous 1,4-dioxane (6 mL), at 60° C. and under a nitrogen atmosphere, was added triethylamine (0.22 mL, 1.55 mmol). After the addition was complete the mixture was stirred for 5-10 min. To this mixture was then added the solution of compound A3 in DMSO dropwise over 5 min. The resulting yellow solution was heated to 80° C. overnight. After this time, the orange-brown reaction solution was cooled to ambient temperature and concentrated under reduced pressure to remove the majority of the 1,4-dioxane. To the reaction residue was added 0.5 N HCl (50 mL) and the mixture was heated to 75° C. The resulting solid was collected by filtration while the reaction mixture was still hot. The solid (~390 mg) was suspended in acetonitrile (20 mL) and heated to reflux for 30 minutes. The solid was collected by vacuum filtration while the suspension was still hot. The solid was resuspended in 0.5 M HCl (~40 mL) and the reaction suspension heated to 80° C. for 2.5 h. The solid present was collected by filtration while the reaction mixture was still hot.

The solid (~360 mg) obtained was suspended in CMA (80:18:2 chloroform/methanol/concentrated ammonium hydroxide), then stirred, sonicated, and filtered. This procedure was repeated twice more. The filter cake was suspended in 35% methanol/methylene chloride (20 mL), then stirred, sonicated, and filtered. The solid was resuspended in water (~20 mL) and heated to 70° C. for 1 hour. The resulting gelatinous reaction mixture was collected by filtration and dried overnight under vacuum. The solid was resuspended in 0.5 N HCl (~15 mL), heated to 70° C. for 1.5 h, then removed and filtered while still hot. The resulting solid was dried overnight under high vacuum at 40° C. The solid (~220 mg) was then suspended in 1,4-dioxane (30 mL), heated to 75° C. for 2 hours, and filtered while still hot. The collected solid (~170 mg) was resuspended in 1,4-dioxane (45 mL), heated to 80° C. for 30 min, then filtered hot. The filter cake was dried in vacuo at 40° C. to afford A5 (111 mg) as a light brown solid: $^1$H NMR (500 MHz, DMSO-d$_6$, mixture of tautomers) δ 15.37 (br s, ~0.35H), 15.01 (s, ~0.65H), 12.05 (br s, 1H), 11.61 (s, 1H), 11.35 (br s, 1H), 8.57 (br s, ~0.35H), 8.29 (s, ~0.65H), 8.03 (s, 1H), 7.60-7.45 (m, 2H), 7.50 (d, J=7.5 Hz, 1H), phenol proton not observed by $^1$H NMR; Multimode MS m/z 313 [M–H]$^-$.

Figure 9:
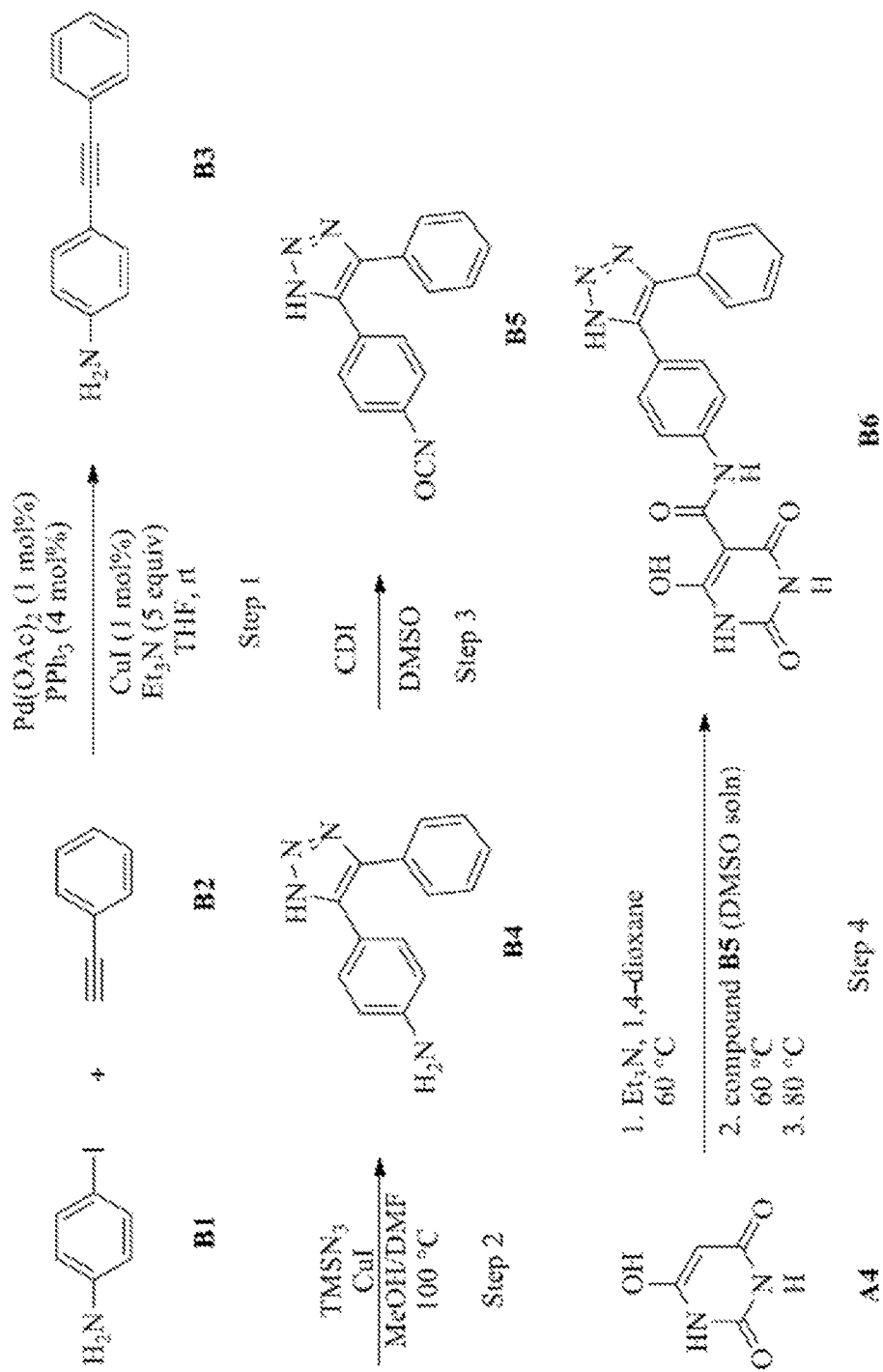
FIG. 9 illustrates a general synthesis scheme for preparation of a compound having a structure represented by Formula (I$_c$).

Example 2: Preparation of 6-hydroxy-2,4-dioxo-N-(4-(4-phenyl-1H-1,2,3-triazol-5-yl)phenyl)-1,2,3,4-tetrahydropyrimidine-5-carboxamide (B6, Formula (I$_c$), with Reference to the Synthesis Scheme Illustrated in FIG. 9)

Step One. 4-(Phenylethynyl)aniline (B3). To a round-bottomed flask was added palladium (II) acetate (10 mg, 0.046 mmol), triphenylphosphine (48 mg, 0.183 mmol), copper (I) iodide (9 mg, 0.046 mmol), 4-iodoaniline (B1, 1.00 g, 4.57 mmol) and THF (12 mL). After bubbling nitrogen through the reaction mixture for 5 min, phenylacetylene (B2, 559 mg, 5.48 mmol) and triethylamine (2.31 g, 22.9 mmol) were added sequentially. The reaction mixture was stirred at room temperature overnight. After diluting with diethyl ether (~100 mL), the mixture was washed with saturated aqueous ammonium chloride (25 mL), water (25 mL), and brine (25 mL). The organic layer was dried over MgSO$_4$, filtered, and concentrated under reduced pressure.

The resulting residue was purified by flash column chromatography on silica gel eluting with 0-20% ethyl acetate/hexanes to afford compound B3 (770 mg, 87%) as a yellow-orange solid: $^1$H NMR (300 MHz, CDCl$_3$) δ7.52-7.46 (m, 2H), 7.37-7.26 (m, 5H), 6.66-6.61 (m, 2H), 3.81 (br s, 2H); Multimode MS m/z 194 [M+H]$^+$.

Step Two. 4-(4-Phenyl-1H-1,2,3-triazol-5-yl)aniline (B4). To a stirred solution of B3 (440 mg, 2.28 mmol) in N,N-dimethylformamide/methanol (9:1, 5 mL), under a nitrogen atmosphere, was added copper (I) iodide (22 mg, 0.11 mmol) and trimethylsilyl azide (0.45 mL, 3.42 mmol). The resulting suspension was heated to 100° C. for 15 h. After this time, the reaction mixture was cooled to ambient temperature and diluted with ethyl acetate (150 mL). The solids were removed by filtration through Celite® and the filtrate was concentrated under reduced pressure. The reaction residue was purified by flash column chromatography on silica gel eluting with 10-45% ethyl acetate/hexanes to afford compound B4 (200 mg, 37%) as a yellow oil: $^1$H NMR (500 MHz, CDCl$_3$) δ11.50 (br s, 1H), 7.63-7.58 (m, 2H), 7.41-7.32 (m, 5H), 6.71-6.66 (m, 2H), 3.79 (br s, 2H); Multimode MS m/z 237 [M+H]$^+$.

Steps Three and Four. 6-Hydroxy-2,4-dioxo-N-(4-(4-phenyl-1H-1,2,3-triazol-5-yl)phenyl)-1,2,3,4-tetrahydropyrimidine-5-carboxamide (B6). To a stirred solution of 1,1'-carbonyldiimidazole (265 mg, 1.31 mmol) and imidazole (9 mg, 0.13 mmol) in DMSO (1.5 mL), under a nitrogen atmosphere, was added compound B4 (310 mg, 1.31 mmol) in anhydrous DMSO (1.5 mL) dropwise over 5 min. The reaction mixture was stirred at ambient temperature for 40 min to provide a solution of compound B5 in DMSO which was used directly in the subsequent step.

In a separate flask, to a suspension of 6-hydroxypyrimidine-2,4(1H,3H)-dione A4 (168 mg, 1.31 mmol) in anhydrous 1,4-dioxane (5 mL), at 60° C. and under a nitrogen atmosphere, was added triethylamine (0.18 mL, 1.31 mmol). After the addition was complete the mixture was stirred for ~60 min. To this mixture was then added the solution of compound B5 in DMSO dropwise over 5 min. The resulting yellow solution was heated to 80° C. for 2.5 h. After this time, the brown reaction solution was cooled to ambient temperature, water (3 mL) was added, and the mixture was concentrated under reduced pressure to remove the majority of the 1,4-dioxane. To the reaction residue was added 0.5 N HCl (50 mL) and the mixture was heated to 75° C. for 1 h. The resulting solid was collected by filtration while the reaction mixture was still hot. The red-brown solid (~480 mg) was suspended in acetonitrile (25 mL) and heated to reflux for 30 minutes. The solid was collected by vacuum filtration while the suspension was still hot. The filter cake (~315 mg) was resuspended in 1,4-dioxane (30 mL) and the reaction suspension heated to 75° C. for 30 min, then the oil bath temperature was reduced to 55° C. for 30 minutes and the reaction mixture was filtered hot. The fitrate was diluted with acetonitrile (~90 mL) and filtered. The resulting filtrate was concentrated under reduced pressure. The solid obtained was resuspended in 85:15 methylene chloride/methanol (35 mL), stirred for 20 minutes, and the supernatent was decanted. The remaining solid was dried under high vacuum to afford B6 (207 mg) as a light brown solid: $^1$H NMR (500 MHz, DMSO-d$_6$, mixture of tautomers) δ15.55 (br s, ~0.30H), 15.15-15.07 (m, ~0.70H), 12.08 (br s, 1H), 11.60 (s, 1H), 11.42 (br s, 1H), 7.70-7.25 (m, 10H); Multimode MS m/z 389 [M−H]$^−$.

Figure 10:
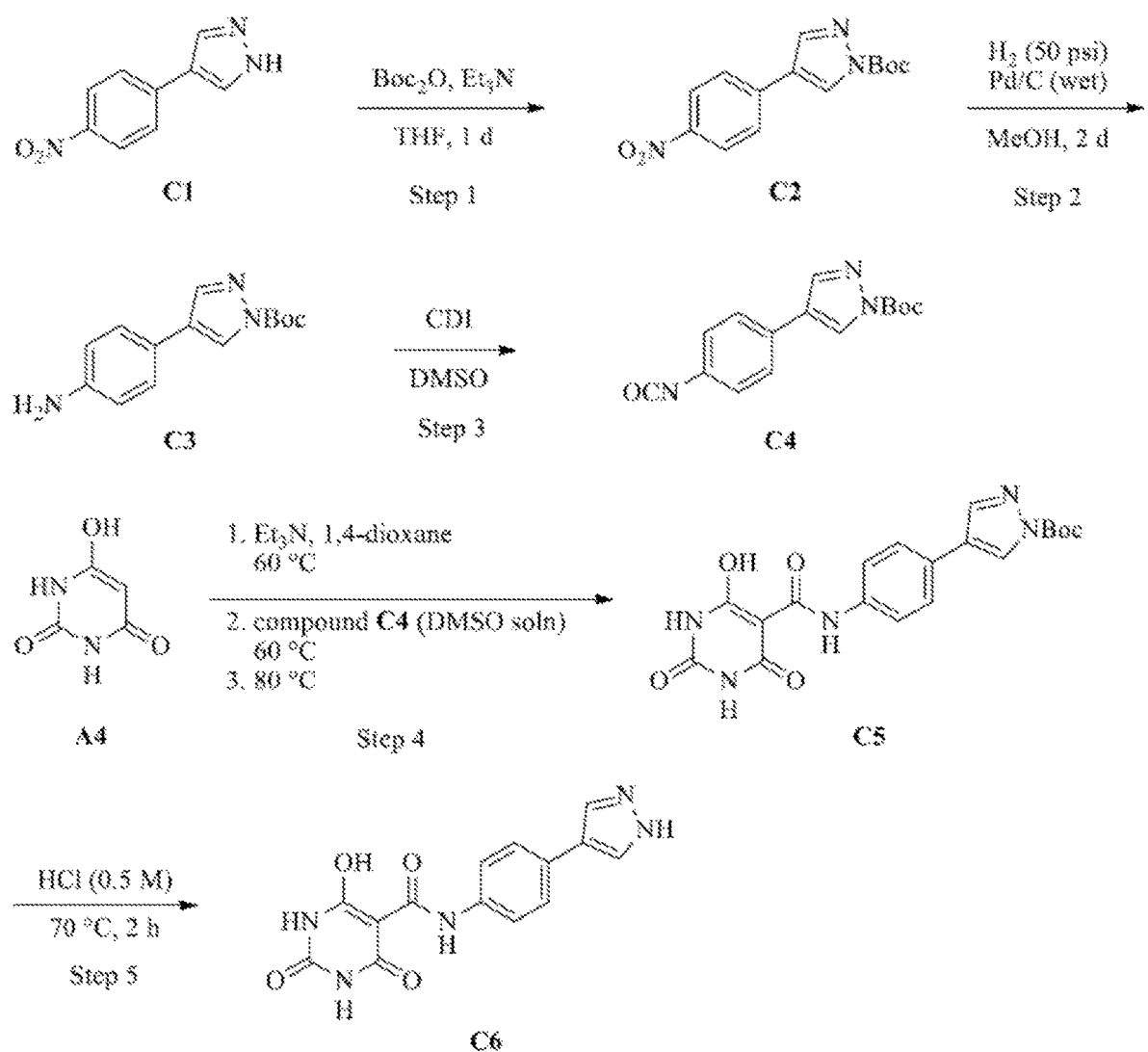
FIG. 10 illustrates a general synthesis scheme for preparation of a compound having a structure represented by Formula (I$_f$).

Example 3: Preparation of N-(4-(1H-pyrazol-4-yl)phenyl)-6-hydroxy-2,4-dioxo-1,2,3,4-tetrahydropyrimidine-5-carboxamide (C6, Formula (I$_f$), with Reference to the synthesis scheme illustrated in FIG. 10)

Step One. tert-Butyl 4-(4-nitrophenyl)-1H-pyrazole-1-carboxylate (C2). To a solution of 4-(4-nitrophenyl)-1H-pyrazole (C1, 1.01 g, 5.34 mmol) in THF (35 mL) at room temperature was added triethylamine (1.86 mL, 13.4 mmol), followed by di-tert-butyl dicarbonate (1.46 g, 6.67 mmol). After stirring for 18 h, additional di-tert-butyl dicarbonate (580 mg, 2.67 mmol) and 4-dimethylaminopyridine (33 mg, 0.27 mmol) were added. After stirring at room temperature for an additional 18 h, the reaction mixture was concentrated in vacuo, diluted with ethyl acetate (150 mL), and washed with water (35 mL) and brine (35 mL). The organic layer was dried over MgSO$_4$, filtered, and concentrated under reduced pressure. The resulting residue (~1.6 g) was purified by flash column chromatography on silica gel eluting with 5-35% ethyl acetate/hexanes to afford compound C2 (1.03 g, 67%) as a yellow-orange solid: $^1$H NMR (300 MHz, CDCl$_3$) δ8.44 (s, 1H), 8.27 (d, J=8.7 Hz, 2H), 8.06 (s, 1H), 7.68 (d, J=8.7 Hz, 2H), 1.70 (s, 9H).

Step Two. tert-Butyl 4-(4-aminophenyl)-1H-pyrazole-1-carboxylate (C3). To a nitrogen purged solution of C2 (530 mg, 1.83 mmol) in methanol (75 mL) was added palladium on carbon (wet; 10% by weight, 105 mg) and the resulting suspension was purged with nitrogen for an additional 5 min. Using a Parr apparatus, the reaction was kept under to a hydrogen atmosphere (50 psi) for 2 d. The reaction mixture was filtered through Celite®, washing with ethyl acetate (~150 mL). The filtrate was then concentrated under reduced pressure and the resulting reaction residue was purified by flash column chromatography on silica gel eluting with 10-40% ethyl acetate/hexanes to afford compound C3 (347 mg, 73%) as a white solid: $^1$H NMR (300 MHz, CDCl$_3$) δ8.18 (d, J=0.6 Hz, 1H), 7.91 (d, J=0.6 Hz, 1H), 7.35-7.30 (m, 2H), 6.73-6.69 (m, 2H), 4.10-3.30 (br s, 2H), 1.67 (s, 9H); ESI MS m/z 260 [M+H]$^+$.

Steps Three and Four. tert-Butyl 4-(4-(6-hydroxy-2,4-dioxo-1,2,3,4-tetrahydropyrimidine-5-carboxamido)phenyl)-1H-pyrazole-1-carboxylate (C5). To a stirred solution of 1,1'-carbonyldiimidazole (304 mg, 1.87 mmol) and imidazole (9 mg, 0.13 mmol) in DMSO (1.0 mL), under a nitrogen atmosphere, was added compound C3 (347 mg, 1.34 mmol) in anhydrous DMSO (2.0 mL) dropwise over 7 min. The reaction mixture was stirred at ambient temperature for 20 min to provide a solution of compound C4 in DMSO which was used directly in the subsequent step.

In a separate flask, to a suspension of 6-hydroxypyrimidine-2,4(1H,3H)-dione A4 (172 mg, 1.34 mmol) in anhydrous 1,4-dioxane (6 mL), at 60° C. and under a nitrogen atmosphere, was added triethylamine (0.19 mL, 1.34 mmol). After the addition was complete the mixture was stirred for ~10 min. To this mixture was then added the solution of compound C4 in DMSO dropwise over 5 min. The resulting yellow solution was heated to 80° C. for 3 h. After this time, the reaction mixture was cooled to ambient temperature, water (2 mL) was added, and the mixture was concentrated under reduced pressure to remove the majority of the 1,4-dioxane. Water was added (40 mL) and the resulting solid was collected by filtration. After drying for 2 d under high vacuum, the beige solid was resuspended in acetonitrile (50 mL) and heated to 65° C. for 45 minutes. The solid was collected by vacuum filtration while the suspension was still hot. The collected solid (~185 mg) was resuspended in 85:15 methylene chloride/methanol (20 mL), stirred for 15 minutes and the supernatent was decanted. The remaining solid (~115 mg) was resuspended in 1,4-dioxane (20 mL), heated to 55° C. for 20 min, then filtered to afford C5 (110 mg; ~90% purity by $^1$H NMR) as an off-white light solid: $^1$H NMR (500 MHz, DMSO-d$_6$) δ12.10 (br s, 1H), 11.59 (s, 1H), 11.30 (br s, 1H), 8.72 (s, 1H), 8.30 (s, 1H), 7.78 (d, J=8.7 Hz, 2H), 7.57 (d, J=8.7 Hz, 2H), 1.61 (s, 9H), phenol proton not observed by $^1$H NMR; ESI MS m/z 412 [M–H]$^-$.

Step Five. N-(4-(1H-Pyrazol-4-yl)phenyl)-6-hydroxy-2,4-dioxo-1,2,3,4-tetrahydropyrimidine-5-carboxamide (C6). A stirred suspension of C5 (35 mg, 0.085 mmol) in 0.5 M aqueous HCl (5 mL) was heated to 70° C. for 2.5 h. The resulting solid was collected by filtration while the solution was still hot. This collected solid was resuspended in 0.5 M HCl (4 mL) and 1,4-dioxane (1 mL) and heated to 70° C. for 5 hours. The solid was again collected by filtration while the reaction mixture was still hot and dried overnight under high vacuum to afford C6 (18.5 mg, 68%) as an off-white solid: $^1$H NMR (500 MHz, DMSO-d$_6$) δ12.95 (br s, 1H), 12.05 (br s, 1H), 11.52 (s, 1H), 11.34 (br s, 1H), 8.05 (br s, 2H), 7.63 (d, J=8.7 Hz, 2H), 7.51 (d, J=8.7 Hz, 2H), phenol proton not observed by $^1$H NMR; ESI MS m/z 312 [M–H]$^-$.

Figure 11:
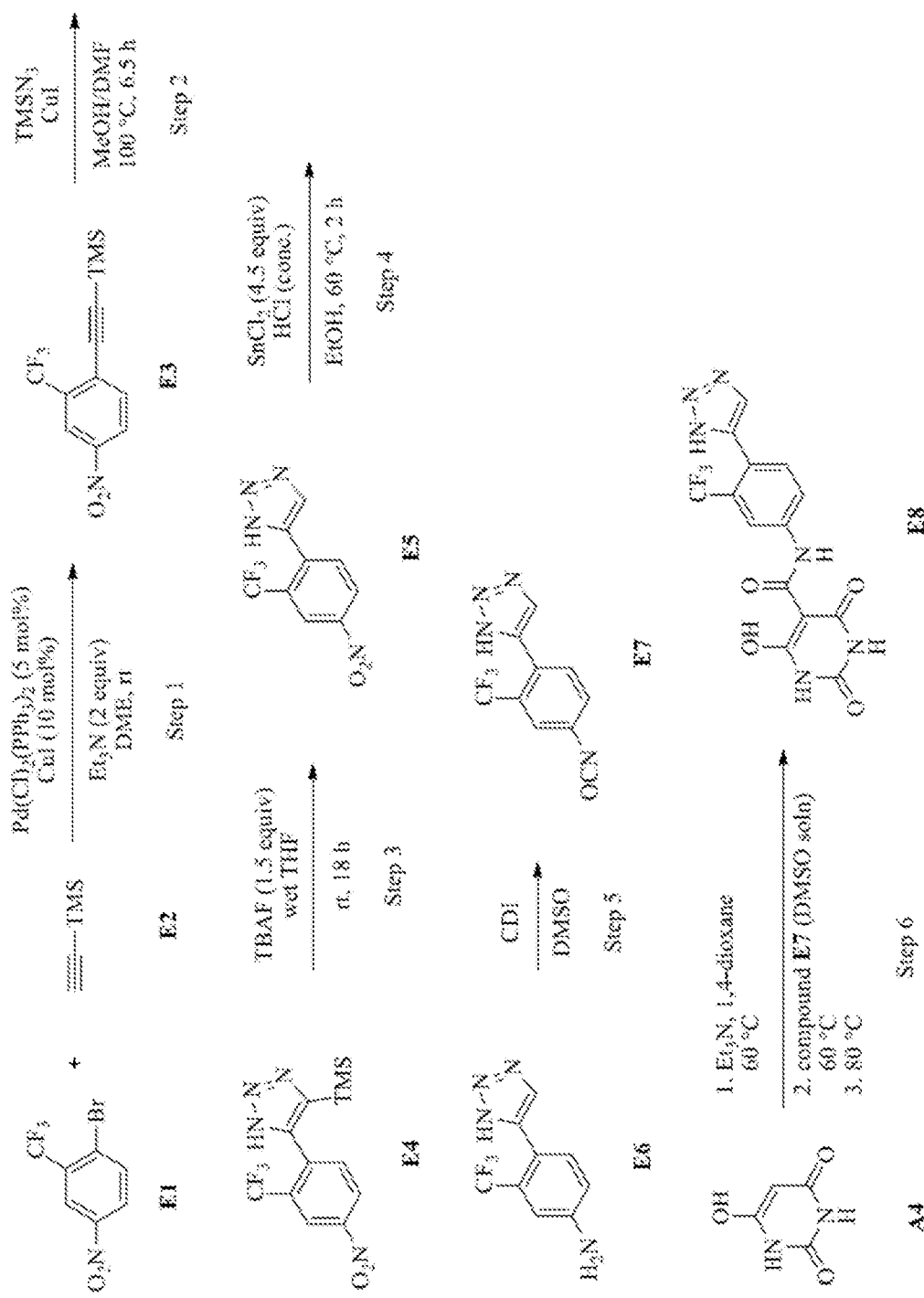
FIG. 11 illustrates a general synthesis scheme for preparation of a compound having a structure represented by Formula (I$_g$).

Example 4: Preparation of N-(4-(1H-1,2,3-triazol-5-yl)-3-(trifluoromethyl)phenyl)-6-hydroxy-2,4-dioxo-1,2,3,4-tetrahydropyrimidine-5-carboxamide (E8, Formula (I$_g$), with Reference to the Synthesis Scheme Illustrated in FIG. 11)

Step One. Trimethyl((4-nitro-2-(trifluoromethyl)phenyl)ethynyl)silane (E3). To a round-bottomed flask was added 2-bromo-5-nitrobenzotrifluoride (E1, 2.00 g, 7.40 mmol), dimethoxyethane (20 mL), copper (I) iodide (141 mg, 0.740 mmol), and triethylamine (2.06 mL, 14.8 mmol). After bubbling nitrogen through the reaction mixture for 5 minutes, trans-dichlorobis(triphenylphosphine) palladium (II) (260 mg, 0.370 mmol) and ethynyltrimethylsilane (E2, 1.57 mL, 11.1 mmol) were added sequentially and the reaction stirred at room temperature overnight (~18 h). The reaction was quenched with water (20 mL), diluted with ethyl acetate (150 mL), and filtered through Celite®. The filtrate was further diluted with ethyl acetate (150 mL) and washed with water (100 mL). The water layer was reextracted with ethyl acetate (2×100 mL) and the combined organic layer was washed with brine (2×75 mL), dried over MgSO$_4$, filtered, and concentrated under reduced pressure. The resulting residue was purified by flash column chromatography on silica gel eluting with 0-50% ethyl acetate/hexanes to afford compound E3 (1.33 g, 62%) as a yellow oil: $^1$H NMR (300 MHz, CDCl$_3$) δ8.51 (d, J=2.1 Hz, 1H), 8.34 (dd, J=8.4, 2.1 Hz, 1H), 7.76 (d, J=8.4 Hz, 1H), 0.28 (s, 9H); no molecular ion was observed using either ESI or APCI MS.

Step Two. 5-(4-Nitro-2-(trifluoromethyl)phenyl)-4-(trimethylsilyl)-1H-1,2,3-triazole (E4). To a stirred solution of E3 (1.33 g, 4.63 mmol) in N,N-dimethylformamide/methanol (9:1, 10 mL), under a nitrogen atmosphere, was added copper (I) iodide (44 mg, 0.23 mmol) and trimethylsilyl azide (0.92 mL, 6.94 mmol). The resulting suspension was heated to 100° C. for 6.5 h. Following this, the reaction mixture was cooled to ambient temperature and diluted with ethyl acetate (150 mL). The solids were removed by filtration through Celite® and the filtrate was concentrated under reduced pressure to afford crude E4 as a red-brown oil which was used directly in the next step without further purification.

Step Three. 5-(4-Nitro-2-(trifluoromethyl)phenyl)-1H-1,2,3-triazole (E5). To a solution of crude E4 (~1.5 g, 4.63 mmol) in THF (25 mL) at room temperature was added water (~0.1 mL) and tetrabutylammonium fluoride (1 M in THF, 6.95 mL, 6.95 mmol). After stirring overnight (~18 h), water (150 mL) and saturated aqueous sodium bicarbonate (50 mL) were added and the majority of the THF was removed under reduced pressure. The reaction mixture was diluted with ethyl acetate (400 mL) and the layers were separated. The aqueous layer was reextracted with ethyl acetate (100 mL) and the combined organic layer was washed with brine (2×50 mL), dried over MgSO$_4$, filtered, and concentrated under reduced pressure. The resulting residue was purified by flash column chromatography on silica gel eluting with 5-40% ethyl acetate/hexanes to afford compound E5 (350 mg, 29% over 2 steps) as a red semi-solid: $^1$H NMR (500 MHz, CDCl$_3$) δ12.8-11.8 (br s, 1H), 8.68 (d, J=2.5 Hz, 1H), 8.49 (dd, J=8.5, 2.5 Hz, 1H), 8.10 (d, J=8.5 Hz, 1H), 8.04 (d, J=1.0 Hz, 1H); Multimode MS m/z 257 [M–H]$^-$.

Step Four. 4-(1H-1,2,3-Triazol-5-yl)-3-(trifluoromethyl)aniline (E6). To a round-bottomed flask was added tin (II) chloride (387 mg, 2.04 mmol), ethanol (2 mL), and concentrated aqueous HCl (2 mL). The reaction mixture was heated to 40° C. and E5 (117 mg, 0.453 mmol), in ethanol (2 mL), was added. The reaction temperature was increased to 60° C. and maintained for 60 min. The reaction mixture was cooled to room temperature and the ethanol was removed in vacuo. The resulting residue was cooled in an ice-water bath and the pH adjusted to 7 using aqueous sodium hydroxide (2 N, ~14 mL). The reaction mixture was further diluted with water (20 mL) and extracted with ethyl acetate (3×75 mL). The combined organic layer was washed with brine (50 mL), dried over MgSO$_4$, filtered, and concentrated under reduced pressure. The resulting residue was purified by flash column chromatography on silica gel eluting with 5-30% ethyl acetate/methylene chloride to afford compound E6 (75 mg, 73%): $^1$H NMR (300 MHz, CDCl$_3$) δ7.81 (s, 1H), 7.47 (d, J=8.4 Hz, 1H), 7.05 (d, J=2.4 Hz, 1H), 6.87 (dd, J=8.4, 2.4 Hz, 1H), aniline and triazole protons were not observed by $^1$H NMR; ESI MS m/z 229 [M+H]$^+$.

Steps Five and Six. N-(4-(1H-1,2,3-Triazol-5-yl)-3-(trifluoromethyl)phenyl)-6-hydroxy-2,4-dioxo-1,2,3,4-tetrahydropyrimidine-5-carboxamide (E8). To a stirred solution of 1,1'-carbonyldiimidazole (67 mg, 0.411 mmol) and imidazole (2.5 mg, 0.033 mmol) in DMSO (0.75 mL), under a nitrogen atmosphere, was added compound E6 (75 mg, 0.33 mmol) in anhydrous DMSO (1 mL) dropwise over 3 min. The reaction mixture was stirred at ambient temperature for 60 min to provide a solution of compound E7 in DMSO which was used directly in the subsequent step.

In a separate flask, to a suspension of 6-hydroxypyrimidine-2,4(1H,3H)-dione A4 (42 mg, 0.33 mmol) in anhydrous 1,4-dioxane (2.5 mL), under a nitrogen atmosphere, was added triethylamine (0.045 mL, 0.33 mmol) and the reaction mixture heated to 60° C. for 40 min. To this mixture was then added the solution of compound E7 in DMSO dropwise over 5 min. The resulting solution was heated to 80° C. for 3 h. After this time, the brown reaction solution was cooled to ambient temperature, water (3 mL) was added, and the mixture was concentrated under reduced pressure to remove the majority of the 1,4-dioxane. To the reaction residue was added 0.5 N HCl (12 mL) and the mixture heated to 55° C. for 1.5 h. The resulting solid was collected by filtration while the reaction mixture was still hot and dried overnight under high vacuum at 45° C. The brown solid (~100 mg) was suspended in acetonitrile (10 mL) and heated to 65° C. for 45 minutes. The solid was collected by vacuum filtration while the suspension was still hot. The collected solid (~65 mg) was resuspended in 85:15 methylene chloride/methanol (5 mL) and the reaction suspension stirred at room temperature for 30 minutes. The solid was collected by filtration and the filter cake dried under high vacuum to afford E8 (50 mg, 40%) as a light brown solid: $^1$H NMR (500 MHz, DMSO-$d_6$, mixture of tautomers) δ15.4 (br s, ~0.40H), 15.17 (br s, ~0.60H), 12.5-11.1 (br s, 2H), 11.73 (s, 1H), 8.30-8.05 (br s, ~0.4 H), 8.15 (d, J=2.0 Hz, 1H), 8.20-7.80 (br s, ~0.6H), 7.86 (dd, J=8.5, 2.0 Hz, 1H), 7.79-7.71 (br s, 1H), phenol proton was not observed by $^1$H NMR; ESI MS m/z 383 [M+H]$^+$.

Figure 12:
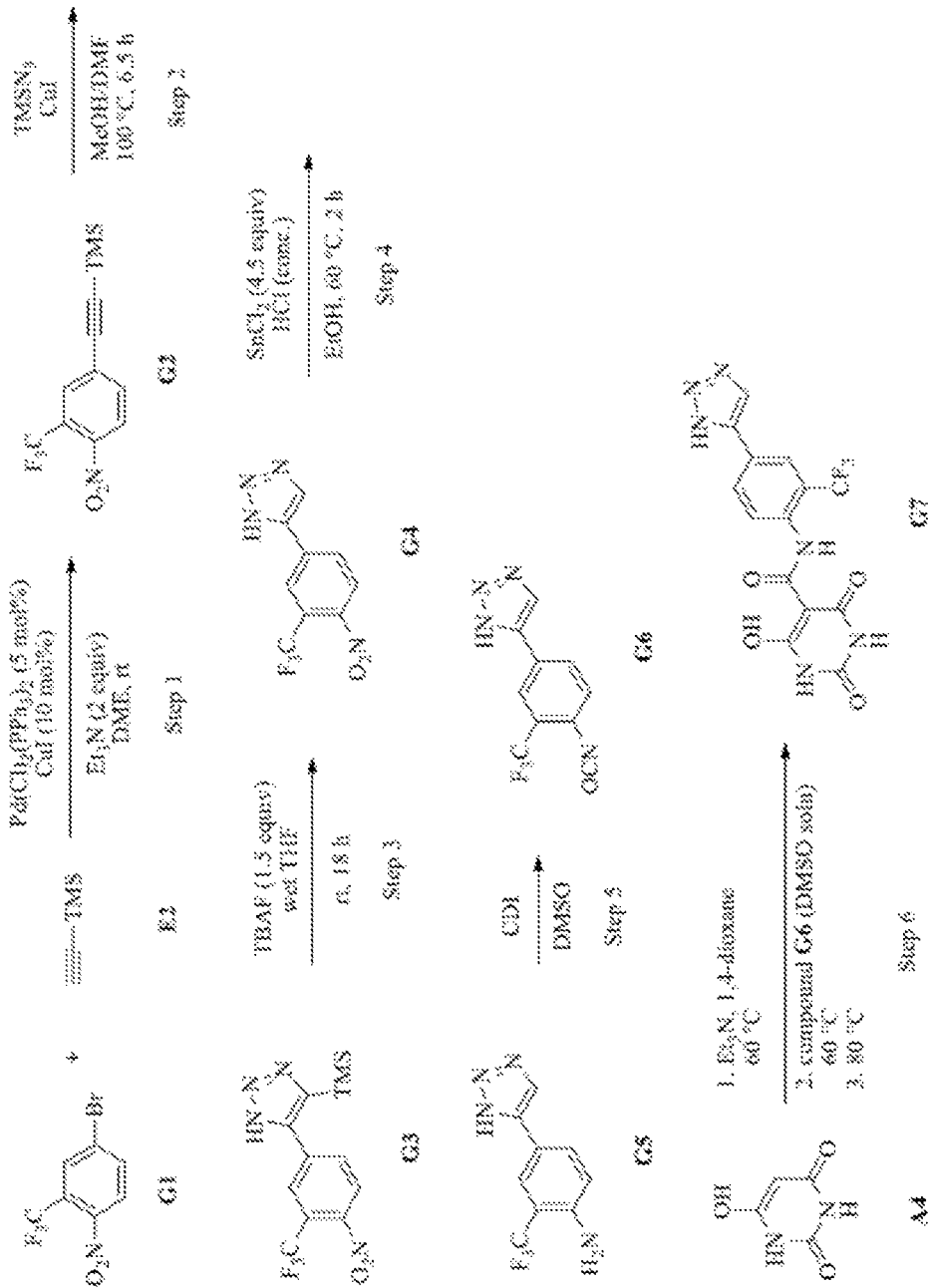
FIG. 12 illustrates a general synthesis scheme for preparation of a compound having a structure represented by Formula (I$_h$).

Example 5: Preparation of N-(4-(1H-1,2,3-triazol-5-yl)-2-(trifluoromethyl)phenyl)-6-hydroxy-2,4-dioxo-1,2,3,4-tetrahydropyrimidine-5-carboxamide (G7, Formula (I$_h$), with Reference to the Synthesis Scheme Illustrated in FIG. 12)

Step One. Trimethyl((4-nitro-3-(trifluoromethyl)phenyl)ethynyl)silane (G2). To a round-bottomed flask was added 5-bromo-2-nitrobenzotrifluoride (G1, 2.50 g, 9.26 mmol), dimethoxyethane (25 mL), copper (I) iodide (88 mg, 0.463 mmol), and triethylamine (3.23 mL, 23.1 mmol). After bubbling nitrogen through the reaction mixture for 5 minutes, trans-dichlorobis(triphenylphosphine) palladium (II) (195 mg, 0.278 mmol) and ethynyltrimethylsilane (E2, 1.95 mL, 13.9 mmol) were added sequentially resulting in a slight exotherm. The reaction mixture was stirred at room temperature (~6 h), then quenched with water (30 mL), diluted with ethyl acetate (150 mL), and filtered through Celite®, washing with ethyl acetate (100 mL). The layers were separated and the organic layer was washed with brine (2×75 mL), dried over MgSO$_4$, filtered, and concentrated under reduced pressure. The resulting residue was purified by flash column chromatography on silica gel eluting with 0-5% ethyl acetate/hexanes to afford compound G2 (2.34 g, 88%): $^1$H NMR (500 MHz, CDCl$_3$) δ7.87 (d, J=1.5 Hz, 1H), 7.85 (d, J=8.5 Hz, 1H), 7.74 (dd, J=8.5, 1.5 Hz, 1H), 0.28 (s, 9H); no molecular ion observed using either APCI or ESI MS.

Step Two. 5-(4-Nitro-3-(trifluoromethyl)phenyl)-4-(trimethylsilyl)-1H-1,2,3-triazole (G3). To a stirred solution of G2 (1.40 g, 4.87 mmol) in N,N-dimethylformamide/methanol (9:1, 10 mL), under a nitrogen atmosphere, was added copper (I) iodide (46 mg, 0.24 mmol) and trimethylsilyl azide (0.97 mL, 7.31 mmol). The resulting suspension was heated to 90° C. for 4 h. The reaction mixture was then cooled to ambient temperature and diluted with ethyl acetate (125 mL). The solids were removed by filtration through Celite® and the filtrate was concentrated under reduced pressure to afford crude G3 as an oil which was used directly in the next step without further purification.

Step Three. 5-(4-Nitro-3-(trifluoromethyl)phenyl)-1H-1,2,3-triazole (G4). To a solution of crude G3 (~1.6 g, 4.87 mmol) in THF (25 mL) at room temperature was added water (~0.1 mL) and tetrabutylammonium fluoride (1 M in THF, 7.30 mL, 7.30 mmol). After stirring overnight (~18 h), saturated aqueous sodium bicarbonate (50 mL) was added and the majority of the THF was removed under reduced pressure. The reaction residue was diluted with ethyl acetate (200 mL), water (50 mL), and saturated aqueous sodium bicarbonate (50 mL). The resulting mixture was stirred for 10 min, then the layers were separated and the aqueous layer was extracted with ethyl acetate (150 mL). The combined organic layer was washed with brine (2×50 mL), dried over MgSO$_4$, filtered, and concentrated under reduced pressure. The resulting residue (2.16 g) was purified by flash column chromatography on silica gel eluting with 5-40% ethyl acetate/hexanes to afford compound G4 (720 mg, 57% over 2 steps): $^1$H NMR (300 MHz, DMSO-$d_6$) δ15.58 (br s, 1H), 8.80 (br s, 1H), 8.45 (s, 1H), 8.43 (dd, J=8.4, 1.5 Hz, 1H), 8.29 (d, J=8.4 Hz, 1H); Multimode MS m/z 257 [M–H]$^-$.

Step Four. 4-(1H-1,2,3-Triazol-5-yl)-2-(trifluoromethyl)aniline (G5). To a round-bottomed flask was added tin (II) chloride (1.16 g, 6.10 mmol), ethanol (6 mL), and concentrated aqueous HCl (2 mL). The reaction mixture was heated to 40° C. and G4 (350 mg, 1.36 mmol), in ethanol (2 mL), was added. The reaction temperature was increased to 60° C. and maintained for 2.5 h. The reaction mixture was cooled to room temperature and the ethanol was removed in vacuo. The resulting residue was cooled in an ice-water bath, water (30 mL) was added, and the pH adjusted to 7 using aqueous sodium hydroxide (2 N, ~20 mL). The reaction mixture was extracted with ethyl acetate (3×100 mL) and the combined organic layer was washed with brine (100 mL), dried over MgSO$_4$, filtered, and concentrated under reduced pressure to afford G5 (290 mg, 93%) as an off-white solid: $^1$H NMR (500 MHz, CDCl$_3$) δ12.0-10.5 (br s, 1H), 7.88 (s, 2H), 7.75 (dd, J=8.5, 1.5 Hz, 1H), 6.82 (d, J=8.5 Hz, 1H), 4.32 (br s, 2H); ESI MS m/z 229 [M+H]$^+$.

Steps Five and Six. N-(4-(1H-1,2,3-Triazol-5-yl)-2-(trifluoromethyl)phenyl)-6-hydroxy-2,4-dioxo-1,2,3,4-tetrahydropyrimidine-5-carboxamide (G7). To a stirred solution of 1,1'-carbonyldiimidazole (258 mg, 1.58 mmol) and imidazole (8.5 mg, 0.13 mmol) in DMSO (1.5 mL), under a nitrogen atmosphere, was added compound G5 (290 mg, 1.27 mmol) in anhydrous DMSO (2 mL) dropwise over 10 min. The reaction mixture was stirred at ambient temperature for 60 min to provide a solution of compound G6 in DMSO which was used directly in the subsequent step.

In a separate flask, to a suspension of 6-hydroxypyrimidine-2,4(1H,3H)-dione A4 (163 mg, 1.27 mmol) in anhydrous 1,4-dioxane (5 mL), under a nitrogen atmosphere, was added triethylamine (0.18 mL, 1.27 mmol) and the reaction mixture heated to 60° C. for 20 min. To this mixture was then added the solution of compound G6 in DMSO dropwise over 5 min. The resulting yellow solution was heated to 80° C. for 3 h. After this time, the reaction solution was cooled to ambient temperature, water (5 mL) was added, and the mixture was concentrated under reduced pressure to remove the majority of the 1,4-dioxane. To the reaction residue was added 0.5 N HCl (35 mL) and the resulting mixture heated to 60° C. for 1 h. The resulting solid was collected by filtration while the reaction mixture was still hot and dried under high vacuum. The collected solid (~400 mg) was suspended in 85:15 methylene chloride/methanol (25 mL) and the mixture stirred at room temperature for 1.5 h. The solid was collected by filtration and dried under high vacuum to afford G7 (389 mg, 80%) as an off-white solid: $^1$H NMR (500 MHz, DMSO-$d_6$, mixture of tautomers) δ15.4 (br s, ~0.35H), 15.14 (br s, ~0.65H), 12.5-11.2 (br s, 2H), 11.82 (s, 1H), 8.70 (br s, ~0.35H), 8.42 (br s, ~0.65H), 8.22 (s, 1H), 8.21 (d, J=8.5 Hz, 1H), 8.12 (d, J=8.5 Hz, 1H), phenol proton was not observed by $^1$H NMR; ESI MS m/z 381 [M–H]$^-$.

Figure 13:
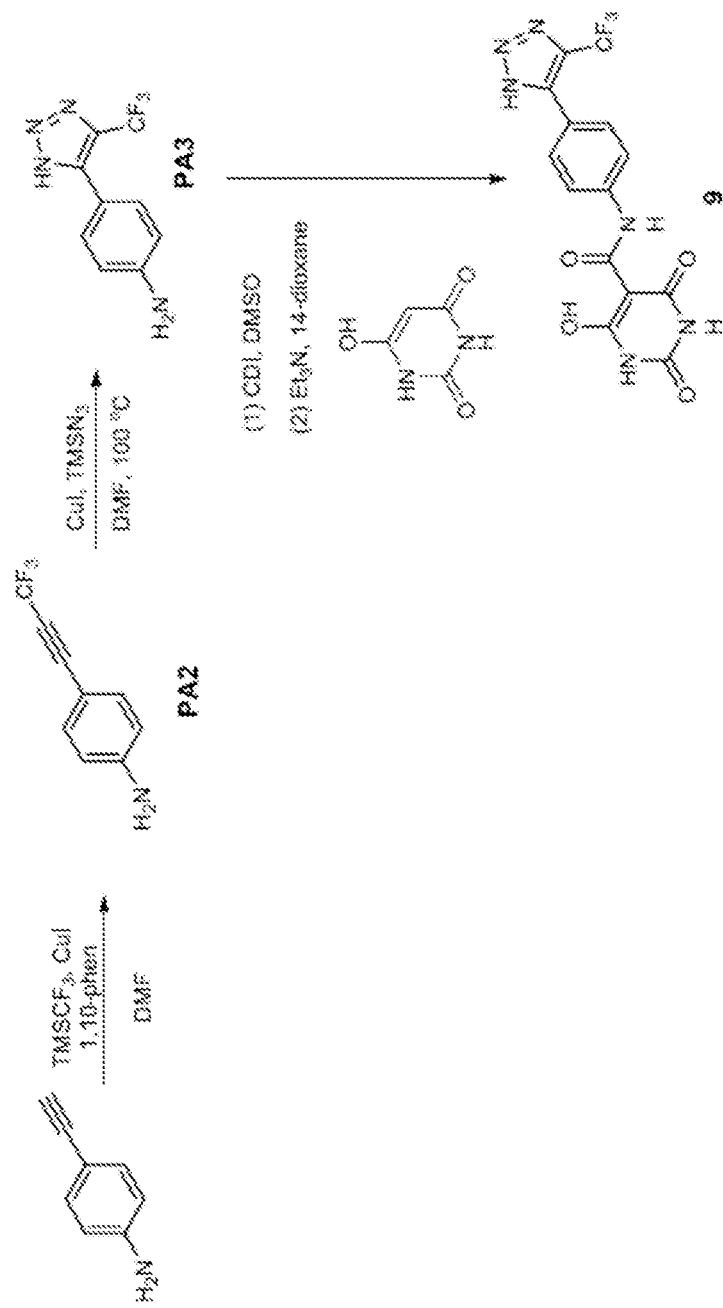
FIG. 13 illustrates a general synthesis scheme for preparation of a compound having a structure represented by Formula (I$_d$).

Example 6: Preparation of 6-hydroxy-2,4-dioxo-N-(4-(5-(trifluoromethyl)-3H-1,2,3-triazol-4-yl)phenyl)-1,2,3,4-tetrahydropyrimidine-5-carboxamide (9, Formula (I$_d$), with Reference to the Synthesis Scheme Illustrated in FIG. 13

Step One. 4-(3,3,3-Trifluoroprop-1-ynyl)benzenamine (PA2). PA2 was synthesized according to reported procedure. (Jiang, X.; Chu, L.; Qing F.-L. *J. Org. Chem.* 2012, 77, 1251-1257.) A flask containing copper iodide (325 mg, 1.71 mmol), potassium fluoride (496 mg, 8.54 mmol), and 1,10-phenanthroline (308 mg, 1.71 mmol) was evacuated and purged with air (3×). Anhydrous DMF (43 mL) was added and stirred for 15 min at rt. (Trifluoromethyl)trimethylsilane (1.3 mL, 8.54 mmol, 2.0 M in THF) was added, then the resulting reaction mixture was heated to 100° C., equipped with a balloon of oxygen gas. A solution of 1-ethynyl-4-nitrobenzene (1.00 g, 8.54 mmol) dissolved in DMF (8.5 mL, 1.0 M) was added over 4 hrs via a syringe pump under a positive atmosphere of oxygen gas (balloon). The reaction was kept at 100° C. for 2 h (the progress of the reaction was monitored by LCMS). The reaction was then cooled to rt, then 0° C. in an ice bath. Deionized water was added, then extracted with diethyl ether (2×), the combined organic extracts were washed with water (5×), then brine, dried over $MgSO_4$, then concentrated. The crude product was purified via ISCO ($SiO_2$, 0 to 50% dichloromethane in hexanes) to yield the product (PA2) as a brown oil (201 mg, 13% yield).

Rf=0.30 (25% dichloromethane in hexanes).

LCMS: m/z $[M+1]^+$=186.16; $R_T$=2.78 min.

HPLC conditions: Column: XTerra RP18, 3.5 µm, 3.0×50 mm; Gradient: 5% to 100% B in 2.5 minutes; 100% B for 1 minute; 1 mL/min; 4 min run. Eluent A: Milli-Q $H_2O$+0.1% Formic Acid; Eluent B: Acetonitrile+0.1% Formic Acid.

Step Two. 4-(5-(Trifluoromethyl)-3H-1,2,3-triazol-4-yl)benzenamine (PA3). To a stirring solution of PA2 (468 mg, 2.53 mmol) dissolved in MeOH/DMF (5.1 mL, 1:9 v/v) at room temperature, under inert atmosphere was added CuI (241 mg, 1.27 mmol) in one-portion, followed by the addition of trimethylsilyl azide (490 µL, mmol). The reaction was sealed in a pressure vessel and heated to 100° C. for 1 h, progress of the reaction was monitored by LCMS. The reaction was then allowed to cool to rt, then concentrated. The crude product was purified via ISCO (0 to 30% ethyl acetate in hexanes over 20 CV) to yield the product (PA3) as a brown oil (121 mg, 21% yield).

Rf=0.39 (50% ethyl acetate in hexanes).

$^1$H NMR (500 MHz, $CDCl_3$) δ7.48 (d, J=8.4 Hz, 2H), 7.14 (d, J=8.5 Hz, 2H).

LCMS: m/z $[M+1]^+$=229.3; $R_T$=1.27 min

HPLC conditions: Column: XBridge C18, 3.5 µm, 4.6×30 mm; Gradient: 5% B for 0.2 min, 5% to 100% B in 1.8 min; 100% B for 1 min; 1 mL/min; 3 min run. Eluent A: Milli-Q $H_2O$+10 mM ammonium formate pH: 3.8; Eluent B: Acetonitrile.

Step Three. 6-hydroxy-2,4-dioxo-N-(4-(5-(trifluoromethyl)-3H-1,2,3-triazol-4-yl)phenyl)-1,2,3,4-tetrahydropyrimidine-5-carboxamide (9). To a stirring solution of PA3 (121 mg, 0.530 mmol) in anhydrous DMSO (530 µL) was added 1,1'carbonyldiimidazole (129 mg, 0.795 mmol) was added at rt, under inert atmosphere. The resulting solution was stirred for 20 min at rt. In a separate flask containing barbituric acid (68 mg, 0.530 mmol) was added anhydrous 1,4-dioxane (1.8 mL), then heated to 50° C. $Et_3N$ (120 µL, 0.848 mmol) was added and stirred for 15 min at 50° C. The isocyanate generated from the amine in DMSO was added to the stirring suspension, then heated to 80° C. until complete consumption of the starting materials were observed via LCMS (20 h). The reaction mixture was cooled to rt, then acidified with 6M HCl (aq), the precipitate formed was isolated, then triturated with MeOH, followed by acetonitrile to yield the product (9) as an off-white solid (10.6 mg, 96.6% purity, 2% yield).

$^1$H NMR (500 MHz, DMSO-d6+AcOD) δ7.71 (d, J=8.6 Hz, 2H), 7.60 (d, J=8.2 Hz, 2H).

LCMS: m/z $[M+1]^+$=383.15; $R_T$=4.49 min min; purity=96.6%.

HPLC conditions: Column: XTerra RP18, 3.5 µm, 3.0×50 mm; Gradient: 5B for 1 minute, 5% to 100% B in 5 minutes; 95% to 5% B in 0.01 minute, 5% B for 0.99 min; 1 mL/min; 4 min run. Eluent A: Milli-Q $H_2O$+0.1% Formic Acid; Eluent B: Acetonitrile+0.1% Formic Acid.

Figure 14:
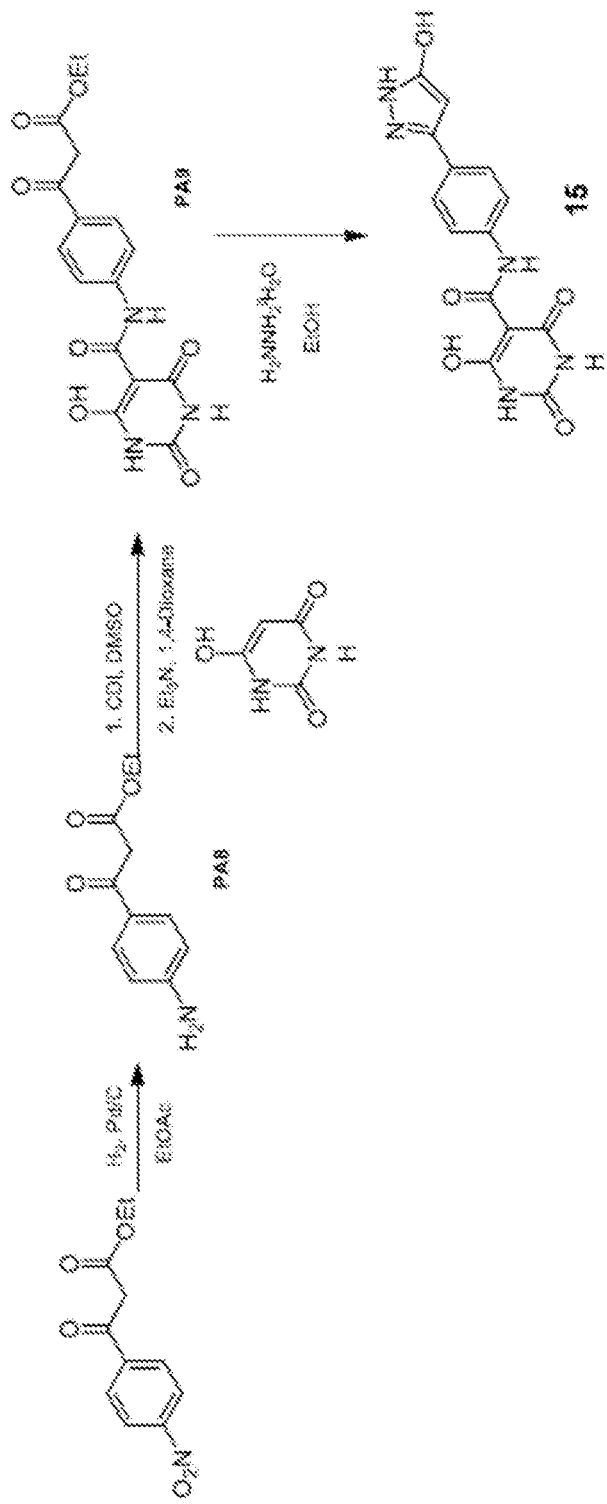
FIG. 14 illustrates a general synthesis scheme for preparation of a compound having a structure represented by Formula (I$_i$).

Example 7: Preparation of 6-hydroxy-N-(4-(3-hydroxy-1H-pyrazol-5-yl)phenyl)-2,4-dioxo-1,2,3,4-tetrahydropyrimidine-5-carboxamide (15, Formula ($I_i$), with Reference to the Synthesis Scheme Illustrated in FIG. 14)

Step One. Ethyl 3-(4-(6-hydroxy-2,4-dioxo-1,2,3,4-tetrahydropyrimidine-5-carboxamido)phenyl)-3-oxopropanoate (PA8). Compound PA8 was synthesized according to general procedure 1 (334 mg, 51% yield).

$^1$H NMR (500 MHz, DMSO-d6) δ7.98 (d, J=8.5 Hz, 2H), 7.71 (d, J=9.5 Hz, 2H), 4.15 (s, 2H), 4.11 (q, J=7.28, 7.28, 7.28 Hz, 2H), 1.17 (t, J=7.2 Hz, 3H).

Step Two. 6-hydroxy-N-(4-(3-hydroxy-1H-pyrazol-5-yl)phenyl)-2,4-dioxo-1,2,3,4-tetrahydropyrimidine-5-carboxamide (15). Solution of PA9 (334 mg, 0.93 mmol) and hydrazine hydrate solution (58 µL, 50% w/w in H2O) in ethanol (5 mL) was heated to 85° C. for 5 h in a sealed tube. The reaction was cooled to rt, then concentrated. The crude product was dissolved in 1,4-dioxane (1 mL) and HCl (4 mL, 1 M solution) and heated to 80° C. for 1 h. The resulting suspension was hot filtered and the precipitate was collected. The impure product was purified via ISCO (C18, 20 to 100% CH3CN [+0.1% TFA] in $H_2O$ with 0.1% TFA, over 20 CV to yield the product (15) as a brown solid (32.5 mg, 94.3% purity, 11% yield) after lyophilization.

$^1$H NMR (500 MHz, $CDCl_3$+TFA) δ11.7-11.0 (br s, 5H).

LCMS: m/z $[M-1]^-$=327.92; $R_T$=0.89 min; purity=94.3%.

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Figure 15:
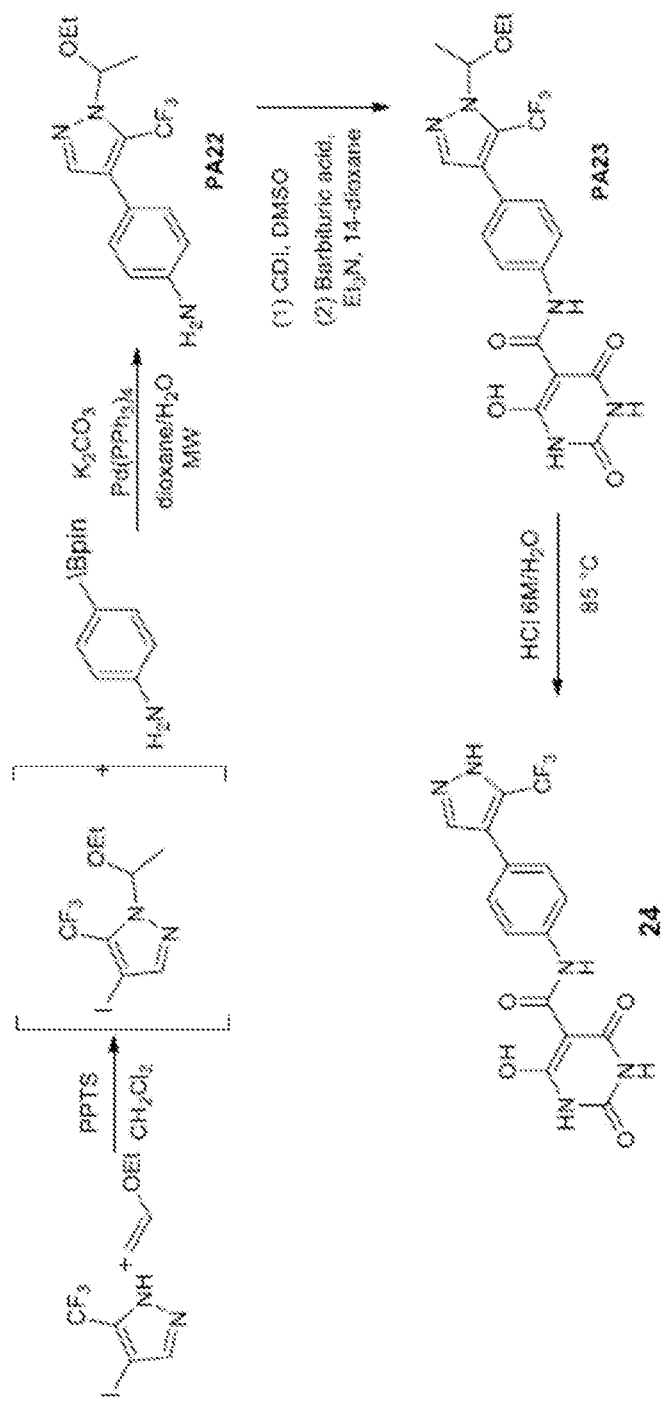
FIG. 15 illustrates a general synthesis scheme for preparation of a compound having a structure represented by Formula ($I_j$).

Example 8: Preparation of 6-hydroxy-2,4-dioxo-N-(4-(5-(trifluoromethyl)-1H-pyrazol-4-yl)phenyl)-1,2,3,4-tetrahydropyrimidine-5-carboxamide (24, Formula ($I_j$), with Reference to the Synthesis Scheme Illustrated in FIG. 15)

Step One. 4-(1-(1-ethoxyethyl)-5-(trifluoromethyl)-1H-pyrazol-4-yl)aniline (PA22). A solution of 4-iodo-3-trifluoromethyl pyrazole (400 mg, 1.52 mmol) and PPTS (9 mg, 0.036 mmol), in $CH_2Cl_2$ (3 mL), was treated with ethyl vinyl ether (0.300 mL, 3.12 mmol) and stirred at rt for 50 min. The volatiles were removed in vacuo. Protected pyrazole, 4-aminophenyl boronic acid pinacolester (403 mg, 1.84 mmol), $K_2CO_3$ (845 mg, 6.11 mmol) and $Pd(PPh_3)_4$(177 mg, 0.15 mmol), in a mixture of dioxane/$H_2O$ (10 mL, 4:1), were reacted in the microwave (150° C., 30 min). The reaction was diluted with $H_2O$, and then extracted twice with EtOAc. The combined extracts were dried over $MgSO_4$, filtered and concentrated in vacuo. The residue was purified by combi-flash chromatography (SiO$_2$ column=40 g, 20% ethyl acetate in hexanes) to afford the title compound (210 mg, 46% yield).

LCMS: m/z [M+1]$^+$=300.60; R$_T$=2.39 min; purity=93%.

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Two. 6-hydroxy-2,4-dioxo-N-(4-(5-(trifluoromethyl)-1H-pyrazol-4-yl)phenyl)-1,2,3,4-tetrahydropyrimidine-5-carboxamide (24). To a solution of CDI (68 mg, 0.419 mmol), in DMSO (0.5 mL), was slowly added a solution of PA22 (100 mg, 0.334 mmol), in DMSO (0.5 mL). The resulting solution was stirred 30 min at rt. To barbituric acid (46 mg, 0.359 mmol), in dioxane (3 mL), was added Et$_3$N (0.055 mL, 0.356 mmol). The resulting mixture was stirred 15 min at 55° C. To this suspension, was added the previous solution of the isocyanate formed in DMSO and the resulting solution was stirred at 80° C. for 1 h. The reaction was cooled to rt, then dioxane was removed in vacuo.

Deprotection was performed with 2 mL of HCl 6M/H$_2$O at 85° C. for 30 min. The reaction mixture was cooled to rt, then diluted with H$_2$O and the precipitate was filtered. The precipitate was triturated with CH$_3$CN, then collected and was added a mixture of CH$_3$CN—H$_2$O, to yield the title compound (24) (7 mg, 4.6% yield, 94.9% purity), after lyophilization.

$^1$H NMR (500 MHz, DMSO) δ13.76 (s, 1H), 11.57 (s, 1H), 8.21 (s, 1H), 7.60 (d, J=8.6 Hz, 2H), 7.45 (d, J=8.7 Hz, 2H).

LCMS: m/z [M+1]$^+$=382.86; R$_T$=1.26 min; purity=94.9%.

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Figure 16:
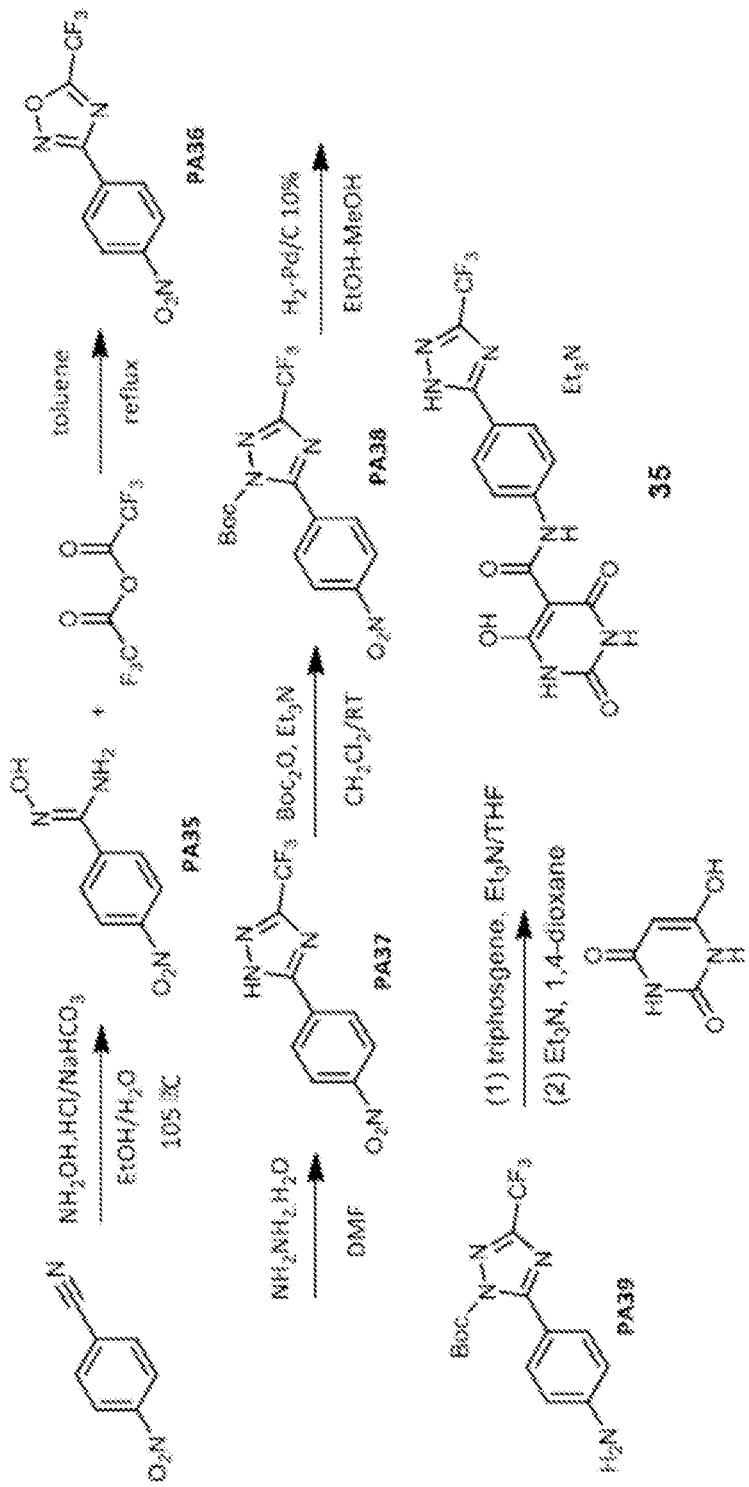
FIG. 16 illustrates a general synthesis scheme for preparation of a compound having a structure represented by Formula ($I_e$).

Example 9: Preparation of 6-hydroxy-2,4-dioxo-N-(4-(3-(trifluoromethyl)-1H-1,2,4-triazol-5-yl)phenyl)-1,2,3,4-tetrahydropyrimidine-5-carboxamide (35, Formula (I$_c$), with Reference to the Synthesis Scheme Illustrated in FIG. 16)

Step One. (Z)-N'-hydroxy-4-nitrobenzimidamide (PA35). 4-Nitrobenzonitrile (940 mg, 6.35 mmol), in EtOH (30 mL), was added to a solution of NH$_2$OH—HCl (3.34 g, 48.06 mmol) and NaHCO$_3$ (2.54 g, 30.23 mmol) in H$_2$O (30 mL). The resulting solution was refluxed 3 h at 105° C. EtOH was evaporated in vacuo and the residue diluted with more H$_2$O. The precipitate was collected, washed with H$_2$O and dried a few hours under high vacuum to provide the product as a yellow solid (996 mg, 86% yield, 88% purity).

LCMS: m/z [M+1]$^+$=182.10; R$_T$=0.85 min; purity=88%.

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile Step Two. 3-(4-nitrophenyl)-5-(trifluoromethyl)-1,2,4-oxadiazole (PA36). A mixture of PA35 (810 mg, 4.47 mmol) and trifluoroacetic anhydride (0.69 mL, 4.96 mmol) in toluene (40 mL), was heated under reflux for 6 h. The solvent was evaporated in vacuo. The residue was diluted with H$_2$O, then extracted twice with AcOEt, the combined organic extract was dried over MgSO$_4$, then concentrated to yield the product (1.06 g, 91% yield).

LCMS: m/z [M+1]$^+$=does not ionize; R$_T$=1.81 min; purity>95%.

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Three. 5-(4-nitrophenyl)-3-(trifluoromethyl)-1H-1,2,4-triazole (PA37). To PA36 (550 mg, 2.12 mmol), in DMF (5 mL) was added excess of hydrazine hydrate (0.85 mL, 13.42 mmol) and the mixture was stirred at rt over 2 days. The reaction mixture was diluted with H$_2$O, the pH was adjusted to 6-7 with 1M HCl and extracted twice with AcOEt. The combined organic phases were washed with H$_2$O (×3), then dried over MgSO$_4$, and then concentrated to yield the product (560 mg, quantitative yield).

LCMS: m/z [M+1]$^+$=259.02; R$_T$=1.53 min; purity=80%.

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Four. tert-butyl 5-(4-nitrophenyl)-3-(trifluoromethyl)-1H-1,2,4-triazole-1-carboxylate (PA38). To a stirring solution of PA37 (550 mg, 2.13 mmol) in CH$_2$Cl$_2$ (5 mL) was added a solution of Boc$_2$O (562 mg, 2.58 mmol), in CH$_2$Cl$_2$ (5 mL), followed by the addition of Et$_3$N (0.36 mL, 2.57 mmol). The resulting solution was stirred at rt overnight. The solvent was evaporated in vacuo. The residue was purified by combi-flash chromatography (SiO$_2$ column=40 g, 20% ethyl acetate in hexanes) to yield the desired product (207 mg, 27% yield, 95% purity).

$^1$H NMR (500 MHz, CDCl$_3$) δ8.36 (d, J=8.9 Hz, 2H), 7.87 (d, J=8.9 Hz, 2H), 1.56 (s, 9H).

LCMS: m/z [M+1]$^+$=258.83; R$_T$=1.84 min; purity=95%.

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Five. tert-Butyl 5-(4-aminophenyl)-3-(trifluoromethyl)-1H-1,2,4-triazole-1-carboxylate (PA39). A solution of PA38 (200 mg, 0.546 mmol), in EtOH (5 mL), was treated with Pd/C 10% (100 mg), 5 mL of MeOH was added. The reaction was fitted with a hydrogen filled balloon and stirred at rt for 1.5 h. The reaction was filtered through a Millex syringe filter. Solvents were evaporated in vacuo. A second filtration was performed through a small pad of Celite. The filtrate was concentrated to yield the product (167 mg, 93% yield, 85% purity).

LCMS: m/z [M-Boc]$^+$=228.87; R$_T$=1.67 min; purity=85%. (15% de-Boc product)

HPLC conditions: Column: XBridge C18, 3.5 µm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Six. 6-hydroxy-2,4-dioxo-N-(4-(3-(trifluoromethyl)-1H-1,2,4-triazol-5-yl)phenyl)-1,2,3,4-tetrahydropyrimidine-5-carboxamide (35). To a solution of triphosgene (25 mg, 0.084 mmol), in THF (0.5 mL) at 0° C., was added PA39 (78 mg, 0.238 mmol), in THF (1.0 mL), followed by Et$_3$N (0.050 mL, 0.360 mmol). The ice bath was removed and the resulting suspension was stirred 1 h at rt. To the barbituric acid (34 mg, 0.265 mmol) in dioxane (2.25 mL), was added Et$_3$N (0.050 mL, 0.360 mmol). The resulting mixture was stirred 15 min at 55° C. To this suspension, was added the previous suspension of the isocyanate formed in THF, followed by 1.0 mL of DMSO and the resulting solution was stirred 1.5 h at 80° C.

The reaction was filtered to remove the precipitate. The filtrate was concentrated n vacuo and H$_2$O was added. The product precipitated and was collected via vacuum filtration to provide the product as a Et$_3$N salt (70 mg). The solid was washed with CH$_3$CN, then added a mixture of CH$_3$CN—H$_2$O, then lyophilized to yield the product as a Et$_3$N salt (28 mg, 31% yield, 97% purity). Note: Boc deprotection was observed during the course of the reaction to yield only the fully deprotected product, 35.

$^1$H NMR (500 MHz, DMSO) δ12.28 (s, 1H), 9.77 (s, 2H), 9.43-8.58 (m, 1H), 7.90 (d, J=8.6 Hz, 2H), 7.71 (d, J=8.7 Hz, 2H), 3.10 (q, J=7.3 Hz, 6H), 1.17 (t, J=7.3 Hz, 9H).

LCMS: m/z [M+1]$^+$=382.99; R$_T$=1.23 min; purity=97%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Figure 17:
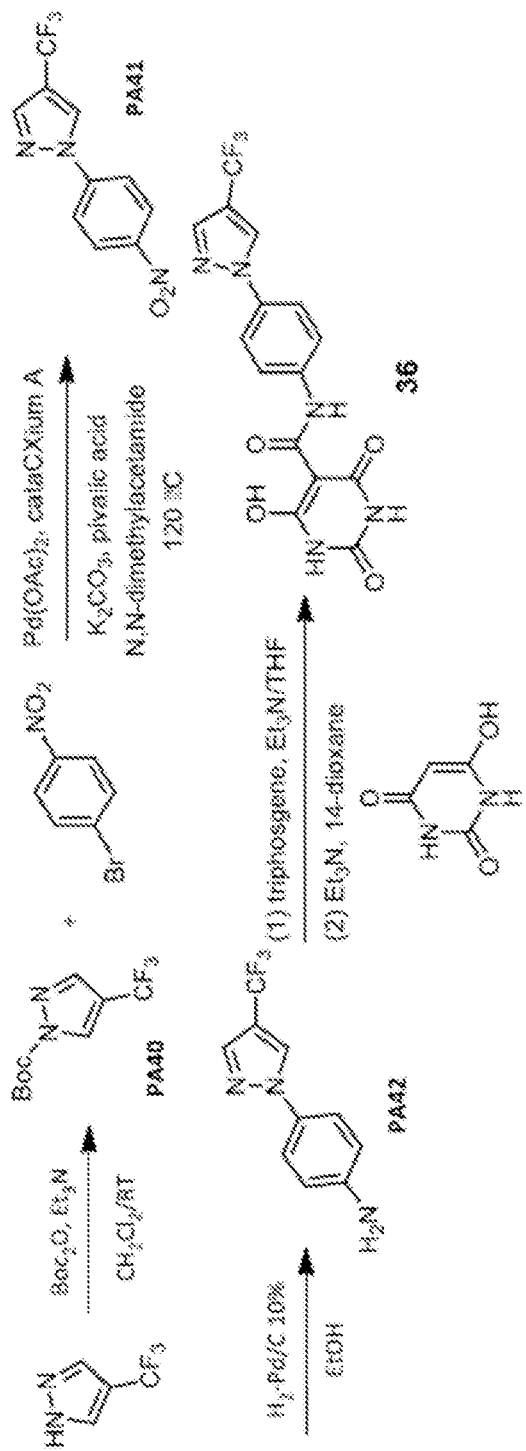
FIG. 17 illustrates a general synthesis scheme for preparation of a compound having a structure represented by Formula ($I_k$).

Example 10: Preparation of 6-hydroxy-2,4-dioxo-N-(4-(4-(trifluoromethyl)-1H-pyrazol-1-yl)phenyl)-1,2,3,4-tetrahydropyrimidine-5-carboxamide (36, Formula (I$_k$), with Reference to the Synthesis Scheme Illustrated in FIG. 17)

Step One. tert-butyl 4-(trifluoromethyl)-1H-pyrazole-1-carboxylate (PA40). To a stirred solution of 4-trifluoromethyl)-1H-pyrazole (300 mg, 2.20 mmol), in CH$_2$Cl$_2$ (5 mL), was added a solution of Boc$_2$O (579 mg, 2.65 mmol), in CH$_2$Cl$_2$ (5 mL), followed by addition of Et$_3$N (0.37 mL, 2.66 mmol). The resulting solution was stirred 4 h at rt. The solvent was evaporated in vacu, the residue was purified by combi-flash chromatography (SiO$_2$ column=40 g, 10% ethyl acetate in hexanes) to yield the product (430 mg 82% yield, >98% purity).

$^1$H NMR (500 MHz, CDCl$_3$) δ8.38 (s, 1H), 7.88 (s, 1H), 1.67 (s, 9H).

LCMS: R$_T$=1.67 min; purity>98%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Two. 1-(4-nitrophenyl)-4-(trifluoromethyl)-1H-pyrazole (PA41). A solution of PA40 (236 mg, 1.00 mmol), 1-bromo-4-nitrobenzene (283 mg, 1.40 mmol), palladium (II) acetate (34 mg, 0.050 mmol), cataCXiumA (27 mg, 0.075 mmol), potassium carbonate (415 mg, 3.00 mmol) and pivalic acid (26 mg, 0.255 mmol), in N,N-dimethylacetamide (4.0 mL), was degassed 10 min with nitrogen prior to heating to 120° C. for 4 h. The reaction was then cooled to rt, diluted with H$_2$O and extracted with AcOEt (×3). The combined organic phases were washed with H$_2$O (×3), dried over MgSO$_4$, then concentrated. The residue was purified by combi-flash chromatography (SiO$_2$ column=24 g, 10% ethyl acetate in hexanes) to yield the product (90 mg, 35% yield, >99% purity).

$^1$H NMR (500 MHz, CDCl$_3$) δ8.39 (d, J=9.2 Hz, 2H), 8.31 (s, 1H), 7.98 (s, 1H), 7.91 (d, J=9.2 Hz, 2H).

LCMS: m/z [M+1]$^+$=257.77; R$_T$=1.75 min; purity>99%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Three. 4-(4-(trifluoromethyl)-1H-pyrazol-1-yl)aniline (PA42). A solution of PA41 (74 mg, 0.288 mmol), in EtOH (2.5 mL), was treated with Pd/C 10% (40 mg). This reaction was fitted with a hydrogen filled balloon and stirred for 2 h at rt. The reaction was filtered through a Millex syringe filter. Solvents were evaporated in vacuo to provide the expected amine (60 mg, 91% yield, >98% purity).

$^1$H NMR (500 MHz, CDCl$_3$) δ8.02 (s, 1H), 7.84 (s, 1H), 7.42 (d, J=8.8 Hz, 2H), 6.75 (d, J=8.8 Hz, 2H), 3.81 (s, 2H).

LCMS: m/z [M+1]$^+$=227.95; R$_T$=1.50 min; purity>98%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile Step Four. 6-hydroxy-2,4-dioxo-N-(4-(4-(trifluoromethyl)-1H-pyrazol-1-yl)phenyl)-1,2,3,4-tetrahydropyrimidine-5-carboxamide (36). To a solution of triphosgene (26 mg, 0.088 mmol), in THF (0.25 mL) at 0° C., was added PA42 (55 mg, 0.242 mmol), in THF (1.0 mL), followed by Et$_3$N (0.050 mL, 0.360 mmol). The ice bath was removed and the resulting suspension was stirred for 30 min at rt. To the barbituric acid (34 mg, 0.265 mmol), in dioxane (1.75 mL) was added Et$_3$N (0.050 mL, 0.360 mmol). The resulting mixture was stirred 20 min at 55° C. To this suspension was added the previous suspension of the isocyanate formed in THF, followed by the addition of 0.75 mL of DMSO and the resulting solution was stirred for 1.5 h at 80° C. The reaction was filtered to remove the precipitate. The filtrate was concentrated in vacuo and H$_2$O was added to the residue. The product crashed out and was filtered to provide the desired product (69 mg). 30 mg of the solid was added 1M HCl, additional H$_2$O was added to the aqueous solution. The solid was filtered and purified by reverse phase chromatography (C18 column=12 g, 0 to 80% CH$_3$CN in water). The pure fractions were combined and lyophilized to provide the desired product (36) (8 mg, 95% purity).

$^1$H NMR (500 MHz, DMSO) δ11.80 (s, 1H), 9.13 (s, 1H), 8.18 (s, 1H), 7.85 (br s, 2H), 7.72 (d, J=8.7 Hz, 2H).

LCMS: m/z [M+1]$^+$=380.09; R$_T$=1.43 min; purity=95%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Figure 18:
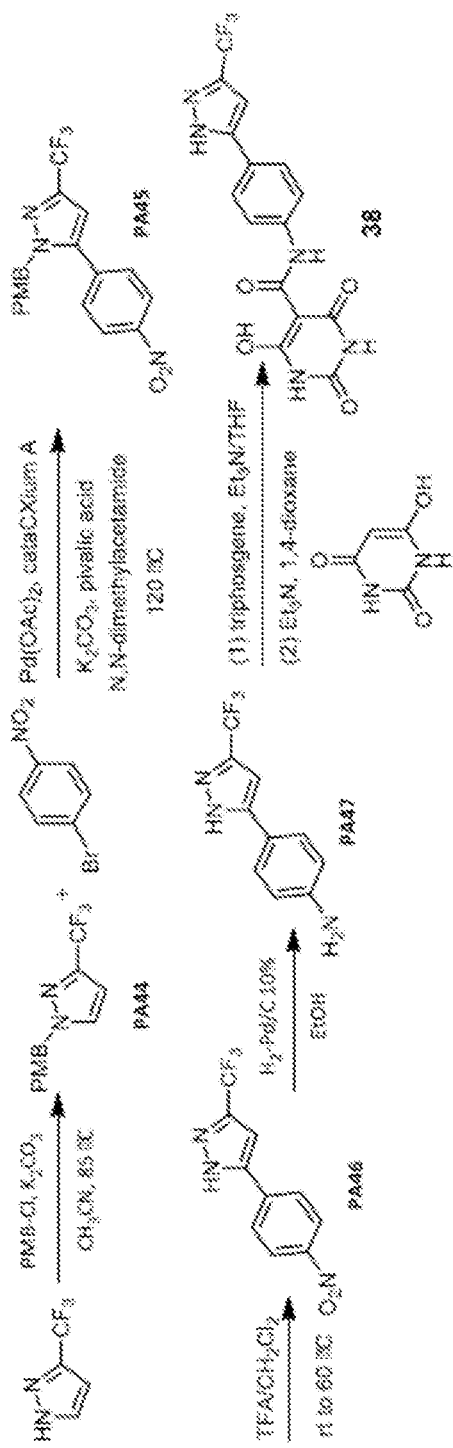
FIG. 18 illustrates a general synthesis scheme for preparation of a compound having a structure represented by Formula ($I_i$).

Example 11: Preparation of 6-hydroxy-2,4-dioxo-N-(4-(3-(trifluoromethyl)-1H-pyrazol-5-yl)phenyl)-1,2,3,4-tetrahydropyrimidine-5-carboxamide (38, Formula (I$_l$), with Reference to the Synthesis Scheme Illustrated in FIG. 18)

Step One. 1-(4-methoxybenzyl)-3-(trifluoromethyl)-1H-pyrazole (PA44). A suspension of 3-(trifluoromethyl)-H-pyrazole (790 mg, 5.81 mmol), 4-methoxybenzylchloride (1.0 g, 6.39 mmol) and potassium carbonate (1.2 g, 8.68 mmol) in CH$_3$CN (10 mL), was heated to reflux for 4 h. The reaction mixture was filtered and concentrated in vacuo. The residue was purified by combiflash chromatography (SiO$_2$ column=40 g, 15% ethyl aceate in hexanes) to yield the desired product (1.4 g, 94% yield, 92% purity).

$^1$H NMR (500 MHz, CDCl$_3$) δ7.32 (d, J=1.3 Hz, 1H), 7.21 (d, J=8.6 Hz, 2H), 6.89 (d, J=6.8 Hz, 2H), 6.50 (d, J=2.4 Hz, 1H), 5.29 (s, 2H), 3.81 (s, 3H).

LCMS: m/z [M+1]$^+$=257.11; R$_T$=1.70 min; purity=92%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q H$_2$O+10 mM ammonium formate pH: 3.8; Eluent B: Acetonitrile.

Step Two. 1-(4-methoxybenzyl)-5-(4-nitrophenyl)-3-(trifluoromethyl)-1H-pyrazole (PA45). A solution of PA44 (500 mg, 1.95 mmol), 1-bromo-4-nitrobenzene (550 mg, 2.72 mmol), palladium(II) acetate (75 mg, 0.111 mmol), cataCXiumA (55 mg, 0.153 mmol), potassium carbonate (810 mg, 5.86 mmol) and pivalic acid (50 mg, 0.490 mmol), in N,N-dimethylacetamide (8.0 mL), was degassed 10 min with nitrogen before heating to 120° C. for 4 h. The reaction was then cooled to rt, diluted with $H_2O$ and extracted twice with AcOEt. The combined organic phases were washed with $H_2O$ (×2) and then brine. The combined organic extract was dried over $MgSO_4$, and then concentrated. The residue was purified by combi-flash chromatography (dry pack, $SiO_2$ column=40 g, 10% ethyl acetate in hexanes) to yield the product (328 mg, 44% yield, 70% purity).

LCMS: m/z $[M+1]^+$=378.04; $R_T$=1.93 min; purity=70%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Step Three. 5-(4-nitrophenyl)-3-(trifluoromethyl)-1H-pyrazole (PA46). To a solution of PA45 (200 mg, 0.53 mmol) in $CH_2Cl_2$ (2.0 mL), was added TFA (1.0 mL). The resulting solution was stirred at rt for 7 days, until full conversion was observed via LCMS. Solvent was evaporated in vacuo. The residue was added in $CH_2Cl_2$ and MeOH a white precipitate was formed the solid was filtered. The filtrate was concentrated, then purified by combi-flash chromatography (dry pack, $SiO_2$ column=24 g, 10% ethyl acetate in hexanes) to provide the desired product (84 mg, 61% yield, >98% purity).

$^1$H NMR (500 MHz, DMSO) δ14.44 (s, 1H), 8.36 (d, J=8.8 Hz, 2H), 8.11 (d, J=8.8 Hz, 2H), 7.48 (s, 1H).

LCMS: m/z $[M+1]^+$=257.84; $R_T$=1.62 min; purity>98%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Step Four. 4-(3-(trifluoromethyl)-1H-pyrazol-5-yl)aniline (PA47). A solution of PA46 (84 mg, 0.327 mmol) in EtOH (2.5 mL), was treated with Pd/C 10% (42 mg). The reaction was fitted with a hydrogen filled balloon and stirred for 1.5 h at rt. The reaction was filtered through a Millex syringe filter. Solvents were evaporated in vacuo to provide the expected amine (73 mg, 98% yield, >98% purity).

$^1$H NMR (500 MHz, $CDCl_3$) δ7.35 (d, J=8.6 Hz, 2H), 6.74 (d, J=8.6 Hz, 2H), 6.64 (s, 1H).

LCMS: m/z $[M+1]^+$=227.88; $R_T$=1.39 min; purity>98%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Step Five. 6-hydroxy-2,4-dioxo-N-(4-(3-(trifluoromethyl)-1H-pyrazol-5-yl)phenyl)-1,2,3,4-tetrahydropyrimidine-5-carboxamide (38). To a solution of triphosgene (15 mg, 0.051 mmol), in THF (0.25 mL) at 0° C., was added PA47 (31 mg, 0.136 mmol), in THF (0.75 mL), followed by $Et_3N$ (0.030 mL, 0.218 mmol). The ice bath was removed and the resulting suspension was stirred 45 min at rt. To the barbituric acid (20 mg, 0.156 mmol), in dioxane (1.5 mL), was added $Et_3N$ (0.030 mL, 0.218 mmol). The resulting mixture was stirred 20 min at 55° C. To this suspension, was added the previous suspension of the isocyanate generated in THF, followed by the addition of DMSO (0.5 mL) and the resulting solution was stirred for 1.5 h at 80° C. The reaction was filtered to remove the precipitate. Solvents of the filtrate were evaporated in vacuo and $H_2O$ was added to the residue. The product crashed out and was filtered to provide the product as an$Et_3N$ salt (1.8 equivalent). This solid was washed with a mixture of $CH_3CN$—MeOH. The filtrate was collected and then co-evaporated with toluene (10×). This solid was added a mixture of $CH_3CN$—$H_2O$, then lyophilized to provide the desired product (38) as the $Et_3N$ salt (26 mg, 50% yield, 95% purity).

$^1$H NMR (500 MHz, DMSO) δ(1.5 eq of $Et_3N$ salt) 13.95 (s, 1H), 11.93 (s, 1H), 11.10 (s, 1H), 9.35 (s, 2H), 7.76 (d, J=8.0 Hz, 2H), 7.65 (d, J=8.0 Hz, 2H), 7.11 (s, 1H), 3.09 (q, J=7.2 Hz, 9H), 1.18 (t, J=7.2 Hz, 13.5H).

LCMS: m/z $[M-1]^-$=380.09; $R_T$=1.34 min; purity=95%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Figure 19:
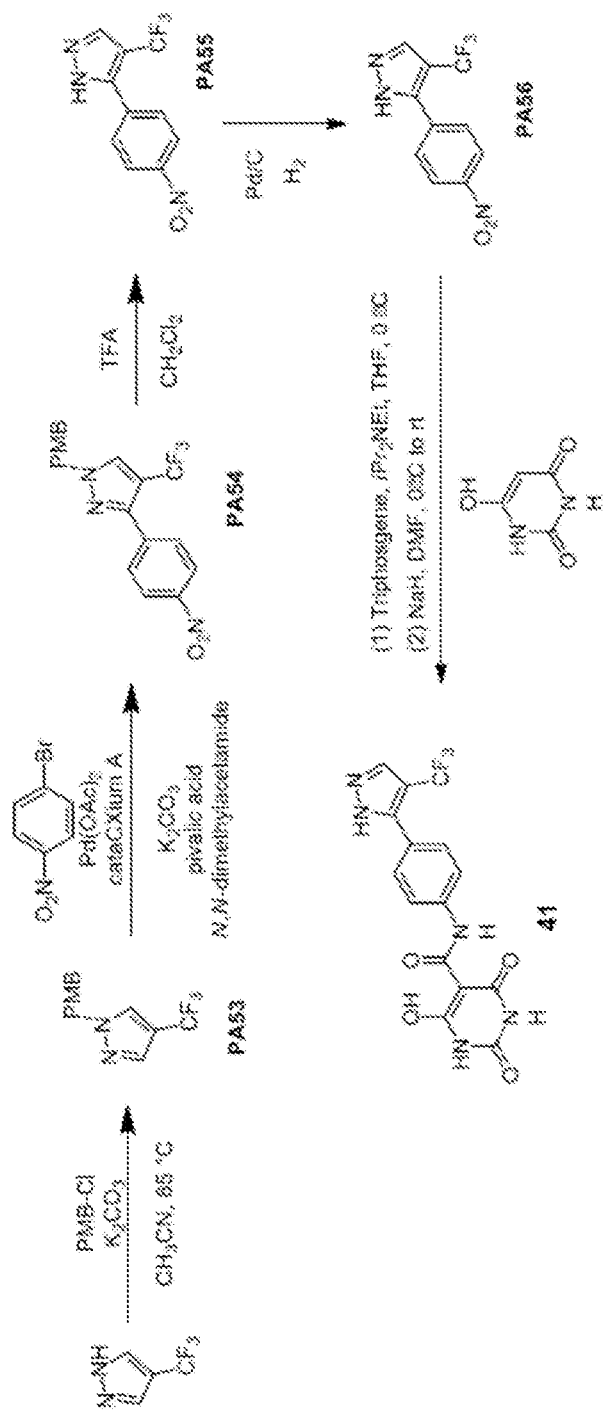
FIG. 19 illustrates a general synthesis scheme for preparation of a compound having a structure represented by Formula ($I_m$).

Example 12: Preparation of 6-hydroxy-2,4-dioxo-N-(4-(4-(trifluoromethyl)-1H-pyrazol-5-yl)phenyl)-1,2,3,4-tetrahydropyrimidine-5-carboxamide (41, Formula ($I_m$), with Reference to the Synthesis Scheme Illustrated in FIG. 19)

Step One. 1-(4-Methoxybenzyl)-4-(trifluoromethyl)-1H-pyrazole (PA53). A suspension of 4-(trifluoromethyl)-1H-pyrazole (502 mg, 3.69 mmol), 4-methoxybenzylchloride (0.44 mL, 4.24 mmol) and potassium carbonate (770 mg, 5.57 mmol), in $CH_3CN$ (7.5 mL) was heated to reflux for 4 h. The reaction mixture was filtered and concentrated in vacuo. The residue was purified by combiflash chromatography (column=40 g, solvents=Hexanes to 90:10 Hex/AcOEt) and 903 mg (95% yield) of the desired product were recuperated.

LCMS: $R_T$=1.66 min; purity>97%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Step Two. 1-(4-Methoxybenzyl)-3-(4-nitrophenyl)-4-(trifluoromethyl)-1H-pyrazole (PA54). A solution of PA53 (500 mg, 1.95 mmol), 1-bromo-4-nitrobenzene (550 mg, 2.72 mmol), palladium(II) acetate (75 mg, 0.11 mmol), cataCXiumA (55 mg, 0.15 mmol), potassium carbonate (810 mg, 5.86 mmol) and trimethylacetic acid (50 mg, 0.49 mmol), in N,N-dimethylacetamide (4.0 mL), was degazed 10 minutes with nitrogen before heating the reaction mixture at 120° C. for 3.5 h. The reaction was then cooled to rt, then diluted with $H_2O$ and extracted twice with AcOEt. The combined organic phases were washed with $H_2O$ (×2) and brine, and the organic extract was dried over $MgSO_4$, then concentrated. The residue was purified by combi-flash chromatography (dry pack, column=40 g, 10% ethyl acetate in hexanes) to provide the product (104 mg, 14% yield).

LCMS: m/z $[M+1]^+$=does not ionize; $R_T$=1.86 min; purity=66%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Step Three. 5-(4-Nitrophenyl)-4-(trifluoromethyl)-1H-pyrazole (PASS). To a solution of PA54 (104 mg, 0.404 mmol) in $CH_2Cl_2$ (4.0 mL), was added TFA (1.0 mL). The resulting solution was stirred 3 weeks at t, then concentrated to yield the product as a brown oil (79 mg, 79% yield, 70% purity).

LCMS: m/z $[M-1]^-$=256.12; $R_T$=1.57 min.; purity=70%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Step Four. 4-(4-(Trifluoromethyl)-1H-pyrazol-5-yl)aniline (PA56). PA55 (79 mg, 0.307 mmol) was dissolved in MeOH (7.7 mL). To the solution was added Pd/C (22 mg, 10% on charcoal) under $N_2$. The reaction was then stirred under $H_2$ for 2 h, after LCMS showed that the reaction is complete, the reaction was mixture was filtered through a pad a Celite. The filtrate was collected and the solvent was removed in vacuo to yield the product as a pink solid (51 mg, 73% yield), without further purification.

LCMS: m/z $[M-1]^-$=226.08; $R_T$=1.30 min.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Step Five. 6-hydroxy-2,4-dioxo-N-(4-(4-(trifluoromethyl)-1H-pyrazol-5-yl)phenyl)-1,2,3,4-tetrahydropyrimidine-5-carboxamide (41). Triphosgene (12 mg, 0.115 mmol) was added to a solution of PA57 (26 mg, 0.115 mmol) and $iPr_2NEt$ (26 μL, 0.344 mmol) in anhydrous THF (380 μL), at 0° C., under inert atmosphere. The reaction was allowed to stir at 0° C. for 1 h, anhydrous DMF (0.5 mL) was then added to form a homogenous solution. In a separate flask containing barbituric acid (15 mg, 0.115 mmol) was dissolved in anhydrous DMF (0.7 mL), $iPr_2NEt$ (26 μL, 0.150 mmol) was added at rt. The reaction was stirred for 30 min at rt. The isocyanate generated from PA57 in THF/DMF was added dropwise to the stirring suspension, the reaction was heated to 60° C. for 2.5 h. The reaction mixture was cooled to rt, then acidified with 6M HCl (aq), the precipitate formed was isolated, then triturated with water, MeOH, followed by acetonitrile to yield the pure product (41) as a beige solid (25.9 mg, 97.6% purity, 57% yield).

$^1$H NMR (500 MHz, DMSO-d6+DCl in $D_2O$) δ8.06 (s, 1H), 7.44 (s, 4H).

LCMS: m/z $[M-1]^-$=380.21; $R_T$=1.28 min; purity=97.6%.

HPLC conditions: Column: XBridge C18, 3.5 μm, 4.6×30 mm; Gradient: 5% B for 0.2 min, 5% to 100% B in 1.8 min; 100% B for 1 min; 3 mL/min Eluent A: Milli-Q $H_2O$+10 mM ammonium formate pH: 3.8; Eluent B: Acetonitrile.

Figure 20:
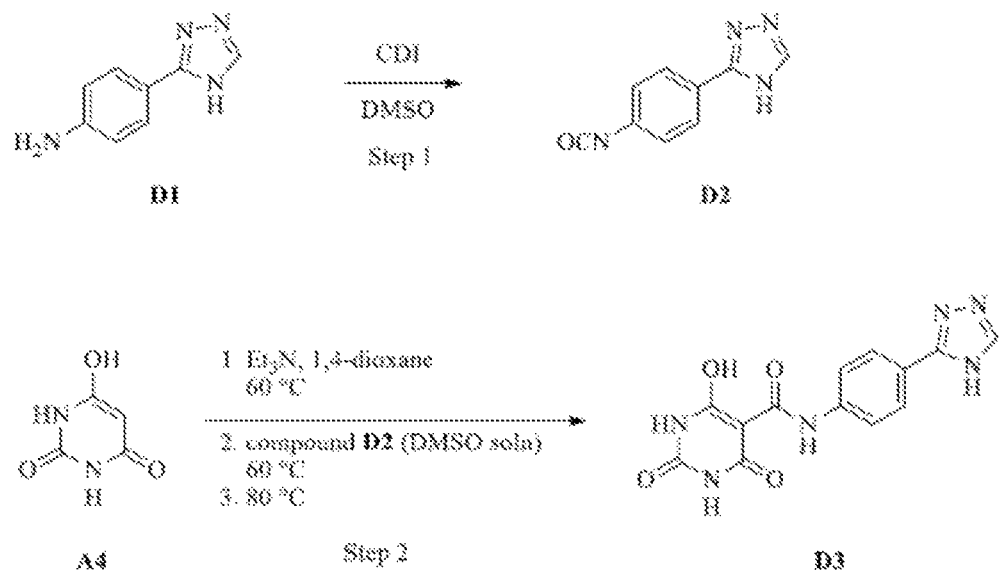
FIG. 20 illustrates a general synthesis scheme for preparation of a compound having a structure represented by Formula ($I_b$).

Example 13: Preparation of N-(4-(4H-1,2,4-triazol-3-yl)phenyl)-6-hydroxy-2,4-dioxo-1,2,3,4-tetrahydropyrimidine-5-carboxamide (D3, Formula ($I_b$), with Reference to the Synthesis Scheme Illustrated in FIG. 20)

Steps One and Two. N-(4-(4H-1,2,4-Triazol-3-yl)phenyl)-6-hydroxy-2,4-dioxo-1,2,3,4-tetrahydropyrimidine-5-carboxamide (D3, RLBN1050).

To a stirred solution of 1,1'-carbonyldiimidazole (405 mg, 2.49 mmol) and imidazole (11 mg, 0.16 mmol) in DMSO (1.5 mL), under a nitrogen atmosphere, was added compound D1 (250 mg, 1.56 mmol) in anhydrous DMSO (1.5 mL) dropwise over 8 min. The reaction mixture was stirred at ambient temperature for 20 min to provide a solution of compound D2 in DMSO which was used directly in the subsequent step.

In a separate flask, to a suspension of 6-hydroxypyrimidine-2,4(1H,3H)-dione A4 (200 mg, 1.56 mmol) in anhydrous 1,4-dioxane (6 mL) under a nitrogen atmosphere was added triethylamine (0.22 mL, 1.56 mmol). After the addition was complete the mixture was heated to 60° C. and stirred for 45 min. To this mixture was then added the solution of compound D2 in DMSO dropwise over 10 min. The resulting reaction mixture was heated to 80° C. for 2 h, cooled to ambient temperature, water (3 mL) was added and the mixture was concentrated under reduced pressure to remove the majority of the 1,4-dioxane. To the reaction residue was added 0.5 N HCl (50 mL) and the resulting mixture heated to 75° C. for 20 min. The resulting orange-beige solid was collected by filtration while the reaction mixture was still hot. The solid (~390 mg) was suspended in acetonitrile (30 mL) and heated to reflux for 30 minutes. The resulting solid was collected by vacuum filtration while the suspension was still hot. The solid obtained was resuspended in acetonitrile (30 mL) and the reaction suspension heated to 70° C. for 30 min. The solid present was collected by filtration while the reaction mixture was still hot. The resulting solid (~310 mg) was suspended in 1,4-dioxane (25 mL), heated to 80° C. for 1.5 h, then filtered while the reaction mixture was still hot. The collected solid was suspended in 30% methanol/methylene chloride (35 mL), then stirred for 30 min, and the supernatant was decanted. This procedure was repeated using additional 30% methanol/methylene chloride (~35 mL) and the resulting solid was dried overnight under high vacuum to afford D3 as a light brown solid: $^1$H NMR (500 MHz, DMSO-d$_6$) δ12.11 (br s, 1H), 11.69 (s, 1H), 11.44 (br s, 1H), 8.47 (br s, 1H), 8.04 (d, J=8.7 Hz, 2H), 7.67 (d, J=8.7 Hz, 2H), two protons were not observed by $^1$H NMR; Multimode MS m/z 313 [M−H]$^-$.

Example 14: Bioactivity Assays

The biological activities of compounds having structures represented by Formula (I), were evaluated in two assays: xanthine oxidase activity and URAT1 activity.

Xanthine oxidase inhibition was determined using a standard fluorescence-based assay for xanthine oxidase activity (McHale A, Grimes H, Coughlan M P: Int J Biochem. 10:317-9, 1979) with minor variations. The procedure was internally standardized using allopurinol and DPI as controls for all experiments after determination of their optimal inhibitory concentrations. Experiments on test compounds were performed in triplicate in multi-well plates using 10 concentrations of each compound that ranged over a 3-fold dilution.

URAT1 (SLC22A12) activity was evaluated in a cellular uptake assay using a 96-well plate with stably transfected URAT-1/CHO cells. $^3$H-orotate was used as the test transport agent, which was measured in a liquid scintillation counter, using benzbromarone as a positive control, and DMSO and non-transfected CHO cells as negative controls (Solvo Biotechnology, Boston, Mass.). Generally determined over 7 concentrations (range, 0.01 to 150 μM), a semi-log plot (percent relative transport of oratate vs. time) was generated to determine the concentration at which 50% inhibition was observed (i.e., the IC50).

The results of these assays are shown in the following Table:

| Compound | URAT1 IC50 (μM) | Xanthine Oxidase IC50 (μM) |
| --- | --- | --- |
| Formula ($I_a$) |  | 6.5 |
| Formula ($I_b$) |  | 1.4 |
| Formula ($I_c$) | 0.11 | 12.2 |
| Formula ($I_d$) |  | 5.9 |
| Formula ($I_e$) |  | 14.5 |
| Formula ($I_f$) |  | 70.1 |
| Formula ($I_g$) | 2.7 | 2.2 |
| Formula ($I_h$) | 1.6 | 1.2 |
| Formula ($I_i$) | 9.1 | 1.3 |
| Formula ($I_j$) |  | 16.3 |
| Formula ($I_k$) |  | 68 |
| Formula ($I_l$) |  | 67.9 |
| Formula ($I_m$) |  | 25.2 |

| Compound | URAT1 IC50 (μM) | Xanthine Oxidase IC50 (μM) |
|---|---|---|
| Allopurinol | >300† | 2.0 to 5.0 |
| Lesinurad | 18.61* 52.5 ± 5.9†* | >300† |

†Presentation estimate; Proc. EULAR Abstract #THU0357, 2008
*URAT1 assay as described herein Formula (I$_b$,) Formula (I$_h$), and Formula (I$_i$) are more potent inhibitors of xanthine oxidase than allopurinol. Formula (I$_g$), Formula (I$_h$) and Formula (I$_i$) have the additional unexpected advantage of being bifunctional, as they are also potent inhibitors of URAT1. Formula (I$_c$), Formula (I$_g$) and Formula (I$_h$) are more potent inhibitors of URAT1 than lesinurad. Bifunctional compounds Formula (I$_g$) and Formula (I$_h$) have activity against xanthine oxidase which is comparable to allopurinol.

While most Formula I compounds were potent inhibitors, the extent of inhibition of each enzyme was different. Such variability allows the intelligent selection of a pharmaceutically acceptable product that exhibits greater or lesser inhibition of one or the other enzyme target. For example, greater inhibition of XO might be deemed preferable for a patient whose primary metabolic defect was over-production of uric acid. Conversely, greater inhibition of URAT1 might be deemed preferable, for a patient whose primary metabolic defect was under-excretion of uric acid. However, it should be noted that almost all patients with hyperuricemia will benefit from reduction in serum uric acid, and bifunctional compounds can be expected to exert a beneficial effect in such patients. The practitioner, guided by the present disclosure, will be able to select particular compounds as appropriate for a specific use based on the level of skill in the art.

By way of comparison, allopurinol has an IC50 for XO ranging from about 2.0 to about 5.0 μM and an IC50 for URAT1 of >300 μM. Lesinurad has an IC50 for XO of >300 μM and an IC50 for URAT1 ranging from 18 to 53 μM. Thus, neither of these compounds is considered bifunctional, since both are selective inhibitors of only one enzyme that affects either production or excretion of uric acid. In contrast, certain of the compounds described herein are not only bifunctional, several are substantially more potent inhibitors of either or both XO and URAT1.

While in many clinical situations it is desirable to treat hyperuricemia with a drug that is highly potent against both XO and URAT1, it is also contemplated that selection of a particular compound of the invention for treatment of hyperuricemia may be based on the phenotype of the hyperuricemic patient being treated (i.e., the relative contributions of over-production of uric acid and under-excretion of uric acid to the patient's specific disease). Where over-production of uric acid predominates, use of compounds according to the invention that are substantially more potent against XO than URAT1 may be appropriate. Where under-excretion of uric acid predominates, use of compounds according to the invention that are substantially more potent against URAT1 than XO may be appropriate. Although the genetics of these two pathways are not completely understood, chemical testing to determine the extent to which each contributes to the hyperuricemia of a particular patient has been published, and is expected to be useful to determine the patient's disease phenotype for selection of an appropriate drug.

Although the invention herein has been described with reference to particular embodiments, it is to be understood that these embodiments are merely illustrative of the principles and applications of the present invention. It will be apparent to those skilled in the art that various modifications and variations can be made to the method and apparatus of the present invention without departing from the spirit and scope of the invention. Thus, it is intended that the present invention include modifications and variations that are within the scope of the appended claims and their equivalents.

What is claimed is:

1. A compound selected from the group consisting of
   a) compounds having a structure represented by Formula (I):

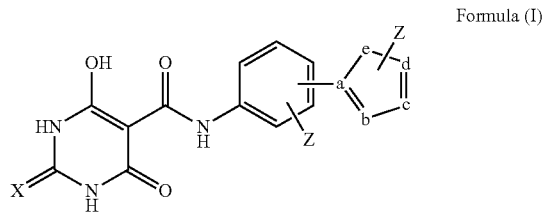

Formula (I)

wherein
   X is O or S;
   each Z is independently present or absent and, if present, is independently selected from —CF$_3$, —OR$^2$, and aryl, wherein R$^2$ is H, alkyl or aryl; and;
   a, b, c, d, and e are each independently carbon, nitrogen, CH, or NH, with the proviso that 2 or 3 of a, b, c, d and e are nitrogen and Z is not connected directly to a nitrogen except that Z may optionally be connected to a nitrogen at a, b, c, d, or e by replacement of the hydrogen of an NH group when Z is phenyl; and
   b) tautomers of any of the foregoing compounds.

2. The compound according to claim 1, wherein the 5-member heterocyclic ring is substituted or unsubstituted triazole, or substituted or unsubstituted pyrazole.

3. The compound according to claim 1, wherein Z is —OH or —CF$_3$ on the 5-member heterocyclic ring and/or —CF$_3$— on the phenyl ring.

4. The compound according to claim 1, wherein both Z are absent, wherein Z is absent from the phenyl group and present on the 5-member heterocyclic ring, or wherein Z is present on the phenyl group and absent from the 5-member heterocyclic ring.

5. The compound according to claim 4, wherein Z is absent from the phenyl group, and Z on the heterocyclic 5-membered ring is CF$_3$.

6. The compound according to claim 4, wherein Z on the phenyl group is CF$_3$, and Z is absent from the heterocyclic 5-membered ring.

7. The compound according to claim 1, which is selected from the group consisting of compounds having a structure represented by

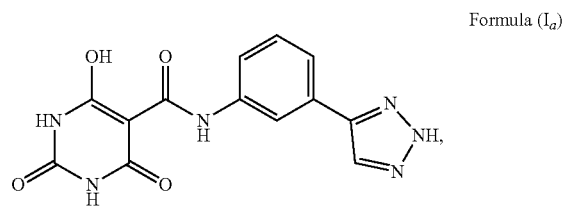

Formula (I$_a$)

Formula (I_b)
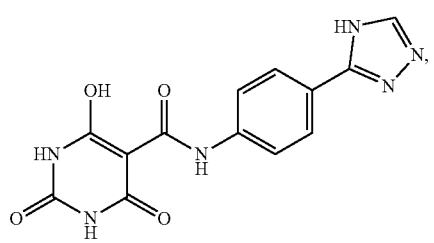
Formula (I_c)
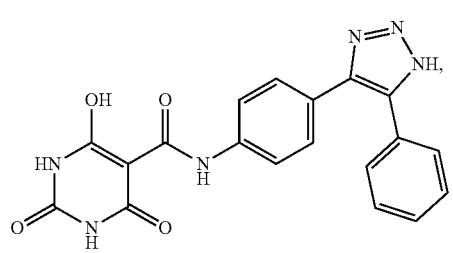
Formula (I_d)
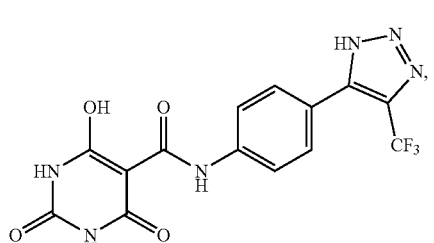
Formula (I_e)
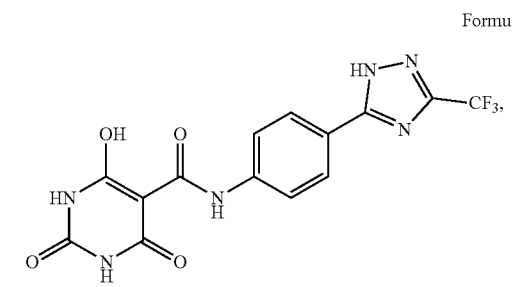
Formula (I_f)
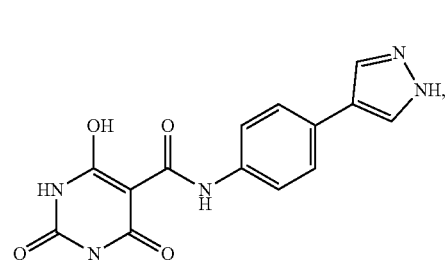
Formula (I_g)
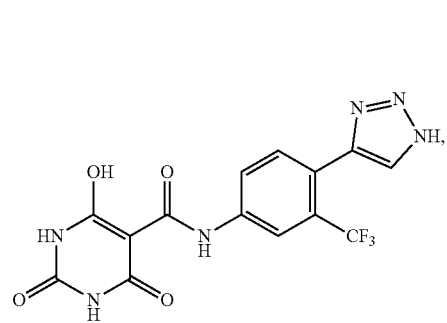
Formula (I_h)
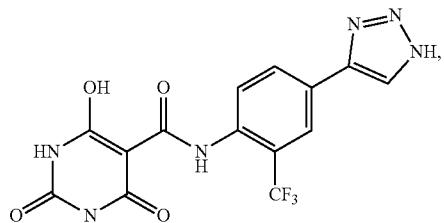
Formula (I_i)
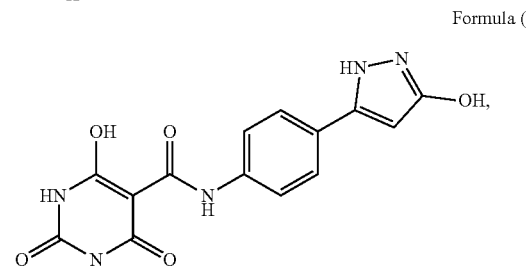
Formula (I_j)
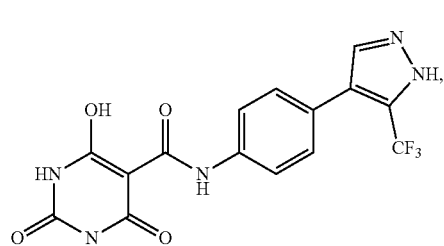
Formula (I_k)
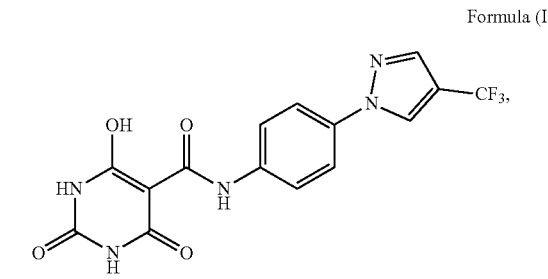
Formula (I_l)
1.5 Et$_3$N
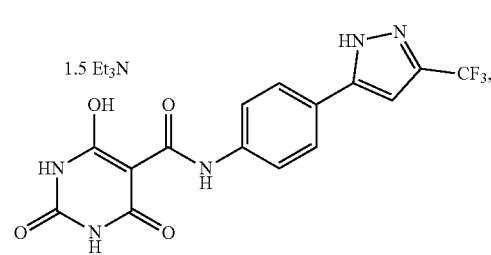
Formula (I_m)
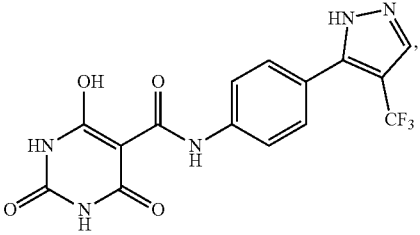
and tautomers thereof.
8. A pharmaceutical composition comprising a compound according to claim 1; a tautomer thereof, or a combination thereof, and a pharmaceutically acceptable carrier.

9. The pharmaceutical composition according to claim 8 which is formulated for controlled or extended release of the compound or combination thereof.

10. The pharmaceutical composition according to claim 8, which comprises a compound having a structure represented by Formula (I$_a$)
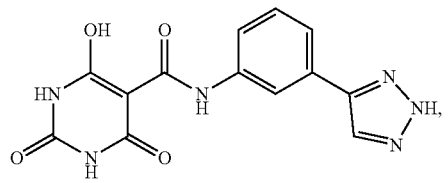

Formula (I$_b$)
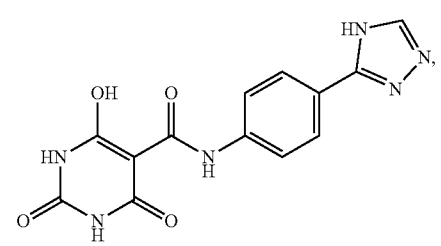

Formula (I$_c$)
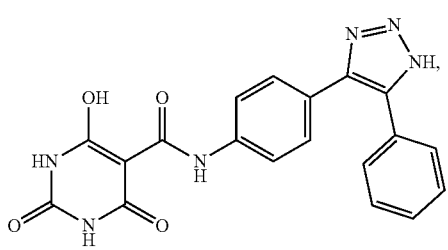

Formula (I$_d$)
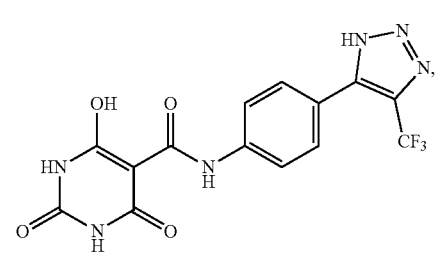

Formula (I$_e$)
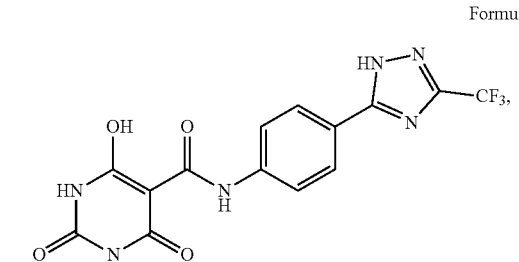

Formula (I$_f$)
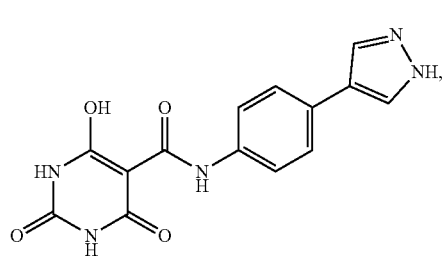

-continued

Formula (I$_g$)
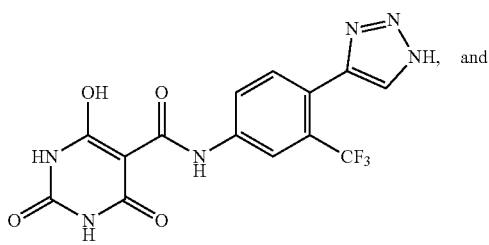

Formula (I$_h$)
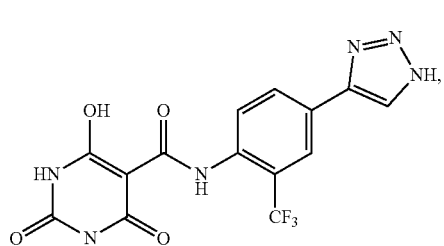

Formula (I$_i$)
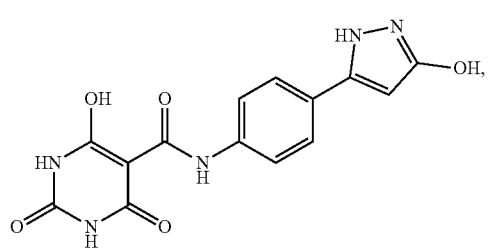

Formula (I$_j$)
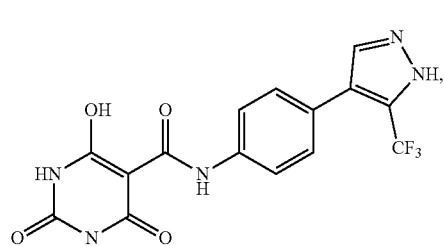

Formula (I$_k$)
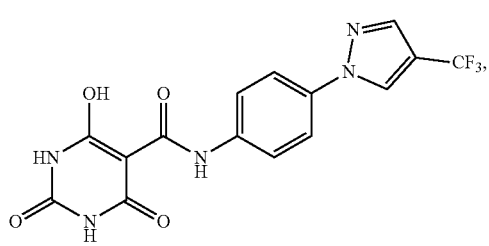

Formula (I$_l$)
1.5 Et$_3$N
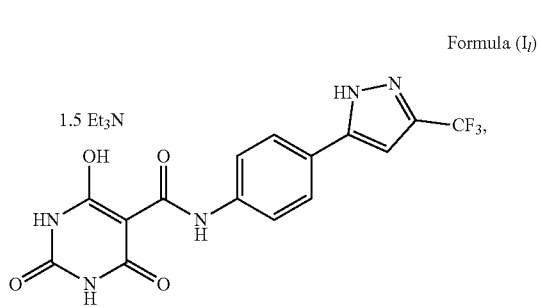

-continued

Formula (I_m)

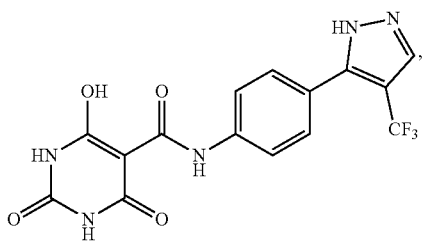

a tautomer of any of the foregoing, or a combination thereof.

11. A method for reducing uric acid levels in blood or serum of a subject comprising administering to a subject in need thereof a compound according to claim 1; a tautomer thereof, or a combination thereof, in an amount effective to reduce blood or serum uric acid levels.

12. The method according to claim 11, wherein administering the compound treats a disorder of uric acid metabolism caused by, or associated with, hyperuricemia.

13. The method according to claim 12 wherein the disorder of uric acid metabolism is selected from the group consisting of gout, hyperuricemia, tumor lysis syndrome, kidney disease, arthritis, kidney stones, kidney failure, urolithiasis, plumbism, hyperparathyroidism, psoriasis, inborn genetic errors of metabolism, Lesch-Nyhan syndrome, sarcoidosis, cardiovascular disease, atherosclerosis, and disorders of uric acid metabolism associated with transplantation of blood, bone marrow or solid organs.

14. The method according to claim 13, wherein the disorder of uric acid metabolism is gout.

15. The method according to claim 11, wherein a daily dose of about 20 to about 1,500 mg/m²/day is administered.

16. The method according to claim 11, wherein the compound, tautomer thereof, or combination thereof is administered by injection, infusion, or oral administration.

17. The method according to claim 16, wherein the compound, tautomer thereof, or combination thereof is administered by intravenous infusion or bolus injection.

18. The method according to claim 11, which comprises administration of a compound having a structure represented by Formula (I_a)

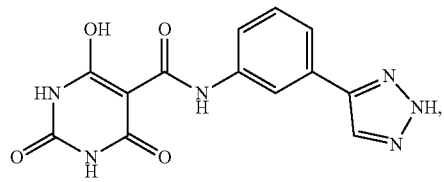

Formula (I_b)

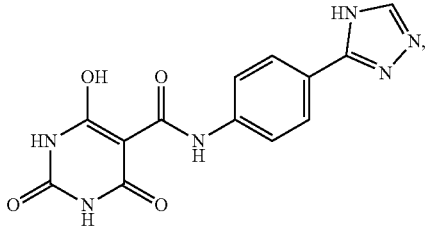

-continued

Formula (I_c)

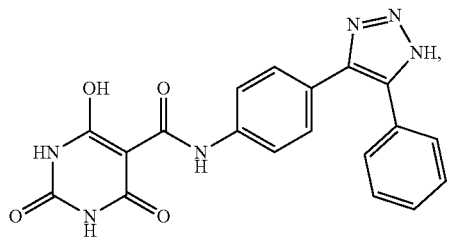

Formula (I_d)

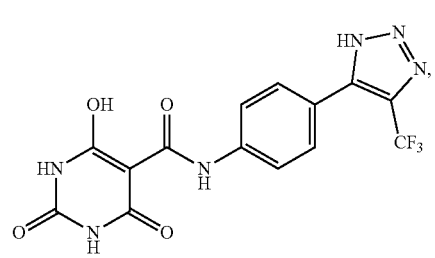

Formula (I_e)

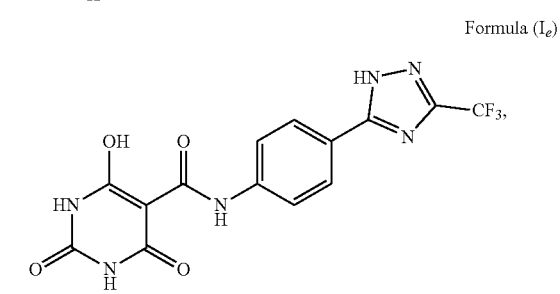

Formula (I_f)

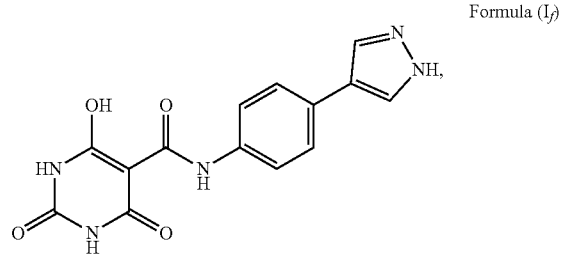

Formula (I_g)

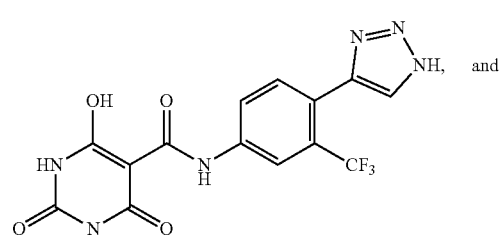     and

Formula (I_h)

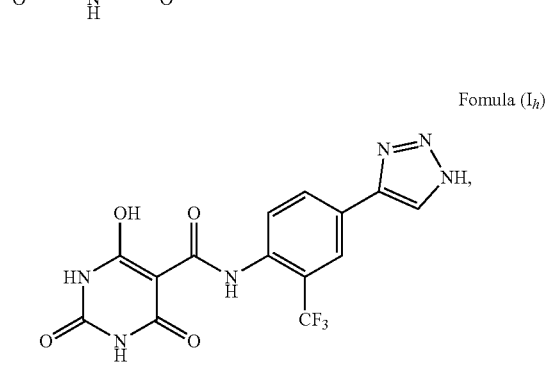

Formula (I_i)
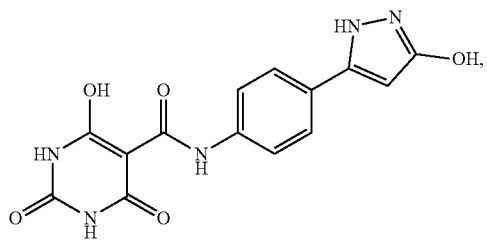
Formula (I_j)
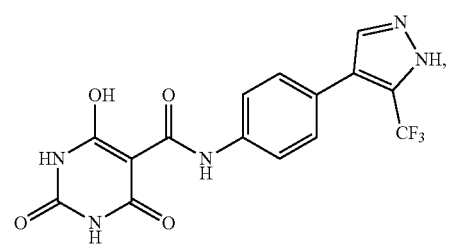
Formula (I_k)
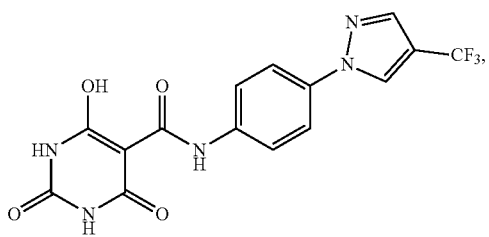
Formula (I_l)
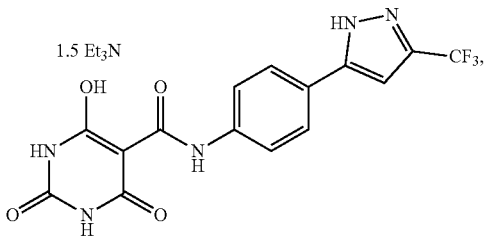
1.5 Et₃N
Formula (I_m)
a tautomer of any of the foregoing, or a combination thereof.
* * * * *